United States Patent
Atarot et al.

(10) Patent No.: US 10,799,302 B2
(45) Date of Patent: Oct. 13, 2020

(54) INTERFACE FOR LAPAROSCOPIC SURGERIES—MOVEMENT GESTURES

(71) Applicant: TransEnterix Europe S.a.r.l., Lugano (TI) (CH)

(72) Inventors: Gal Atarot, Kfar Saba (IL); Motti Frimer, Zichron Yaakov (IL); Tal Nir, Haifa (IL); Tami Harel, Haifa (IL)

(73) Assignee: Transenterix Europe S.a.r.l., Lugano (TI) (CH)

( * ) Notice: Subject to any disclaimer, the term of this patent is extended or adjusted under 35 U.S.C. 154(b) by 240 days.

(21) Appl. No.: 15/322,452

(22) PCT Filed: Jul. 9, 2015

(86) PCT No.: PCT/IL2015/050718
§ 371 (c)(1),
(2) Date: Dec. 28, 2016

(87) PCT Pub. No.: WO2016/005988
PCT Pub. Date: Jan. 14, 2016

(65) Prior Publication Data
US 2018/0325604 A1 Nov. 15, 2018

Related U.S. Application Data

(60) Provisional application No. 62/022,688, filed on Jul. 10, 2014.

(51) Int. Cl.
*A61B 1/00* (2006.01)
*A61B 34/00* (2016.01)
(Continued)

(52) U.S. Cl.
CPC .......... *A61B 34/25* (2016.02); *A61B 1/00147* (2013.01); *A61B 1/3132* (2013.01);
(Continued)

(58) Field of Classification Search
CPC . A61B 1/00147; A61B 1/3132; A61B 5/0035; A61B 5/06; A61B 5/114;
(Continued)

(56) References Cited

U.S. PATENT DOCUMENTS 6,714,841 B1 * 3/2004 Wright ............... A61B 1/00039
600/118
2006/0281971 A1 * 12/2006 Sauer ..................... A61B 34/20
600/109

(Continued)

FOREIGN PATENT DOCUMENTS

JP 6063003 A 3/1994
WO 2013/027200 A2 2/2013
(Continued)

OTHER PUBLICATIONS

International Search Report for PCT/IL2015/050718, dated Nov. 10, 2015.
(Continued)

*Primary Examiner* — Ankit D Tejani

(57) ABSTRACT

The present invention discloses a surgical maneuvering system, in which movement of a moving element is used to control a surgical device such as a surgical tool or an endoscope. The moving element can be a tool or a portion of an operator's body. The relationship between the moving element and the surgical device can be any of: motion of a moving element controlling motion of a surgical device, motion of a moving element controlling an action of a surgical device, a command of a moving element controlling motion of a surgical device, or a command of a moving element controlling an action of the device. Commands are typically arbitrary movements such as shaking a tool. Actions are changes in a surgical device that do not change its overall position, such as closing a grasper.

33 Claims, 24 Drawing Sheets

(51) Int. Cl.
*A61B 5/00* (2006.01)
*A61B 1/313* (2006.01)
*A61B 5/06* (2006.01)
*A61B 5/11* (2006.01)
*A61B 17/00* (2006.01)
*A61B 34/20* (2016.01)

(52) U.S. Cl.
CPC .............. *A61B 5/0035* (2013.01); *A61B 5/06* (2013.01); *A61B 5/1114* (2013.01); *A61B 5/7425* (2013.01); *A61B 5/7475* (2013.01); *A61B 2017/00119* (2013.01); *A61B 2017/00207* (2013.01); *A61B 2034/2048* (2016.02); *A61B 2505/05* (2013.01); *A61B 2560/0487* (2013.01); *A61B 2562/028* (2013.01); *A61B 2562/0219* (2013.01)

(58) Field of Classification Search
CPC ..... A61B 5/7425; A61B 5/7475; A61B 34/25; A61B 2017/00119; A61B 2017/00207; A61B 2034/2048; A61B 2505/05; A61B 2505/0487; A61B 2560/0487; A61B 2562/0219; A61B 2562/028
USPC ........................................................ 600/424
See application file for complete search history.

(56) References Cited

U.S. PATENT DOCUMENTS

| | | | | |
|---|---|---|---|---|
| 2007/0161853 | A1* | 7/2007 | Yagi | A61B 1/00009 600/109 |
| 2008/0262297 | A1 | 10/2008 | Gilboa et al. | |
| 2008/0287803 | A1* | 11/2008 | Li | A61B 8/12 600/466 |
| 2012/0071892 | A1* | 3/2012 | Itkowitz | B25J 13/086 606/130 |
| 2014/0236159 | A1* | 8/2014 | Haider | A61B 17/1626 606/88 |

FOREIGN PATENT DOCUMENTS

| | | | | |
|---|---|---|---|---|
| WO | WO-2013027200 | A2 * | 2/2013 | ......... A61B 1/00006 |
| WO | 2014/049598 | A1 | 4/2014 | |
| WO | 2016/005988 | A1 | 1/2016 | |

OTHER PUBLICATIONS

Written Opinion of the International Search Authority for PCT/IL2015/050718, dated Nov. 10, 2015.

* cited by examiner

INTERFACE FOR LAPAROSCOPIC SURGERIES—MOVEMENT GESTURES

CROSS-REFERENCE TO RELATED APPLICATIONS

This application is a U.S. National Phase filing under 35 U.S.C. 371 of International (PCT) Patent Application No. PCT/IL2015/050718, filed Jul. 9, 2015, which claims priority from U.S. Provisional Patent Application No. 62/022,688, filed Jul. 10, 2014, both of which are incorporated by reference in their entirety.

FIELD OF THE INVENTION

The present invention generally pertains to a system and method for providing an improved interface for laparoscopic surgeries.

BACKGROUND OF THE INVENTION

Laparoscopic surgery is becoming increasingly popular with patients because the scars are smaller and their period of recovery is shorter. Laparoscopic surgery requires special training of the surgeon or gynecologist and the theatre nursing staff. The equipment is often expensive and is not available in all hospitals. During laparoscopic surgery it is often required to shift the spatial placement of the endoscope in order to present the surgeon with the optimal view. Conventional laparoscopic surgery makes use of either human assistants that manually shift the instrumentation or alternatively robotic automated assistants (such as JP patent No. 06063003).

In laparoscopic surgery, the surgeon performs the operation through small holes using long instruments and observing the internal anatomy with an endoscope camera. The surgeon's performance is largely dependent on the camera position relative to the instruments and on a stable image shown at the monitor. In general, the surgeon needs a close-up view of the area in which he wants to work, however, there are times when an overview of a large portion of the working area, such as an overall view of the interior of the abdomen, is desirable.

U.S. patent application US2006/0281971 discloses a method and apparatus for presenting three-dimensional data to a physician is provided to facilitate the flexible navigation of an endoscope and surgical instruments with respect to anatomical structures. In accordance with a first embodiment a first set of data corresponding to a three dimensional model of a patient's anatomy is received. This three-dimensional model may be rendered from images taken in CT or MRI scanning, as discussed above In accordance with this embodiment, this model is then combined with a second set of data corresponding to a view obtained from an endoscope. In another embodiment, the view from the illustrative endoscope is displayed as an inset image on the display of the three-dimensional image. In yet another embodiment, the three-dimensional image comprises a graphical representation of at least a first surgical instrument, such as said endoscope. The surgeon may select among various combinations of views and may zoom in or out from any particular view.

However, U.S. patent application US2006/0281971 does not disclose a means of controlling the endoscope.

U.S. Pat. No. 6,714,841 discloses an automated camera endoscope in which the surgeon is fitted with a head mounted light source that transmits the head movements to a sensor, forming an interface that converts the movements to directions for the mechanical movement of the automated assistant. Alternative automated assistants incorporate a voice operated interface, a directional key interface, or other navigational interfaces. The above interfaces share the following drawbacks:

a. A single directional interface that provide limited feedback to the surgeon
b. A cumbersome serial operation for starting and stopping movement directions that requires the surgeon's constant attention, preventing the surgeon from keeping the flow of the surgical procedure.

Research has suggested that these systems divert the surgeons focus from the major task at hand. Therefore technologies assisted by magnets and image processing have been developed to simplify interfacing control. However, these improved technologies still fail to address another complicating interface aspect of laparoscopic surgery, in that they do not allow the surgeon to signal to automated assistants, to human assistants or to surgical colleagues which instrument his attention is focused on.

Hence there is still a long felt need for improving the interface between the surgeon, his surgical colleagues or human assistants and an endoscope system, for laparoscopic surgery

SUMMARY OF THE INVENTION

It is an object of the present invention to disclose a system for providing improved interface for laparoscopic surgeries.

It is another object of the present invention to disclose a maneuvering system, comprising: (a) at least one endoscope adapted to real-time provide at least one image of a field of view; (b) at least one surgical tool; (c) at least one maneuvering mechanism in active communication with at least one selected from a group consisting of said at least one endoscope, said at least one surgical tool and any combination thereof; said maneuvering mechanism is configured to maneuver at least one selected from a group consisting of said at least one endoscope, said at least one surgical tool and any combination thereof; in at least two dimensions; (d) a computer program which, when executed by a data processor, is in communication with a member of a group consisting of said at least one endoscope, said at least one surgical tool and any combination thereof; said program, when executed by a data processor is configured to (i) real-time image process said at least one image; (ii) detect movement of at least a portion of said at least one surgical tool; wherein, if said detected movement of at least a portion of said at least one surgical tool is within a predetermined protocol of input movement, then at least one of the following is being held true: (a) said endoscope is maneuvered by means of said maneuvering mechanism according to a predetermined protocol of output movement; (b) said at least one surgical tool is maneuvered by means of said maneuvering mechanism according to a predetermined protocol of output movement; (c) said at least one surgical tool is activated; (d) a second surgical tool is maneuvered by means of said maneuvering mechanism according to said at least one output movement protocol; (e) a second surgical tool is activated according to said at least one output movement protocol; and, (f) any combination thereof.

It is another object of the present invention to disclose a system for maneuvering a surgical tool, comprising: (a) at least one surgical tool; (b) at least one endoscope; (c) at least one maneuvering mechanism in active communication with said at least one surgical tool and said at least one endoscope; said maneuvering mechanism is configured to maneuver at least one selected from a group consisting of said at least one surgical tool, said at least one endoscope and any combination thereof in at least two dimensions; (d) at least one sensor configured to indicate at least one movement of at least one moving element; said sensor indicates movement of said moving element if a current 3D position or current signal, $3D_{current}$, is substantially different from a previous 3D position or previous signal of the same, $3D_{previous}$; (e) either a wired or wireless communicable database for consecutively storing said $3D_{current}$ and said $3D_{previous}$ of each of said moving element; and (f) a data processor comprising a computer program in communication with said at least one surgical tool and said at least one maneuvering mechanism; said program, when executed by said data processor is configured to identify if said movement of said moving element is within a predetermined protocol of input movement; wherein, if said detected movement of said moving element is within said predetermined protocol of input movement or said detected position of said moving element is within a predetermined protocol of input positions, then at least one of the following is being held true: (a) said endoscope is maneuvered by means of said maneuvering mechanism according to a predetermined protocol of output movement; (b) said at least one surgical tool is maneuvered by means of said maneuvering mechanism according to a predetermined protocol of output movement; and (c) said at least one surgical tool is activated; (d) a second surgical tool is maneuvered by means of said maneuvering mechanism according to said at least one output protocol; (e) a second surgical tool is activated according to said at least one output protocol; and, (f) any combination thereof.

It is another object of the present invention to disclose a maneuvering system, comprising: (a) at least one endoscope adapted to real-time provide at least one image of a field of view; (b) at least one surgical tool; (c) at least one maneuvering mechanism in active communication with at least one selected from a group consisting of said at least one endoscope, said at least one surgical tool and any combination thereof; said maneuvering mechanism is configured to maneuver at least one selected from a group consisting of said at least one endoscope, said at least one surgical tool and any combination thereof; in at least two dimensions; (d) a computer program which, when executed by a data processor, is in communication with a member of a group consisting of said at least one endoscope, said at least one surgical tool and any combination thereof; said program, when executed by a data processor is configured to determine, from said image of said field of view, an input protocol; wherein, if said input protocol is within a predetermined input command, at least one output command is being activated.

It is another object of the present invention to disclose a system for maneuvering a surgical tool, comprising (a) at least one surgical tool; (b) at least one endoscope; (c) at least one maneuvering mechanism in active communication with said at least one surgical tool and said at least one endoscope; said maneuvering mechanism is configured to maneuver said at least one surgical tool in at least two dimensions; (d) at least one sensor configured to indicate a member of a group consisting of: movement of at least one moving element, position of at least one moving element, and any combination thereof; said sensor indicates said position of said moving element via a current 3D position or current signal, $3D_{current}$; and said sensor indicates said movement of said moving element if said current 3D position or current signal, $3D_{current}$, is substantially different from at least one previous 3D position or previous signal of the same, $3D_{previous}$; (e) either a wired or wireless communicable database for storing said $3D_{current}$ for each said moving element, and, to indicate movement, consecutively storing said $3D_{current}$ and said $3D_{previous}$ of each of said moving element; and (f) a data processor comprising a computer program in communication with said at least one surgical tool and said at least one maneuvering mechanism; said program, when executed by said data processor is configured to identify at least one of a group consisting of: said movement of said moving element is within a predetermined input protocol; said position of said moving element is within a predetermined input protocol and any combination thereof; wherein, if said input command is within a predetermined input protocol, at least one output command is being activated.

It is another object of the present invention to disclose the system as described above, wherein said input command is selected from a group consisting of: at least one said surgical tool is maneuvered according to an input movement protocol; at least a portion of at least one said surgical tool is positioned in a predetermined region of said field of view; at least a portion of at least one said surgical tool is positioned less than a predetermined distance from an edge of said field of view; at least a portion of at least one said surgical tool is oriented at a predetermined angle in said field of view; at least one said surgical tool is activated; at least one said surgical tool is deactivated; at least one said surgical tool is articulated; at least one said endoscope is maneuvered according to an input movement protocol; at least one said endoscope is articulated; at least one said endoscope is zoomed; at least one said endoscope is activated; at least one said endoscope is deactivated; at least a portion of a second endoscope is positioned in a predetermined region of said field of view; at least a portion of a second endoscope is positioned less than a predetermined distance from an edge of said field of view; at least a portion of a second endoscope is oriented at a predetermined angle in said field of view; a relationship between at least two articles; and any combination thereof.

It is another object of the present invention to disclose the system as described above, wherein said input movement protocol is selected from a group consisting of: moving said at least one surgical tool parallel to the X axis; moving said at least one surgical tool parallel to the Y axis; moving said at least one surgical tool parallel to the Z-axis; rotational movement of said at least one surgical tool around an axis parallel to the X axis; rotational movement of said at least one surgical tool around an axis parallel to the Y axis; rotational movement of said at least one surgical tool around an axis parallel to the Z axis; shaking said at least one surgical tool, moving said at least one surgical tool in at least a portion of a circle, moving said at least one surgical tool in at least a portion of an oval, moving said at least one surgical tool in at least a portion of an ellipse, moving said at least one surgical tool in a straight line, moving said at least one surgical tool in a zigzag, moving said at least one endoscope parallel to the X axis; moving said at least one endoscope parallel to the Y axis; moving said at least one endoscope parallel to the Z-axis; rotational movement of said at least one endoscope around an axis parallel to the X axis; rotational movement of said at least one endoscope around an axis parallel to the Y axis; rotational movement of said at least one endoscope around an axis parallel to the Z axis; shaking said surgical tool, moving said at least one endoscope in at least a portion of a circle, moving said at least one endoscope in at least a portion of an oval, moving said at least one endoscope in at least a portion of an ellipse, moving said at least one endoscope in a straight line, moving said at least one endoscope in a zigzag, and any combination thereof.

It is another object of the present invention to disclose the system as described above, wherein said activation is selected from a group consisting of: opening said at least one surgical tool, closing said at least one surgical tool, causing said at least one surgical tool to function, stopping said at least one surgical tool from functioning, introducing at least one said surgical tool to the surgical environment, removing at least one said surgical tool from the surgical environment, introducing at least one said endoscope to a surgical environment, removing at least one said endoscope from a surgical environment and any combination thereof.

It is another object of the present invention to disclose the system as described above, wherein said output command is selected from a group consisting of: said at least one surgical tool is maneuvered according to an output movement protocol; at least a portion of at least one said surgical tool is repositioned to a predetermined region of said field of view; at least a portion of at least one said surgical tool is oriented at a predetermined angle in said field of view; said at least one surgical tool is activated; at least one said surgical tool is deactivated; in at least one said surgical tool, at least one of a group consisting of an articulation angle, an articulation length and any combination thereof is altered; at least one said surgical tool is tagged; at least one said surgical tool is tracked; a second surgical tool is maneuvered according to said at least one output protocol; a second surgical tool is activated; a second surgical tool is deactivated; in a second surgical tool, at least one of a group consisting of an articulation angle, an articulation length and any combination thereof is altered; at least one said endoscope is maneuvered according to an output movement protocol; in at least one said endoscope, at least one of a group consisting of an articulation angle, an articulation length and any combination thereof is altered; at least one said endoscope is zoomed; at least one said endoscope is activated; at least one said endoscope is deactivated; at least a portion of a second endoscope is positioned in a predetermined region of said field of view; at least a portion of of a second endoscope is positioned less than a predetermined distance from an edge of said field of view; a second endoscope is tagged; a second endoscope is tracked; at least a portion of an organ is tagged; at least a portion of a body structure is tagged; a relationship between at least two articles; and any combination thereof.

It is another object of the present invention to disclose the system as described above, wherein said output movement protocol is selected from a group consisting of: moving said at least one surgical tool parallel to the X axis; moving said at least one surgical tool parallel to the Y axis; moving said at least one surgical tool parallel to the Z-axis; rotational movement of said at least one surgical tool around an axis parallel to the X axis; rotational movement of said at least one surgical tool around an axis parallel to the Y axis; rotational movement of said at least one surgical tool around an axis parallel to the Z axis; shaking said at least one surgical tool, moving said at least one surgical tool in at least a portion of a circle, moving said at least one surgical tool in at least a portion of an oval, moving said at least one surgical tool in at least a portion of an ellipse, moving said at least one surgical tool in a straight line, moving said at least one surgical tool in a zigzag, moving said endoscope parallel to the X axis; moving said endoscope parallel to the Y axis; moving said endoscope parallel to the Z-axis; rotational movement of said endoscope around an axis parallel to the X axis; rotational movement of said endoscope around an axis parallel to the Y axis; rotational movement of said endoscope around an axis parallel to the Z axis; shaking said at least one surgical tool, moving said endoscope in at least a portion of a circle, moving said endoscope in at least a portion of an oval, moving said endoscope in at least a portion of an ellipse, moving said endoscope in a straight line, moving said endoscope in a zigzag, an allowed movement, a restricted movement and any combination thereof.

It is another object of the present invention to disclose the system as described above, wherein said output protocol is selected from a group consisting of: said at least one endoscope is maneuvered such that at least one said surgical tool remains within said field of view, said at least one endoscope is maneuvered such that at least one said surgical tool is at a center of said field of view, said at least one endoscope is maneuvered such that at least one said surgical tool is more than a predetermined distance from said edge of said field of view, said at least one endoscope is maneuvered such that at least one said surgical tool is between said edge of said field of view and said predetermined distance from aid edge of said field of view, zoom of said at least one endoscope is altered until said at least one surgical tool at a distance from said edge of said field of view than said predetermined distance from said edge of said field of view and any combination thereof.

It is another object of the present invention to disclose the system as described above, wherein said activation of said at least one surgical tool is selected from a group consisting of: opening said at least one surgical tool, closing said at least one surgical tool, causing said at least one surgical tool to said surgical, stopping said at least one surgical tool from functioning and any combination thereof.

It is another object of the present invention to disclose the system as described above, wherein said relationship is selected from a group consisting of: a predetermined distance between said articles, a predetermined angle between said articles, at least one said article in a predetermined orientation with respect to at least one other said article, a predetermined difference in speed between at least two articles, a predetermined difference in velocity between at least two articles, and any combination thereof.

It is another object of the present invention to disclose the system as described above, wherein said article is selected from a group consisting of: a surgical tool, an endoscope, at least a portion of a tool, at least a portion of an endoscope, at least a portion of a body, at least a portion of an organ, at least a portion of a tissue, at least a portion of an object and any combination thereof, where tissue refers to a structure in the body including, but not limited to, a membrane, a ligament, fat, mesentery, a blood vessel, a nerve, bone, cartilage, a tumor, a cyst and any combination thereof and an object can include a swab, suture thread, a towel, a sponge, a knife blade, a scalpel blade, a pin, a safety pin, a tip, tube, an adapter, a guide such as a cutting guide, a measurement device and any combination thereof.

It is another object of the present invention to disclose a system for providing at least one augmented reality image, comprising: (a) at least one tool; (b) at least one camera located in said tool, configured to real-time provide at least one image of a field of view of said tool; and (c) a computer program which, when executed by data processor, is configured to real time generate a display image by at least one of a group consisting of: (i) generating at least one virtual marker at at least one predetermined position within at least a portion of said image; (ii) rendered superimposing of at least a portion of said image and at least a portion of a second imaging modality image; wherein said superposition or said marking in said image is unaffectable by changes in said display image.

It is another object of the present invention to disclose a method for maneuvering an endoscope, comprising steps of: (a) providing a maneuvering system, comprising: (i) at least one endoscope adapted to real-time provide at least one image of a field of view of the same; (ii) at least one surgical tool; (iii) at least one maneuvering mechanism in active communication with a member of a group consisting of said at least one endoscope, said at least one surgical tool and any combination thereof; said maneuvering mechanism is configured to maneuver in at least two dimensions a member of a group consisting of said at least one endoscope, said at least one surgical tool and any combination thereof; (iv) a computer program which, when executed by a data processor, is in communication with a member of a group consisting of said at least one endoscope, said at least one surgical tool and any combination thereof; said program, when executed by a data processor is configured to (i) real-time image process at least one image; (ii) detect movement of at least a portion of said at least one surgical tool; (b) real-time providing said at least one image of said field of view; (c) real-time image processing said at least one image; (d) real-time detecting movement of said at least a portion of said at least one surgical tool; thereby, if said detected movement of said at least one surgical tool is within a predetermined protocol of input movement, executing at least one of the following steps: (a) maneuvering said endoscope by means of said maneuvering mechanism according to a predetermined protocol of output movement, (b) maneuvering said surgical tool by means of said maneuvering mechanism according to a predetermined protocol of output movement; (c) activating said at least one surgical tool; (d) maneuvering a second surgical tool by means of said maneuvering mechanism according to said at least one output protocol; (e) activating a second surgical tool according to said at least one output protocol; and (f) any combination thereof.

It is another object of the present invention to disclose a method for maneuvering of a surgical tool, comprising steps of: (a) providing a surgical tool maneuvering system, comprising: (i) at least one surgical tool; (ii) at least one endoscope; (iii) at least one maneuvering mechanism in active communication with said at least one surgical tool and said at least one endoscope; said maneuvering mechanism is configured to maneuver at least one selected from a group consisting of said tool, said at least one endoscope and any combination thereof in at least two dimensions; (iv) at least one sensor configured to indicate at least one movement of at least one moving element; said sensor indicates movement of said moving element if a current 3D position or current signal, $3D_{current}$, is substantially different from a previous 3D position or previous signal of the same, $3D_{previous}$; (v) either a wired or wireless communicable database for consecutively storing said $3D_{current}$ and said $3D_{previous}$ of each of said moving element; and (vi) a data processor comprising a computer program in communication with said at least one surgical tool and said at least one maneuvering mechanism; said program, when executed by said data processor is configured to identify if said movement of said moving element is within a predetermined protocol of input movement; (b) indicating said at least one movement of said at least one moving element by means of said sensor; (c) storing said $3D_{current}$ and said $3D_{previous}$ of each of said moving element upon indication of said movement from said sensor; and (d) identifying if said movement of said moving element is within a predetermined protocol of input movement thereby, if said detected movement of said moving element is within said predetermined protocol of input movement movement or said detected position of said moving element is within a predetermined protocol of input positions, maneuvering, by means of said maneuvering mechanism, said member of a group consisting of at least one surgical tool, said at least one endoscope and any combination thereof according to a predetermined protocol of output movement, additionally comprising at least one of the following steps: (a) maneuvering said endoscope by means of said maneuvering mechanism according to a predetermined protocol of output movement; (b) maneuvering said at least one surgical tool by means of said maneuvering mechanism according to a predetermined protocol of output movement; (c) activating said at least one surgical tool; (d) maneuvering a second surgical tool is maneuvered by means of said maneuvering mechanism according to said at least one output protocol; (e) activating a second surgical tool according to said at least one output protocol and, (f) any combination thereof.

It is another object of the present invention to disclose a method for maneuvering an endoscope, comprising steps of: providing a maneuvering system, comprising: (i) at least one endoscope adapted to real-time provide at least one image of a field of view; (ii) at least one surgical tool; (iii) at least one maneuvering mechanism in active communication with at least one selected from a group consisting of said at least one endoscope, said at least one surgical tool and any combination thereof; said maneuvering mechanism is configured to maneuver at least one selected from a group consisting of said at least one endoscope, said at least one surgical tool and any combination thereof; in at least two dimensions; (iv) a computer program which, when executed by a data processor, is in communication with a member of a group consisting of said at least one endoscope, said at least one surgical tool and any combination thereof; said program, when executed by a data processor is configured to identify, from said image of said field of view, an input command; (b) real-time providing said at least one image of said field of view; (c) real-time identifying said input command; thereby, if said input command is within a predetermined protocol of input movement, activating at least one output protocol.

It is another object of the present invention to disclose a method for maneuvering an endoscope, comprising steps of: (a) providing a maneuvering system, comprising (i) at least one surgical tool; (ii) at least one endoscope; (iii) at least one maneuvering mechanism in active communication with said at least one surgical tool and said at least one endoscope; said maneuvering mechanism is configured to maneuver said at least one surgical tool in at least two dimensions; (iv) at least one sensor configured to indicate at least one of position of at least one moving element, movement of at least one moving element, and any combination thereof; (v) said sensor indicates said position of said moving element from a current 3D position or a current signal, $3D_{current}$, and indicates said movement of said moving element if $3D_{current}$ is substantially different from a previous 3D position or a previous signal of the same, $3D_{previous}$; (vi) either a wired or wireless communicable database for consecutively storing said $3D_{current}$ and said $3D_{previous}$ of each of said moving element; and (vii) a data processor comprising a computer program in communication with said at least one surgical tool and said at least one maneuvering mechanism; said program, when executed by said data processor is configured to identify at least one of a group consisting of: said movement of said moving element is within a predetermined input protocol; said position of said moving element is within a predetermined input protocol and any combination thereof; (b) indicating said at least one of position of said at least one moving element, movement of said at least one moving element and any combination thereof by means of said sensor; and (c) identifying if said position of said moving element or said movement of said moving element is within a predetermined input protocol; thereby, if said input command is within a predetermined input protocol, activating at least one output command.

It is another object of the present invention to disclose a method for generating at least one augmented reality image, comprising steps of: (a) providing a system for generating at least one augmented reality image, comprising: (i) at least one tool; (ii) at least one camera located in said tool, configured to real-time provide at least one image of a field of view of said tool; and (iii) a computer program which, when executed by data processor, is configured to real time generate a display image by a member of a group consisting of: (a) generating at least one virtual marker at at least one predetermined position within at least a portion of said image; (b) rendered superimposing of at least a portion of said image and at least a portion of a second imaging modality image and (c) any combination thereof; (b) generating at least one said image of said field of view; and (c) executing said computer program, thereby carrying out a step selected from a group consisting of: (a) generating a virtual marker at at least one predetermined position within at least a portion of said image, (b) generating at least one rendered superposition of at least a portion of said image and at least a portion of a second imaging modality and (c) any combination thereof wherein said superposition or said marking in said image is unaffectable by changes in said display image.

BRIEF DESCRIPTION OF THE DRAWINGS

In order to understand the invention and to see how it may be implemented in practice, a plurality of embodiments will now be described, by way of non-limiting example only, with reference to the accompanying drawings, in which.

DETAILED DESCRIPTION OF THE PREFERRED EMBODIMENTS

Figure 1A:
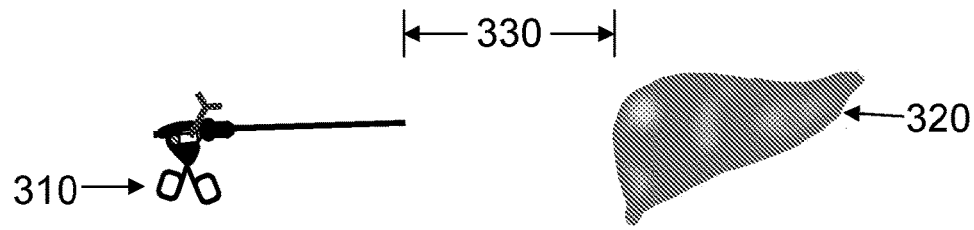
FIG. 1A-D illustrates an embodiment of a collision avoidance function.
Figure 1B:
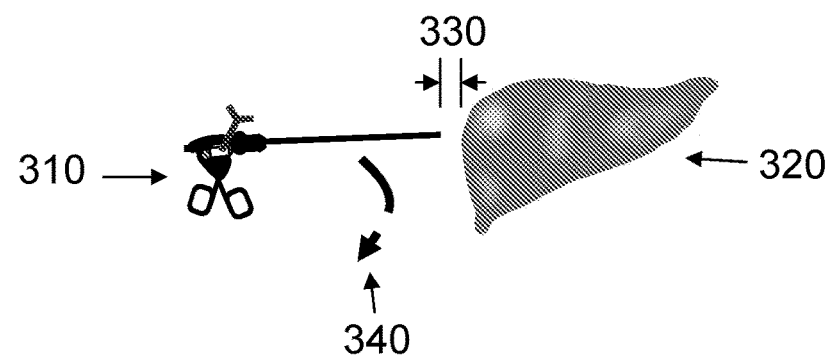

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing augmented reality endoscopic image.

The term 'camera' hereinafter refers to an image acquiring element. Examples of a camera include, but are not limited to, a CCD array and an electromagnetic system such as a TV camera.

The term 'endoscope distal end' hereinafter refers to the end of the endoscope that is inside the patient. The camera is attached to the other side of the endoscope, outside of the patient's abdomen.

The term 'field of view' (FOV) hereinafter refers to the scene visible to the camera.

The term 'display view' hereinafter refers to the scene displayable to an operator.

The term 'structured light' hereinafter refers to a method of producing 3D images using a single 2D camera. In the structured light method, the object is illuminated by a set of rays of light, each ray illuminating a spot on the object from a known position and a known direction, and each ray emitted at a known time. For each known time, a 2D camera image is created from light reflected from the spots created from rays existing at that time. Initially, a known calibration object is illuminated. From the known shape, size and position of the calibration object and from the locations in the camera images of the reflected light, mathematical matrices can be calculated. These matrices enable calculation of the 3D location of the surface of an unknown object, when the unknown object is illuminated by the same set of rays as illuminated the calibration object.

The term 'virtual marker' hereinafter refers to a computer-generated mark, label or other identifier attached to a point or region on the display image. A virtual marker has no physical existence, unlike a tag, wire, or chemical such as luminescent paint physically associated with a portion of the patient.

The terms 'tool' and 'surgical tool' refer herein to any object usable in a medical procedure. A surgical tools can be, but is not limited to, a scalpel, a grasper, a tweezers, a laparoscope, an endoscope, a trocar, a canula, a swab, a tube, a saw, a chisel, a pair of scissors, a pair of shears, a knife, a drill, a rasp, a calipers, a cautery, a curette, a dilator, a Pinzette, a forceps, a clamp, a hook, a lancet, a luxator, a catheter, a holder, an elevator, a probe, a retractor, a spreader, a spatula, a speculum, a needle, a mesh, a spoon, a stapler, a suture, and a tissue expander.

The term 'toggle' refers hereinafter to switching between one tagged surgical tool to another.

The term 'surgical environment' refers hereinafter to any anatomical part within the human body which may be in surrounding a surgical instrument. The environment may comprise: organs, body portions, walls of organs, arteries, veins, nerves, a region of interest, or any other anatomical part of the human body.

The term 'region of interest' refers hereinafter to any region within the human body which may be of interest to the operator of the system of the present invention. The region of interest may be, for example, an organ to be operated on, a restricted area to which approach of a surgical instrument is restricted, a surgical instrument, or any other region within the human body.

The term 'spatial position' refers hereinafter to a predetermined spatial location and/or orientation of an object (e.g., the spatial location of the endoscope, the angular orientation of the endoscope, and any combination thereof).

The term 'prohibited area' refers hereinafter to a predetermined area to which a surgical tool (e.g., an endoscope) is prohibited to be spatially positioned in.

The term 'preferred area' refers hereinafter to predetermined area to which a surgical tool (e.g., an endoscope) is allowed and/or preferred to be spatially positioned in.

The term 'automated assistant' refers hereinafter to any mechanical device (including but not limited to a robotic device) that can maneuver and control the position of a surgical or endoscopic instrument, and that can in addition be configured to receive commands from a remote source.

The term 'tool', 'surgical tool' or 'surgical instrument' refers hereinafter to any instrument or device introducible into the human body. The term may refer to any location on the tool. For example it can refer to the tip of the same, the body of the same and any combination thereof. It should be further pointed that the following description may refer to a surgical tool/instrument as an endoscope.

The term 'provide' refers hereinafter to any process (visual, tactile, or auditory) by which an instrument, computer, controller, or any other mechanical or electronic device can report the results of a calculation or other operation to a human operator.

The term 'automatic' or 'automatically' refers to any process that proceeds without the necessity of direct intervention or action on the part of a human being.

The term 'allowed movement' refers hereinafter to any movement of a surgical tool which is permitted according to a predetermined set of rules.

The term 'restricted movement' refers hereinafter to any movement of a surgical tool which is forbidden according to a predetermined set of rules. For example, one rule, according to the present invention, provides a preferred volume zone rule which defines a favored zone within the surgical environment. Thus, according to the present invention an allowed movement of a surgical tool or the endoscope is a movement which maintains the surgical tool within the favored zone; and a restricted movement of a surgical tool is a movement which extracts (or moves) the surgical tool outside the favored zone.

The term 'time step' refers hereinafter to the working time of the system. At each time step, the system receives data from sensors and commands from operators and processes the data and commands and executes actions. The time step size is the elapsed time between time steps.

The term 'electroencephalographic pattern' or 'brain wave' refers hereinafter to a pattern of electrical impulses of a living brain. Electroencephalographic patterns can be indicative of movement of a portion of the body (the brain is sending a signal to control movement), of intent to move a portion of the body (the brain intends to or is is preparing to send a movement control signal), of an emotional state (worry, fear, pleasure, etc) and any combination thereof. The body portion to be moved can include a limb or portion thereof, an eye, the mouth, throat or vocal cords (speech), the torso or neck, or any other movable portion of the body.

Terms in the singular, such as "a tool" or "an endoscope" can refer to multiple items unless it is clearly stated that there is only one of an object. For example, a reference to "a tool" covers any number of tools.

Laparoscopic surgery, also called minimally invasive surgery (MIS), is a surgical technique in which operations in the abdomen are performed through small incisions (usually 0.5-1.5 cm) as compared to larger incisions of traditional surgical procedures. The key element in laparoscopic surgery is the use of an endoscope, which is a device configured for viewing the scene within the body. Either an imaging device is placed at the end of the endoscope, or a rod lens system or fiber optic bundle is used to direct the image to the proximal end of the endoscope. Also attached is a light source to illuminate the operative field, inserted through a 5 mm or 10 mm cannula or trocar to enable viewing of the operative field.

The abdomen is usually injected with carbon dioxide gas to create a working and viewing space. The abdomen is essentially blown up like a balloon (insufflated), elevating the abdominal wall above the internal organs like a dome. Within this space, various medical procedures can be carried out.

In many cases, other information is available to the operator, such as images from other imaging modalities, such as MRI images or CT scan images. In some cases, it can be desirable to label or tag items in the field of view, such as, for non-limiting example, tools or organs or regions of tissue to be removed.

The device disclosed herein provides a system for maneuvering an endoscope in at least 2 dimensions, where the system is configured to determine input commands, typically of at least one tool in the field of view of an endoscope or of at least one moving element within range of a sensor.

Once an input command is determined, the system activates a predetermined associated output command. The association between input command and output command can be arbitrary (such as, for non-limiting example, shaking a tool to zoom an endoscope) or can be related (such as, for non-limiting example, closing a hand to close a grasper).

Input commands, as described hereinbelow, can comprise (a) predetermined input movement protocols for one or more tools or moving elements, (b) predetermined positions of one or more tools or moving elements, (c) predetermined actions of one or more tools or moving elements, (d) predetermined repositioning of one or more tools or moving elements, and any combination thereof. Any combination of the above can comprise an input command.

Predetermined input movement protocols of a tool or other moving element can include, but are not limited to: shaking the tool or other moving element, moving a tool or other moving element in at least a portion of a circle, moving a tool or other moving element in at least a portion of an oval, moving a tool or other moving element in at least a portion of an ellipse, moving a tool or other moving element in a straight line, moving a tool or other moving element in a zigzag, rotating a tool or other moving element in a predetermined manner, translating a tool or other moving element in a predetermined manner, and any combination thereof.

Predetermined input positions of a tool or other moving element can include but are not limited to positioning the tool or other moving element at a predetermined location within a field of view, orienting the tool or other moving element at a predetermined angle within a field of view, and any combination thereof.

The predetermined location in the field of view can be an edge of the field of view or a predetermined region within the field of view.

Predetermined actions of a tool can include, but are not limited to operating a tool, activating a tool, articulating a tool, articulating an endoscope, zooming an endoscope, and any combination thereof.

Repositioning a tool typically refers to moving a tool from one position or orientation to at least one second position or orientation, where there is a predetermined difference between the first position and/or orientation and the second position and/or orientation. For non-limiting example, repositioning a cautery from the edge of a field of view to the center of the field of view can be associated with a command to turn the cautery on; to turn it off, reposition it from the center of the field of view to the edge.

Output movement commands can include, but are not limited to, a predetermined output movement protocol for at least one tool or at least one endoscope, (b) a predetermined position of at least one tool or at least one endoscope, (c) a predetermined action of of at least one tool or at least one endoscope, (d) a predetermined repositioning of of at least one tool or at least one endoscope, and any combination thereof.

Predetermined output movement protocols for at least one surgical tool or endoscope can include: tracking at least one surgical tool, repositioning at least one surgical tool, repositioning at least one endoscope, zooming at least one endoscope, moving at least one surgical tool in at least a portion of a circle, moving at least one surgical tool in at least a portion of an oval, moving at least one surgical tool in at least a portion of an ellipse, moving at least one surgical tool in a straight line, moving at least one surgical tool in a zigzag, rotating at least one surgical tool in a predetermined manner, translating at least one surgical tool in a predetermined manner, tracking at least one endoscope, repositioning at least one endoscope, repositioning at least one endoscope, zooming at least one endoscope, moving at least one endoscope in at least a portion of a circle, moving at least one endoscope in at least a portion of an oval, moving at least one endoscope in at least a portion of an ellipse, moving at least one endoscope in a straight line, moving at least one endoscope in a zigzag, rotating at least one endoscope in a predetermined manner, translating at least one endoscope in a predetermined manner, and any combination thereof.

Output actions include, but are not limited to: tagging at least one surgical tool, tagging at least one object in a field of view, activating at least one surgical tool, deactivating at least one surgical tool, articulating at least one surgical tool, tagging at least one endoscope, activating at least one endoscope, deactivating at least one endoscope, articulating at least one endoscope, zooming at least one endoscope, and any combination thereof.

Activation of a tool can include, but is not limited to: opening a tool, closing a tool, causing a tool to function (non-limiting examples include heating a cautery or ablator, starting a drill rotating, and starting flow of fluid via a tube or canula), and stopping a tool from functioning.

In some embodiments, the endoscope is configured to provide, in real time, at least one image of its field of view. In such embodiments, the at least one image is analyzed in real time to detect movement of at least one surgical tool or endoscope in the field of view, thereby detecting movement protocols and identifying input commands.

Other non-limiting examples of means of detecting movement protocols in order to identify input commands can be: detecting movement protocols via at least one sensor in range of at least a portion of at least one tool; detecting movement protocols via movement commands for a maneuvering system; detecting movement protocols via a at least one sensor in range of at least a portion of a maneuvering system; identifying movement protocols via a at least one sensor in range of a body part, via sound, via a sensor configured to detect at least one brain signal such as an encephalographic pattern, via a sensor configured to detect at least one muscular signal, such as an electric or magnetic signal associated with muscular movement, via contact with a prepared surface and any combination thereof.

A non-limiting example of an input movement protocol is shaking of a tool tip, and a non-limiting example of an associated output movement protocol is tracking a tool, either the shaken tool or another tool, where "tracking" refers to maneuvering an endoscope so as to retain the tip of the tool in the center of the field of view of the endoscope. Other input and output protocols will be discussed below In some embodiments, the system can maneuver the endoscope in two dimensions; in others, it can maneuver the endoscope in at least 3 dimensions. The dimensions of maneuvering can involve a combination of linear and rotational movement, including zooming. Maneuvering can include both physical maneuvering and virtual maneuvering. Virtual maneuvering occurs when at least one aspect of the image is altered under processor control, rather than by physically moving the endoscope. For example, instead of moving an endoscope closer to an object at the center of the field of view, the processor can execute a virtual zoom, where the processor manipulates a portion of the image so that the display comprises a magnified image of the center of the field of view.

The moving element can be at least a portion of at surgical tool, movement of the distal end of a surgical tool, movement of at least a portion of the body of at least one operator, intended movement of at least a portion of the body of at least one operator, a brain signal from at least one operator, a sound signal and any combination thereof.

Input movement protocols can comprise movement of an object such as a portion of a body of an operator. Non-limiting examples of input movement protocols and exemplary associated output commands include: opening or closing a hand or fingers to command opening or closing a grasper, a pair of scissors or any other openable tool; bending a hand or finger to command a change in the articulation of an endoscope or other articulating tool; and making a first to command that at least a portion of a tool be fixed in a predetermined position, such as its present position. Many other input movement protocols comprising movement of a portion of the body will be obvious.

Non-limiting examples of brain signals include a brain signal indicative of an order to move a portion of the body (e.g., "open the hand"), a brain signal indicative of intention to move a portion of the body (e.g., "the next step will be opening the hand in order to release the grasper from the tissue"), a brain signal indicative of a future development (e.g., "stop that tool!"; "zoom the endoscope outward").

A moving element has moved if its current 3D position, $3D_{current}$, is substantially different from a previous 3D position, $3D_{previous}$; at least one such movement determines a movement protocol. A computer program (as executed by a processor) can identify at least one input movement protocol and, either alone or in conjunction with a member of a group consisting of: an input position, an input reposition an input action and any combination thereof, can determine an input command and its associated output command and can, based on the output command, instruct the maneuvering system to execute the desired output movement protocol.

Input movement protocols are typically arbitrary, predefined movements, although they need not be. A non-limiting example of an arbitrary input movement protocol is a clockwise circle of a tool tip to identify an input command for an inward zoom; the associated output movement protocol can comprise zooming the endoscope to increase magnification in a portion of the field of view. A non-limiting example of a non-arbitrary movement protocol is movement that would bring a tool tip into dangerously close proximity to an organ; the output movement protocol can comprise reducing the speed at which the tool tip moves, stopping movement of the tool tip, changing the direction of movement of the tool tip and any combination thereof.

Other input movement protocols include, but are not limited to, introducing a tool to the surgical environment, removing a tool from the surgical environment, and any combination thereof.

A non-limiting example of closing a tool is closing a grasper to retain a swab in position; an input protocol can be opening of the hand; the output protocol can be opening the grasper and releasing the swab from the grasper. In another example, an input movement protocol of separating the hands indicates that an operator is going to work deeper in the tissue with the resulting output movement protocol of moving retractors to further open an incision. Similarly, an input movement protocol of bringing the hands together can induce an output movement protocol of relaxing retractors so as to allow an incision to at least partially close.

In another non-limiting example, the input protocol comprises the input action of activation of a tool (such as, but not limited to, closing a grasper) with an associated output protocol of zooming the endoscope so that the image of tissue in the neighborhood of the grasper is magnified. A related input protocol can be opening of the grasper, with an associated output protocol of zooming outward to give an overview of the region.

A non-limiting example of an input command comprising a position in a field of view or in a display image is an input command to keep the tip of a tracked tool within a field of view. The output command would comprise a "grey area" extending from the edge of the field of view to a predetermined distance from the field of view. Entry of the tool tip into the grey area activates an output protocol whereby the endoscope is maneuvered to keep the tracked tool tip within the field of view. In some variants, the output protocol comprises maneuvering the endoscope to put the tracked tool tip in the center of the field of view, in other variants, the output protocol comprises maneuvering the endoscope to place the tracked tool tip slightly more than the predetermined distance from the edge, in yet other variants, the output protocol comprises maneuvering the endoscope so as to keep the tracked tool tip in the grey area. In yet other embodiments, the zoom of the endoscope is altered until the tracked tool is outside the grey area. Other variants combine one or more of the above.

Another non-limiting example of an input command comprising a position on a display is a display where placing a tool in a predetermined region of the display activates or deactivates a predetermined output protocol. For instance, moving a tool tip into a region which is at the bottom of the display and just to the left of the center results in an output protocol of zooming inward (magnifying a portion of the image). Moving the tool tip into a region which is at the bottom of the display and just to the right of the center results in an output protocol of zooming outward (demagnifying the image). Regions can include, but are not limited to, a zooming region, a tool tagging region, a region for activating a tagged tool, a region for deactivating a tagged tool, a region rotating the image, a region for moving the center of the field of view, a region for saving or storing an image, a region of augmenting an image, a region comprising an image to be used for an augmentation, a region for moving a tagged tool, and any combination thereof.

In some embodiments, a predetermined input command can result in an output protocol in which an object is tagged, where the tagged object is identified during the input protocol. For non-limiting example assume an input protocol comprising shaking a tool. The output protocol can comprise: (a) identifying the shaken tool as the tagged object, (b) transferring the tagging to a next tool, (c) a first shake transfers tagging to a next tool, with a subsequent shake transferring the tagging to a next-but-one tool, and so on; (d) tagging an object, where the identity of the object determined by a portion of the tool (such as the tip of the tool) being, in a display image, over the object; (e) tagging an object by placing a portion of the tool over a predetermined location on a display such as, for non-limiting example, tagging a liver by placing the tip of the shaken tool over an icon of a liver at the edge of the display. Other variants will be obvious to one skilled in the art.

In another embodiment of an input protocol resulting in an output protocol in which an object is tagged. the input protocol can comprise a pointing finger, associated with an output protocol of tagging the object pointed to in a display image. For non-limiting example, an operator points to the liver in a display. The liver is then tagged, and the endoscope moves so that the liver is centered in the field of view and in the display image. In some variants, the endoscope will zoom so that the liver is entirely within the field of view, with the edges of the liver at or close to the edges of the field of view.

A non-limiting example of an input command comprising more than one input movement protocol is exemplified by an input command to activate closing a grasper. The input command comprises two input movement protocols—a first input movement protocols of pointing a finger and a second input movement protocol of closing a hand. The associated output command will comprise an output action of tagging the grasper and a second output action of closing the grasper.

A protocol, either an input protocol or an output protocol, can comprise a predetermined interaction between at least two articles, where an interaction involves a relationship between the articles. An article can be selected from a group consisting of at least a portion of a tool, at least a portion of an endoscope, at least a portion of a body, at least a portion of an organ, at least a portion of a tissue, at least a portion of an object and any combination thereof, where tissue refers to a structure in the body including, but not limited to, a membrane, a ligament, fat, mesentery, a blood vessel, a nerve, bone, cartilage, a tumor, a cyst and any combination thereof and an object can include a swab, suture thread, a towel, a sponge, a knife blade, a scalpel blade, a pin, a safety pin, a tip, tube, an adapter, a guide such as a cutting guide, a measurement device and any combination thereof.

An interaction involves a relationship between at least two articles, such as a predetermined distance between the articles, a predetermined angle between the articles, at least one article in a predetermined orientation with respect to at least one other article, a predetermined difference in speed between at least two articles, a predetermined difference in velocity and any combination thereof. Two articles are travelling at different speeds if the total distance one travels in a time interval Δt is different from the total distance the other travels in the time interval Δt. Two articles are travelling at different velocities if at least one of the following is true: they are traveling at different speeds, or they are traveling in different directions.

Examples of interactions include, but are not limited to:
Holding two hands at a fixed angle with relation to each other.
Tracking, which typically involves keeping a constant distance between an endoscope and at least one tool.
A suction tube can be kept a constant distance from an ablator, with the longitudinal axis of the tube at a fixed angle relative to the longitudinal axis of the ablator.
A grasper can be closed or kept closed if the distance between at least a portion of the grasper and tissue is smaller than a predetermined distance; similarly, a grasper can be opened if the distance between at least a portion of the grasper and the tissue is greater than a predetermined distance.
If two retractors are closer to tissue than a predetermined amount and closer to each other than a different predetermined amount, maintaining the retractors a fixed distance apart, with the flats of their blades parallel to each other. Optionally, the retractors can be maintained a fixed distance from the tissue. This interaction can be used, for example, to keep an incision in an organ open with minimum stress on the tissue, even if the organ is moved.
A fluid delivery tube and a suction tube can be kept fixed distances (which need not be the same) from a cautery, with a fixed angle between the tip of the fluid delivery tube, the tip of the cautery and the tip of the suction tube. In addition, the longitudinal axes of the tubes can be at fixed angles (which need not be the same) relative to the longitudinal axis of the cautery
The speed with which a tool moves toward an organ can be kept below a maximum.
Many more examples will be obvious to one skilled in the art.

In some embodiments, the system provides an override facility, such that such that an output movement command can be overridden. The override can be vocal, a predetermined movement, a predetermined future movement or a thought indicating at least one predefined future development. The movement or future movement can be movement of a tool, a hand, an eye, an arm, a finger, a chest, a neck, a head, a mouth, a tongue, vocal cords, a leg, a toe, a foot or any combination thereof. An actual movement can be detected by any movement detection means, as described herein. A future movement can be detected by means of muscular electric or magnetic patterns, or from measurable brain signals. An example of an electrical measurement of brain signals is an electroencephalographic pattern. Similarly, an override thought can be detected by means of brain signals.

In some embodiments, the system can identify at least one unwanted movement protocol for at least one moving element. Non-limiting examples of unwanted movement protocols include: involuntary movement of a body part, saccadic movement of an eye, vestibulo-ocular movement of an eye, winking an eye, blinking an eye, tremor of a body part, a tic in a body part, myoclonus of a body part, dystonia, and any combination thereof.

In such embodiments, the preferred response is for the system to ignore the unwanted movement, so that the actual output movement is unaffected by and substantially independent of the unwanted movement. For non-limiting example, in a system where the movement of an endoscope is proportional to movement of an eye, the jerkiness of the actual eye movement, imparted both by saccadic movement and vestibule-ocular movement, will be "programmed out" so that the movement of the endoscope is smooth. Similarly, if eye movement is controlling movement of an endoscope to the right, a quick glance upward will be "programmed out"; the endoscope will not diverge from the direct path to the right.

In another non-limiting example, movement of two retractors is controlled by movement of two arms. During a retraction to further open an incision, the operator suffers a muscular twitch that jerks an arm upward. The jerk is ignored so that the retractors move apart smoothly.

In some embodiments, control of the tools and of maneuvering of the laparoscope does not require physical contact between the operator and either the tools or the laparoscope. In such embodiments, the system of the present invention can be used with the operator and the operating team in the same room as the patient during the operation, or the system of the present invention can be used for remote surgery, with the operator controlling the laparoscope and the tools from a location remote from the patient. For example, controlling maneuvering of the laparoscope image does not require use of a joystick or other object which requires the operator or other user, during the operation, to place his hand in contact with the device and, by those movements, control maneuvering of the laparoscope display.

In preferred embodiments, input movement commands and movement protocols and output movement commands and movement protocols are stored in a database in either wired or wireless communication with a processor and the maneuvering system.

In some embodiments of the system, the system is programmed such that it can add new input movement commands and their associated output movement commands and store the new input and output movement commands in a database. In some embodiments, at least one of new input protocols and new output protocols can be added to at least one database.

In some variants of these embodiments, a database further comprises at least one set of commands linkable to an operator so that, after entering an identifier, the operator can, in some embodiments, customize at least one input command by enterering into the database the member of the group consisting of an input movement protocol, an input action, an input position and an input reposition and any combination thereof comprising the customized input command. The customized input command can be associated with an output command.

In some variants of these embodiments, the operator can also customize output commands by entering into a database the member of the group consisting of an output movement protocol, an output action, an output position and an output reposition and any combination thereof comprising the customized output command. For non-limiting example, an operator can select a movement protocol of a spiral movement away from himself as the input movement command to start a flow of fluid to clean an endoscope's optics. In this example, the operator can select a spiral movement towards himself for the command to stop the flow of fluid.

It should be noted that maneuvering of the laparoscope display can be accomplished by physical maneuvering (physically moving some portion of the laparoscope or the imaging optics), by virtual maneuvering (changing the viewed image by means of computer algorithms that alter the portion of the field of view which is displayed), or by some combination thereof.

Another possible use for the system of the present invention is for study or training. By use of a plurality of display screens, a number of students can observe the operation in real time; the students can be in locations remote from both the patient and the operator. The display view can be marked to assist the students in understanding what is present in the display view. Marking can be done by persons other than the operator; if desired, in some embodiments, the operator need not be aware of marks applied to the display view for study or teaching purposes.

In some embodiments, a system and method is provided for providing augmented reality images of a field of view, where the augmentation can be images provided by another imaging modality, stored images or other stored data, information entered by a user, and any combination thereof.

The field of view can be the field of view of an endoscope or laparoscope, or the field of view of a surgical tool.

In some embodiments, control of maneuvering is via a body-mounted user interface which comprises at least one sensor, the sensor configured to sense at least one parameter associated with body motion, with the body motion directing maneuvering of a displayed image, of the endoscope, of a tool, and any combination thereof.

The sensor or sensors can be placed in conjunction with a body portion of an operator, or can be placed so that a body portion of the operator is within range of the sensor.

A sensor can be, for non-limiting example, an ultrasound sensor, an IR sensor, a heat sensor, a pressure sensor, a current sensor, an accelerometer, a tilt sensor, a movement sensor, a gyroscope, an inertial sensor, a goniometer, a magnetometer, a strain sensor, an electroencephalographic sensor, an electrical sensor, a magnetic sensor, a position sensor configured to determine position of said at least one portion of said human body; a speed sensor configured to determine velocity of said at least one portion of said human body; an accelerometer configured to determine acceleration of said at least one portion of said human body; a camera and image detection software configured to determine at least one of position, velocity and acceleration of said at least one portion of said human body; an RF sensor and RF emitter coupleable to said at least one portion of said human body configured to determine at least one of position, velocity and acceleration of said at least one portion of said human body; a sound sensor and sound emitter coupleable to said at least one portion of said human body configured to determine at least one of position, velocity and acceleration of said at least one portion of said human body; an electroencephalographic sensor configured to determine, from at least one electroencephalographic pattern, at least one parameter associated with at least one of position, velocity and acceleration of said at least one portion of said human body, a sensor configured to determine, from at least one electrical pattern in at least one muscle, at least one parameter associated with at least one of position, velocity and acceleration of said at least one portion of said human body and any combination thereof.

The sensors are preferably MEMS devices.

The sensors are preferably in wireless communication with the data processor controlling maneuvering of the display view.

As a non-limiting example of an embodiment, accelerometers can be comprised in a band encircling the operator's lower arm, thereby sensing movement of arm.

In some embodiments, the sensor or sensors can comprise viewing means, such as, but not limited to a camera, an IR sensor, an ultrasound sensor, a sound sensor, an RF sensor, a heat sensor, an electrical sensor, a magnetic sensor, and any combination thereof. In such sensors, the viewing means senses either movement of the body portion or patterns associated with movement of the body portion. The detectable movement can include speech, which can be detected by a sound sensor.

Other possible sensors include, but are not limited to: a position sensor configured to determine position of said at least one portion of said human body; a speed sensor configured to determine velocity of said at least one portion of said human body; an accelerometer configured to determine acceleration of said at least one portion of said human body; a camera and image detection software configured to determine at least one of position, velocity and acceleration of said at least one portion of said human body; an RF sensor and RF emitter coupleable to said at least one portion of said human body configured to determine at least one of position, velocity and acceleration of said at least one portion of said human body; a sound sensor and sound emitter coupleable to said at least one portion of said human body configured to determine at least one of position, velocity and acceleration of said at least one portion of said human body; an electroencephalographic sensor configured to determine, from at least one electroencephalographic pattern, at least one parameter associated with at least one of position, velocity and acceleration of said at least one portion of said human body, a sensor configured to determine, from at least one electrical pattern in at least one muscle, at least one parameter associated with at least one of position, velocity and acceleration of said at least one portion of said human body and any combination thereof.

Non-limiting examples of body portions whose activity can be sensed by a sensor include at least a portion of any of the following: a finger, a hand, a wrist, a forearm, an elbow, a shoulder, an arm, a toe, a foot, a leg, a neck, a chest, an abdomen, a torso or trunk, a head, an eye, the mouth, the brain, and a face. The sensors can comprise a portion of a glove, a band, a harness or a mask or be mounted on or in a glove, a band, a harness or a mask.

A glove can be fingerless, or can have one or more fingers. It can be hand-length, wrist-length, elbow length, can extend partway up the arm, or can extend all the way up the arm. It can have any combination of length and number of fingers. One or two gloves can be worn; they can comprise any combination of the above features.

Non-limiting examples of bands include elastic bands and non-elastic bands; bands are preferably flexible in order to conform to the surface of the body portion, but portions of the band can be rigid. The band can be continuous or can comprise at least one break. Bands can comprise ties, buckles, or any other closure means or size-adjustment means known in the art. They can be fixed-length or variable-length. The band can be of any desired width, up to one that covers the entire arm and even part of the hand. There can therefore be overlap between what is considered a "glove" and what is considered an "arm-covering band".

Bands can comprise armbands, hand bands, face bands and chest bands. Chest-movement sensors can be comprised in a harness, which can be elastic or non-elastic and which can stretch to fit over the head without need for additional closures, can comprise one or more closures, can comprise one or more length-adjustment mechanisms, and any combination thereof. Closures and length-adjustment mechanisms can be ties, buckles, any other closure mechanism known in the art and any combination thereof.

In some embodiments, the intended movement can be detected encephalographically, via at least one sensor, preferably on the head, configured to determine, from at least one electroencephalographic pattern, at least one parameter associated with at least one of position, velocity and acceleration of at least one portion of a human body. The intended movement can include speech; in this case, the electroencephalographic pattern can be a pattern indicating activity of the brain speech centers.

In some embodiments, the detectable electroencephalographic pattern can include a pattern indicative of alarm or fright. Such a pattern can be used, for non-limiting example, as an override signal.

In some embodiments, at least one electric or magnetic sensor detects electrical and/or magnetic patterns associated with movement of at least one muscle. From these electrical and/or magnetic patterns, the intended movement of the muscle and, therefore, the intended movement of the body portion can be determined and translated into an intended input movement protocol of the surgical tool. The sensor can be remote from the body portion intended to be moved; for example, electrical patterns measured for one or more chest muscles can be used to determine intended movement of an arm and, thence, the desired movement of a surgical tool.

Any combination of the above sensors can be used to maneuver a surgical tool. The tool maneuver can be a maneuver generated by the system in response to a detected movement protocol, a maneuver directly commanded by a user and any combination thereof.

There can be one viewing means per tool, one viewing means can view a plurality of tools, a plurality of viewing means can view one tool, one viewing means can view a plurality of tools, a plurality of viewing means can view a plurality of tools, and any combination thereof.

For non-limiting example, to move the center of the display view towards the right of the display, the operator gestures rightward. An upward gestures zooms the display view outward, shrinking objects in view; a gesture away from the body moves the center of the display view towards the top of the display, and any combination thereof. Other gestures can control returning to a previous view or selecting an object, such as a tool, to be tracked, where following an object means keeping the selected object at the center of the field of view and, if possible, keeping constant its apparent size in the display view.

In another non-limiting example of an embodied gesture, shaking a tool tip selects the tool as the object to be tracked. This informs the system that the shaken tool is to be tracked; it is to be kept in the center of the field of view. A second shake of the tool tip stops tracking. Shaking another tool transfers tracking to the shaken tool.

Another non-limiting example of an embodied gesture is opening and closing the hand to open and close a grasper or bringing the thumb towards a finger to close a grasper and separating the thumb and a finger to open a grasper.

The gesture embodiments described hereinabove can be used in any combination.

Gestures can be combined with, for example, use of a touchscreen or prepared surface. In such embodiments, the operator can touch the image on a screen or other prepared surface to select an object, then execute a gesture to indicate what the object is to do. For non-limiting example, in such an embodiment, in order to retract tissue seen near the top of the screen with a grasper seen near the right side of the screen, the operator touches the image of the grasper to select the grasper and gestures leftward and away from himself. When the tip of the grasper is above the tissue to be retracted, the operator gestures downward and opens his hand, thereby opening the grasper and moving its tip down towards the tissue. When one grasper jaw is above the tissue and one below, a gesture away from himself moves the grasper jaws around the tissue and closure of the hand closes the grasper, grasping the tissue. Another gesture then retracts the tissue. The operator can then touch the image of the grasper again, to stop tracking of the grasper, which fixes the grasper in position.

In a variant of this embodiment, when the grasper is in position, instead of closing his hand, the operator touches a predetermined position on the touchscreen and the grasper closes. The operator can then move a hand, as described above, to reposition the grasper.

Other embodiments of gestures of tool movement and of means of identifying tools will be obvious to one skilled in the art.

In some embodiments, for at least one input movement protocol, the output movement protocol is such that the movement of the tool is proportional to the movement of the body portion, with larger movements of the body portion resulting in proportionally larger movements of the tool. The magnitude of the constant of proportionality can differ for different input movement protocols, The constant of proportionality can be much less than 1, so that relatively large movements of the body portion result in small movements of the tool. The constant of proportionality can be 1, so that the magnitude of the output movement is substantially identical to the magnitude of the movement of the body portion. The constant of proportionality can be greater than 1, so that the magnitude of the output movement is greater than the magnitude of the movement of the body portion.

It is also possible for the magnitude of an output movement to be independent of the magnitude of the movement of the body portion. For non-limiting example, if a movement of a body portion is associated with a command to activate a tool, then the size of the movement is irrelevant; a tool is either active or it is not.

In some embodiments, for at least one input movement protocol, the output movement protocol is such that the movement of the tool is substantially identical to the movement of the body portion.

In some embodiments, for at least one input movement protocol, the output movement protocol is a fixed movement of a tool. For example, an opening movement of the hand, whether large or small, causes a grasper to open fully.

Any combination of proportional movement, identical movement, and fixed movement can be used for the output protocols.

The movement of an endoscope or other surgical tool can be parallel to the X axis; parallel to the Y axis; parallel to the Z-axis; rotation around an axis parallel to the X axis; rotation around an axis parallel to the Y axis; rotation around an axis parallel to the Z axis; and any combination thereof.

In embodiments of the system wherein movement of a surgical tool is controlled by movement of a body portion, whether sensed as movement of the body portion or sensed as movement of a surgical tool, movement of the surgical tool need not be in the same direction as the movement of the body portion. For example, a movement left can translate into movement upward of the surgical tool, rather than moving the body portion upward to move the surgical tool upward. The direction of movement of the surgical tool can be any of: movement of the body portion in a direction parallel to the X axis translates to movement of the surgical tool in a direction parallel to the X axis, movement of the body portion in a direction parallel to the X axis translates to movement of the surgical tool in a direction parallel to the Y axis, movement of the body portion in a direction parallel to the X axis translates to movement of the surgical tool in a direction parallel to the Z axis, movement of the body portion in a direction parallel to the Y axis translates to movement of the surgical tool in a direction parallel to the X axis, movement of the body portion in a direction parallel to the Y axis translates to movement of the surgical tool in a direction parallel to the Y axis, movement of the body portion in a direction parallel to the Y axis translates to movement of the surgical tool in a direction parallel to the Z axis, movement of the body portion in a direction parallel to the Z axis translates to movement of the surgical tool in a direction parallel to the X axis, movement of the body portion in a direction parallel to the Z axis translates to movement of the surgical tool in a direction parallel to the Y axis, movement of the body portion in a direction parallel to the Z axis translates to movement of the surgical tool in a direction parallel to the Z axis, rotation of the body portion about an axis parallel to the X axis translates to rotation of the surgical tool about an axis parallel to the X axis, rotation of the body portion about an axis parallel to the X axis translates to rotation of the surgical tool about an axis parallel to the Y axis, rotation of the body portion about an axis parallel to the X axis translates to rotation of the surgical tool about an axis parallel to the Z axis, rotation of the body portion about an axis parallel to the Y axis translates to rotation of the surgical tool about an axis parallel to the X axis, rotation of the body portion about an axis parallel to the Y axis translates to rotation of the surgical tool about an axis parallel to the Y axis, rotation of the body portion about an axis parallel to the Y axis translates to rotation of the surgical tool about an axis parallel to the Z axis, rotation of the body portion about an axis parallel to the Z axis translates to rotation of the surgical tool about an axis parallel to the X axis, rotation of the body portion about an axis parallel to the Z axis translates to rotation of the surgical tool about an axis parallel to the Y axis, rotation of the body portion about an axis parallel to the Z axis translates to rotation of the surgical tool about an axis parallel to the Z axis, and any combination thereof.

In some embodiments, linear movement of the body portion, whether sensed as movement of the body portion or sensed as movement of a surgical tool, is translated to rotational movements of the endoscope or other surgical tool. For example: movement of the body portion in a direction parallel to the X axis translates to rotation of the surgical tool about an axis parallel to the X axis, movement of the body portion in a direction parallel to the X axis translates to rotation of the surgical tool about an axis parallel to the Y axis, movement of the body portion in a direction parallel to the X axis translates to rotation of the surgical tool about an axis parallel to the Z axis, movement of the body portion in a direction parallel to the Y axis translates to rotation of the surgical tool about an axis parallel to the X axis, movement of the body portion in a direction parallel to the Y axis translates to rotation of the surgical tool about an axis parallel to the Y axis, movement of the body portion in a direction parallel to the Y axis translates to rotation of the surgical tool about an axis parallel to the Z axis, movement of the body portion in a direction parallel to the Z axis translates to rotation of the surgical tool about an axis parallel to the X axis, movement of the body portion in a direction parallel to the Z axis translates to rotation of the surgical tool about an axis parallel to the Y axis, movement of the body portion in a direction parallel to the Z axis translates to rotation of the surgical tool about an axis parallel to the Z axis and any combination thereof.

In some embodiments, rotational movement of the body portion, whether sensed as movement of the body portion or sensed as movement of a surgical tool, is translated to linear movements of the surgical tool. For example: rotation of the body portion about an axis parallel to the X axis translates to movement of the surgical tool in a direction parallel to the X axis, rotation of the body portion about an axis parallel to the X axis translates to movement of the surgical tool in a direction parallel to the Y axis, rotation of the body portion about an axis parallel to the X axis translates to movement of the surgical tool in a direction parallel to the Z axis, rotation of the body portion about an axis parallel to the Z axis translates to movement of the surgical tool in a direction parallel to the X axis, rotation of the body portion about an axis parallel to the Z axis translates to movement of the surgical tool in a direction parallel to the Y axis, rotation of the body portion about an axis parallel to the Z axis translates to movement of the surgical tool in a direction parallel to the Z axis and any combination thereof.

Any combination of the above translations can be used in an embodiment.

In some embodiments, a predetermined output protocol is configured to determine allowed and restricted movements of the endoscope from historical movements of the endoscope according with historical movement patterns of at least one surgical tool in at least one previous surgery. Thus, according to these embodiments, the predetermined protocol comprises a communicable database storing each 3D spatial position of the endoscope according with at least two 3D spatial positions, the current 3D spatial position, $3D_{current}$, and at least one previous 3D spatial position, $3D_{previous}$, of at least one surgical tool, such that each movement pattern of the at least one surgical tool and each 3D position of the endoscope according with the same is stored; the predetermined protocol is configured to determine allowed and restricted movements of the endoscope from the stored movement patterns of the at least one surgical tool and the stored movements of the endoscope, such that the allowed movements of the endoscope are movements in which the endoscope is located substantially in at least one of the endoscope 3D spatial positions according with at least one 3D tool movement pattern, and the restricted movements are movements in which the location of the endoscope is substantially different from the n 3D endoscope spatial positions according with the n movement patterns.

The system further comprises a predetermined set of rules to control movement of the surgical tool. As described hereinbelow, the rules, among other functions, ensure that a surgical tool can be moved without undesired contact with another surgical tool or with a portion of the body. The predetermined set of rules is configured to take into consideration all the possible factors which may be important during the surgical procedure. The predetermined set of rules can comprise any combination of the following rules:
 a. a route rule;
 b. an environment rule;
 c. an operator input rule;
 d. a proximity rule;
 e. a collision prevention rule;
 f. a history based rule;
 g. a tool-dependent allowed and restricted movements rule.
 h. a most used tool rule;
 i. a right tool rule;
 j. a left tool rule;
 k. a field of view rule;
 l. a no fly zone rule;
 m. an operator input rule;
 n. a preferred volume zone rule;
 o. a preferred tool rule;
 p. a movement detection rule, Thus, for example, the collision prevention rule defines a minimum distance below which two or more tools should not be brought together (i.e., there is minimum distance between two or more tools that should be maintained). If the movement of one tool will cause it to come dangerously close to another tool (i.e., the distance between them, after the movement, is smaller than the minimum distance defined by the collision prevention rule), the controller either alerts the user that the movement is a restricted movement or does not permit the movement.

It should be emphasized that all of the above (and the following disclosure) is enabled by constantly monitoring the surgical environment, and identifying and locating the 3D spatial location of each element/tool in the surgical environment.

The identification is provided by conventional means known to any skilled in the art (e.g., image processing, optical means etc.).

The following provides explanations for each of the above mentioned rules and their functions:

According to some embodiments, the route rule comprises a predefined route in which the at least one surgical tool is configured to move within the surgical environment; the allowed movements are movements in which the at least one surgical tool is located within the borders of the predefined route, and the restricted movements are movements in which the at least one surgical tool is located out of the borders of the predefined route. Thus, according to this embodiment, the route rule comprises a communicable database storing at least one predefined route in which the at least one surgical tool is configured to move within the surgical environment; the predefined route comprises n 3D spatial positions of the at least one surgical tool in the route; n is an integer greater than or equal to 2; allowed movements are movements in which the at least one surgical tool is located substantially in at least one of the n 3D spatial positions of the predefined route, and restricted movements are movements in which the location of the at least one surgical tool is substantially different from the n 3D spatial positions of the predefined route.

In other words, according to the route rule, each of the surgical tool's courses (and path in any surgical procedure) is stored in a communicable database. Allowed movements are defined as movements in which the at least one surgical tool is located substantially in at least one of the stored routes; and restricted movements are movements in which the at least one surgical tool is in a substantially different location than any location in any stored route.

According to some embodiments, the environmental rule is configured to determine allowed and restricted movements according to hazards or obstacles in the surgical environment as received from an endoscope or other sensing means. Thus, according to this embodiment, the environmental rule comprises a communicable database; the communicable database is configured to received real-time images of the surgical environment and is configured to perform real-time image processing of the same and to determine the 3D spatial position of hazards or obstacles in the surgical environment; the environmental rule is configured to determine allowed and restricted movements according to hazards or obstacles in the surgical environment, such that restricted movements are movements in which at least one surgical tool is located substantially in at least one of the 3D spatial positions, and allowed movements are movements in which the location of at least one surgical tool is substantially different from the 3D spatial positions.

In other words, according to the environment rule, each element in the surgical environment is identified so as to establish which is a hazard or obstacle (and a path in any surgical procedure) and each hazard and obstacle (and path) is stored in a communicable database. Restricted movements are defined as movements in which the at least one surgical tool is located substantially in the same location as that of the hazards or obstacles; and the allowed movements are movements in which the location of the at least one surgical tool is substantially different from that of all of the hazards or obstacles.

According to other embodiments, hazards and obstacles in the surgical environment are selected from a group consisting of tissues, surgical tools, organs, endoscopes and any combination thereof.

According to some embodiments, the operator input rule is configured to receive an input from the operator of the system regarding the allowed and restricted movements of the at least one surgical tool. Thus, according to this embodiment, the operator input rule comprises a communicable database; the communicable database is configured to receive an input from the operator of the system regarding allowed and restricted movements of the at least one surgical tool.

According to other embodiments, the input comprises n 3D spatial positions; n is an integer greater than or equal to 2; wherein at least one of which is defined as an allowed location and at least one of which is defined as a restricted location, such that the allowed movements are movements in which the at least one surgical tool is located substantially in at least one of the n 3D allowed spatial positions, and the restricted movements are movements in which the location of the at least one surgical tool is substantially different from the n 3D allowed spatial positions.

According to other embodiments, the input comprises at least one rule according to which allowed and restricted movements of the at least one surgical tool are determined, such that the spatial position of the at least one surgical tool is controlled by the controller according to the allowed and restricted movements.

According to other embodiments, the operator input rule can convert an allowed movement to a restricted movement and a restricted movement to an allowed movement.

According to some embodiments, the proximity rule is configured to define a predetermined distance between the at least one surgical tool and at least one another surgical tool;

the allowed movements are movements which are within the range or out of the range of the predetermined distance, and the restricted movements which are out of the range or within the range of the predetermined distance; the allowed movements and the restricted movements are defined according to different ranges. Thus, according to this embodiment, the proximity rule is configured to define a predetermined distance between at least two surgical tools. In a preferred embodiment, the allowed movements are movements which are within the range of the predetermined distance, while the restricted movements which are out of the range of the predetermined distance. In another preferred embodiment, the allowed movements are movements which are out of the range of the predetermined distance, while the restricted movements are within the range of the predetermined distance It should be pointed out that the above mentioned distance can be selected from the following:
 (a) the distance between the tip of the first tool and the tip of the second tool;
 (b) the distance between the body of the first tool and the tip of the second tool;
 (c) the distance between the body of the first tool and the body of the second tool;
 (d) the distance between the tip of the first tool and the body of the second tool; and any combination thereof.

According to another embodiment, the proximity rule is configured to define a predetermined angle between at least three surgical tools; allowed movements are movements which are within the range or out of the range of the predetermined angle, and restricted movements are movements which are out of the range or within the range of the predetermined angle.

According to some embodiments, the collision prevention rule is configured to define a predetermined distance between the at least one surgical tool and an anatomical element within the surgical environment (e.g. tissue, organ, another surgical tool or any combination thereof); the allowed movements are movements which are in a range that is larger than the predetermined distance, and the restricted movements are movements which is in a range that is smaller than the predetermined distance.

According to another embodiment, the anatomical element is selected from a group consisting of tissue, organ, another surgical tool or any combination thereof.

According to some embodiments, the surgical tool is an endoscope. The endoscope is configured to provide real-time images of the surgical environment.

According to some embodiments, the right tool rule is configured to determine the allowed movement of the endoscope according to the movement of a surgical tool in a specified position in relation to the endoscope, preferably positioned to right of the same. According to this rule, the tool which is defined as the right tool is constantly tracked by the endoscope. According to some embodiments, the right tool is defined as the tool positioned to the right of the endoscope; according to other embodiments, any tool can be defined as the right tool. An allowed movement, according to the right tool rule, is a movement in which the endoscope field of view is moved to a location substantially the same as the location of the right tool, thereby tracking the right tool. A restricted movement, according to the right tool rule, is a movement in which the endoscope field of view is moved to a location substantially different from the location of the right tool.

According to some embodiments, the left tool rule is configured to determine the allowed movement of the endoscope according to the movement of a surgical tool in a specified position in relation to the endoscope, preferably positioned to left of the same. According to this rule, the tool which is defined as the left tool is constantly tracked by the endoscope. According to some embodiments, the left tool is defined as the tool positioned to the left of the endoscope; according to other embodiments, any tool can be defined as the left tool. An allowed movement, according to the left tool rule, is a movement in which the endoscope field of view is moved to a location substantially the same as the location of the left tool. A restricted movement, according to the left tool rule, is a movement in which the endoscope field of view is moved to a location substantially different from the location of the left tool.

According to some embodiments, the field of view rule is configured to define a field of view and maintain that field of view. The field of view rule is defined such that if the endoscope is configured to track a predetermined set of tools in a desired field of view, when one of those tools is no longer in the field of view, the rule instructs the endoscope to zoom out so as to reintroduce the tool into the field of view. Thus, according to this embodiment, the field of view rule comprises a communicable database comprising n 3D spatial positions; n is an integer greater than or equal to 2; the combination of all of the n 3D spatial positions provides a predetermined field of view; the field of view rule is configured to determine the allowed movement of the endoscope within the n 3D spatial positions so as to maintain a constant field of view, such that the allowed movements are movements in which the endoscope is located substantially in at least one of the n 3D spatial positions, and the restricted movements are movements in which the location of the endoscope is substantially different from the n 3D spatial positions.

Thus, according to another embodiment of the field of view rule, the field of view rule comprises a communicable database comprising n 3D spatial positions; n is an integer greater than or equal to 2; the combination of all of the n 3D spatial positions provides a predetermined field of view. The field of view rule further comprises a communicable database of m tools and the 3D spatial locations of the same, where m is an integer greater than or equal to 1 and where a tool can be a surgical tool, an anatomical element and any combination thereof. The combination of all of the n 3D spatial positions provides a predetermined field of view. The field of view rule is configured to determine allowed movement of the endoscope such that the m 3D spatial positions of the tools comprise at least one of the n 3D spatial positions of the field of view, and restricted movements are movements in which the 3D spatial position of at least one tool is substantially different from the n 3D spatial positions of the field of view.

According to another embodiment, the preferred volume zone rule comprises a communicable database comprising n 3D spatial positions; n is an integer greater than or equal to 2; the n 3D spatial positions provides the preferred volume zone; the preferred volume zone rule is configured to determine the allowed movement of the endoscope within the n 3D spatial positions and restricted movement of the endoscope outside the n 3D spatial positions, such that the allowed movements are movements in which the endoscope is located substantially in at least one of the n 3D spatial positions, and the restricted movements are movements in which the location of the endoscope is substantially different from the n 3D spatial positions. In other words, the preferred volume zone rule defines a volume of interest (a desired volume of interest), such that an allowed movement, according to the preferred volume zone rule, is a movement in which the endoscope (or any surgical tool) is moved to a location within the defined preferred volume. A restricted movement, according to the preferred volume zone rule, is a movement in which the endoscope (or any surgical tool) is moved to a location outside the defined preferred volume.

According to another embodiment, the preferred tool rule comprises a communicable database, the database stores a preferred tool; the preferred tool rule is configured to determine the allowed movement of the endoscope according to the movement of the preferred tool. In other words, the preferred tool rule defines a preferred tool (i.e., a tool of interest) that the user of the system wishes to track. An allowed movement, according to the preferred tool rule, is a movement in which the endoscope is moved to a location substantially the same as the location of the preferred tool. A restricted movement is a movement in which the endoscope is moved to a location substantially different from the location of the preferred tool. Thus, according to the preferred tool rule the endoscope constantly tracks the preferred tool, such that the field of view, as seen from the endoscope, is constantly the preferred tool. It should be noted that the user may define in the preferred tool rule to constantly track the tip of a preferred tool or alternatively, the user may define the preferred tool rule to constantly track the body or any location on the preferred tool.

According to some embodiments, the no fly zone rule is configured to define a restricted zone into which no tool (or alternatively no predefined tool) is permitted to enter. Thus, according to this embodiment, the no fly zone rule comprises a communicable database comprising n 3D spatial positions; n is an integer greater than or equal to 2; the n 3D spatial positions define a predetermined volume within the surgical environment; the no fly zone rule is configured to determine a restricted movement if the movement is within the no fly zone and an allowed movement if the movement is outside the no fly zone, such that restricted movements are movements in which the at least one surgical tool is located substantially in at least one of the n 3D spatial positions, and the allowed movements are movements in which the location of the at least one surgical tool is substantially different from the n 3D spatial positions.

According to another embodiment, the most used tool function is configured to define (either real-time, during the procedure or prior to the procedure) which tool is the most used tool (i.e., the tool which is moved the most during the procedure) and to instruct the maneuvering subsystem to constantly position the endoscope to track the movement of this tool. Thus, according to this embodiment, the most used tool rule comprises a communicable database counting the number of movements of each of the surgical tools; the most used tool rule is configured to constantly position the endoscope to track the movement of the surgical tool with the largest number of movements. In another embodiment of the most used tool function, the communicable database measures the amount of movement of each of the surgical tools; the most used tool rule is configured to constantly position the endoscope to track the movement of the surgical tool with the largest amount of movement.

According to another embodiment, the system is configured to alert the physician of a restricted movement of at least one surgical tool. The alert can be audio signaling, voice signaling, light signaling, flashing signaling and any combination thereof.

According to another embodiment, an allowed movement is one permitted by the controller and a restricted movement is one denied by the controller.

According to another embodiment, the operator input rule function is configured to receive an input from the operator of the system regarding allowed and restricted movements of the at least one surgical tool. In other words, the operator input rule function receives instructions from the physician as to what can be regarded as allowed movements and what are restricted movements. According to another embodiment, the operator input rule is configured to convert an allowed movement to a restricted movement and a restricted movement to an allowed movement.

According to some embodiments, the history-based rule is configured to determine the allowed and restricted movements according to historical movements of the at least one surgical tool in at least one previous surgery. Thus, according to this embodiment, the history-based rule comprises a communicable database storing each 3D spatial position of each of the surgical tools, such that each movement of each surgical tool is stored; the history-based rule is configured to determine allowed and restricted movements according to historical movements of the at least one surgical tool, such that the allowed movements are movements in which the at least one surgical tool is located substantially in at least one of the 3D spatial positions, and the restricted movements are movements in which the location of the at least one surgical tool is substantially different from the n 3D spatial positions.

According to some embodiments, the tool-dependent allowed and restricted movements rule is configured to determine allowed and restricted movements according to predetermined characteristics of the surgical tool, where the predetermined characteristics of the surgical tool are selected from a group consisting of: physical dimensions, structure, weight, sharpness, and any combination thereof. Thus, according to this embodiment, the tool-dependent allowed and restricted movements rule comprises a communicable database; the communicable database is configured to store predetermined characteristics of at least one of the surgical tools; the tool-dependent allowed and restricted movements rule is configured to determine allowed and restricted movements according to the predetermined characteristics of the surgical tool.

According to another embodiment, the predetermined characteristics of the surgical tool are selected from a group consisting of: physical dimensions, structure, weight, sharpness, and any combination thereof.

According to this embodiment, the user can define, e.g., the structure of the surgical tool he wishes the endoscope to track. Thus, according to the tool-dependent allowed and restricted movements rule the endoscope constantly tracks the surgical tool having the predetermined characteristics as defined by the user.

According to another embodiment of the present invention, the movement detection rule comprises a communicable database comprising the real-time 3D spatial positions of each surgical tool; the movement detection rule is configured to detect movement of at least one surgical tool. When a change in the 3D spatial position of that surgical tool is received, allowed movements are movements in which the endoscope is re-directed to focus on the moving surgical tool.

According to some embodiments, the at least one location estimating means is at least one endoscope configured to acquire real-time images of a surgical environment within the human body for the estimation of the location of at least one surgical tool.

According to another embodiment, the location estimating means comprise at least one selected from a group consisting of optical imaging means, radio frequency transmitting and receiving means, at least one mark on at least one surgical tool and any combination thereof.

According to another embodiment, the at least one location estimating means is an interface subsystem between a operator and at least one surgical tool, the interface subsystem comprising (a) at least one array comprising N regular light sources or N pattern light sources, where N is a positive integer; (b) at least one array comprising M cameras, where M is a positive integer; (c) optional optical markers and means for attaching the optical markers to at least one surgical tool; and (d) a computerized algorithm operable via the controller, the computerized algorithm configured to record images received by each camera of each of the M cameras and to calculate therefrom the position of each of the tools, and further configured to provide automatically the results of the calculation to the human operator of the interface.

In some embodiments of the system, the faster the body portion is moved, the faster the selected portion of the surgical tool moves. In these embodiments, the system provides a warning if the speed is above a predetermined maximum. Examples of the method of warning include, but are not limited to, a constant volume tone, a constant pitch tone, a varying volume tone, a varying pitch tone, a vocal signal, a constant color visual signal, a constant brightness visual signal, a varying color visual signal, a varying brightness visual signal, a signal visible on at least some part of the endoscope image, a signal visible on at least some portion of the patient, a signal visible in at least some portion of the surroundings of the patient, a vibration in the control unit, a temperature change in the control unit, and any combination of the above.

According to some embodiments of the present invention, the velocity of the surgical tool's movement will be adjusted as a function of the distance of the tool tip from the organ\tissue. For non-limiting example, the closer the tip of an endoscope is to an organ, the slower the endoscope moves, thereby, on the one hand, helping ensure that the endoscope tip stops in a desired position and, on the other hand, reducing the probability that the endoscope will contact the organ/tissue, either through overshoot or through a miscalculation such as could occur from drift in the system.

In some embodiments, the display comprises augmented reality elements.

In some embodiments, the operator can mark a point or points in the body. These points can indicate an organ or tissue, be a location on an organ or tissue, be a location within the body not on an organ or tissue, indicate a tool or other object (such as a swab) introduced by the operator, or be a location (such as a tool tip) on a tool or other object.

Sets of points, such as but not limited to a set of points forming the outline of an object or the surface of an object can also be marked. A non-limiting example of an outline would be a line indicating the approximate extent of a tumor.

Marking can be by means of touching the point on a touchscreen or other prepared surface, touching the position of the point in a 3D display, touching a symbol representing the object on a touchscreen or prepared surface, directing an indicator to the point by means of gestures or predetermined sounds, any other means known in the art of specifying a desired point, and any combination thereof.

After marking, the point can be labeled; the point is indicated in the image by a virtual marker. The virtual marker can comprise any means of labeling images known in the art. Non-limiting examples of virtual markers include a predetermined geometrical shape, a predetermined word, a line encircling the image of a selected object, highlighting of the selected object (placing a patch of predetermined color or predetermined texture), and any combination thereof. Color-coding, with different colors indicating different types of virtual marker, can be used, either alone or in combination with any of the virtual markers described above.

In some embodiments, the virtual marker indicates a selectable display view. In such embodiments, selection of the marker automatically alters the display view to the view specified by the marker. Such selectable display view markers can comprise, for non-limiting example, an outline of the selectable view, a point at the center of the selectable view, a patch or different color or texture covering the selectable view, and any combination thereof.

In some embodiments, portions of the image are enhanced, typically in order to be seen or identified more easily. Objects which can be enhanced include, but are not limited to, blood vessels, organs, ligaments, limbs and any combination thereof.

Enhancement can include, but is not limited to, increasing brightness, altering color, applying color or texture patches, and any combination thereof.

Markers can comprise a distance or angle measurement. For non-limiting example, the user can select two points within the display field and instruct the system to measure the distance between the points. A marker then indicates the two points and the distance between them. Similarly, for non-limiting example, selection of three points instructs the system to measure the angle formed by the three points and to provide a marker showing the points and the angle they form. Any distance or angle measurement known in the art, such as, but not limited to, those typically found in Computer Aided Design (CAD) systems can be implemented the system of the present invention. Distances and angles measurements are 3D measurements. The distance marker will typically be labeled with the total distance between the start and end points. In some embodiments, the distance marker can give the distance between the end points as a triple of values, typically the three distances (x, y, z) of a Euclidean coordinate system. Other typical coordinate systems include, but are not limited to, cylindrical coordinate systems (r, θ, z) and spherical coordinate systems (r, θ, φ).

In some embodiments, orientation marking is provided. The orientation marker indicates a direction fixed relative to the region of interest. Therefore, the operator can remain aware of the orientation of the display view relative to the region of interest in the body, whatever the relative orientations of the body and the display view.

In preferred embodiments, the orientation marker remains within a fixed region in the display view. A non-limiting example of an orientation marker is axes of a 3D coordinate system, with the axes labeled so that the identity of each axis is discernable at a glance. The axes are in a corner of the display view and rotate as the orientation of the display view changes.

Another embodiment of an orientation marker comprises an arrow with a fixed center, the direction of the arrow indicating a fixed (3D) direction in space. The point of the arrow will rotate around the center as the display view changes, while the color or texture of the arrow indicates whether the fixed direction is above or below the plane of the display image and the length of the arrow indicates the angle between the fixed direction and the plane of the display view.

Any orientation marker known in the art can be used.

In some embodiments, the display image combines the laparoscope image with an image from at least one other imaging modality. The other imaging modality can be any imaging modality known in the art, for non-limiting example, CT, MRI, PET, ultrasound, IR imaging, heat imaging, a still camera, a videocamera, image-generation software, image-manipulation software, display of stored images, and any combination thereof. In preferred embodiments, all images are registered so that like portions correspond with each other and so appear to be viewed from the same distance and angle. For non-limiting example, the boundaries of the liver from an MRI scan would overlap the boundaries of the liver from the laparoscope image.

The images from the second imaging modality can be 2D images, 3D images and any combination thereof.

An image from another imaging modality can be a real-time image or can be a stored image. For non-limiting example, the interior of the abdomen can be simultaneously imaged by ultrasound and by the laparoscope during a procedure, with the images from the two modalities registered and displayed simultaneously.

In another non-limiting example, 3D MRI images of the abdomen can be made prior to the procedure. During the procedure, the stored MRI images are registered with 3D structured light images from the laparoscope, providing the operator with an enhanced 3D view, in which the visibility of blood vessels and of tumors has been increased.

In some embodiments, the laparoscope optics comprise at least one wide-angle lens, so that the field of view of the camera comprises substantially all of the region of interest, the portion of the body being worked on or examined. For non-limiting example, for an abdominal operation, the field of view would be substantially all of the interior of the abdomen.

The wide-angle lens can be selected from a group consisting of: a fish-eye lens, an omnidirectional lens, any other conventional wide-angle lens and any combination thereof.

In some embodiments, the display provides a 3D view of the region of interest. In preferred embodiments, structured light is used to provide the 3D view.

The structured slight method produces 3D images using a single 2D camera. In the structured light method, the object is illuminated by a set of rays of light, each ray illuminating a spot on the object from a known position and a known direction, and each ray emitted at a known time. For each known time, a 2D camera image is created from light reflected from the spots created from rays existing at that time. Initially, a known calibration object is illuminated. From the known shape, size and position of the calibration object and from the locations in the camera images of the reflected light, mathematical matrices can be calculated. These matrices enable calculation of the 3D location of the surface of an unknown object, when the unknown object is illuminated by the same set of rays as illuminated the calibration object.

In preferred embodiments, the system comprises software for fog removal. Any fog removal technique known in the art can be used. Typical fog removal algorithms comprise, but are not limited to, adjustment of brightness and contrast to compensate for the fog; estimating the fog density pixel by pixel and removing it; estimating an overall fog density and removing the overall fog density from each pixel; estimating the fog density at the deepest point in the image, scaling the fog density by the estimated distance to the object, and removing the scaled density from the pixel, and any combination thereof.

EXAMPLES

Examples are given in order to prove the embodiments claimed in the present invention. The example, which is a clinical test, describes the manner and process of the present invention and set forth the best mode contemplated by the inventors for carrying out the invention, but are not to be construed as limiting the invention.

In the examples below, similar numbers refer to similar parts in all of the figures.

Example 1—Tracking System with Collision Avoidance System

One embodiment of such a rule-based system will comprise the following set of commands:
Detection (denoted by Gd):
  $Gd_1$ Tool location detection function
  $Gd_2$ Organ (e.g. Liver) detection function
  $Gd_3$ Movement (vector) calculation and estimation function
  $Gd_4$ Collision probability detection function
Tool Instructions (denoted Gt):
  $Gt_1$ Move according to manual command
  $Gt_2$ Stop movement
The scenario—manual move command by the operator:
Locations $Gd_1(t)$ and $Gd_2(t)$ are calculated in real time at each time step (from an image or location marker).

Tool movement vector $Gd_3(t)$ is calculated from $Gd_1(t)$ as the difference between the current location and at least one previous location (probably also taking into account previous movement vectors).

The probability of collision—$Gd_1(t)$—is calculated, for example, from the difference between location $Gd_1$ and location $Gd_2$ (the smaller the distance, the closer the proximity and the higher the probability of collision), from movement vector $Gd_3(t)$ indicating a collision, etc.

Tool Instructions $Gt_1$ Weight function $\alpha_1(t)=1$ if $Gt_1$ (t)<a predetermined threshold and 0 otherwise Tool Instructions $Gt_2$ Weight function $\alpha_2(t)=1$ if $Gt_2$ (t)>a predetermined threshold and 0 otherwise Tool Instructions=$\alpha_1(t)*Gt_1+\alpha_2(t)*Gt_2(t)$;

In reference to FIG. 1, which shows, in a non-limiting manner, an embodiment of a tracking system and collision avoidance system. The system tracks a tool 310 and the liver 320, in order to determine whether a collision between the tool 310 and the liver 320 is possible within the next time step. FIGS. 1a and 1b show how the behavior of the system depends on the distance 330 between the tool 310 and the liver 320, while FIGS. 1c and 1d show how movement of the tool 310 affects the behavior. In FIG. 1a, the distance 330 between the tool 310 and the liver 320 is large enough that a collision is not possible in that time step. Since no collision is possible, no movement of the tool is commanded. In FIG. 1b, the distance 330 between the tool 310 and the liver 320 is small enough that a collision is likely. In the embodiment illustrated, a movement 340 is commanded to move the tool 310 away from the liver 320. In other embodiments, the system prevents movement 350, but does not command movement 340; in such embodiments, the tool 310 will remain close to the liver 320. In yet other embodiments, the system warns/signals the operator that the move is restricted, but does not restrict movement 350 or command movement 340 away from the liver. Such a warning/signaling can be visual or aural, using any of the methods known in the art.

Figure 1C:
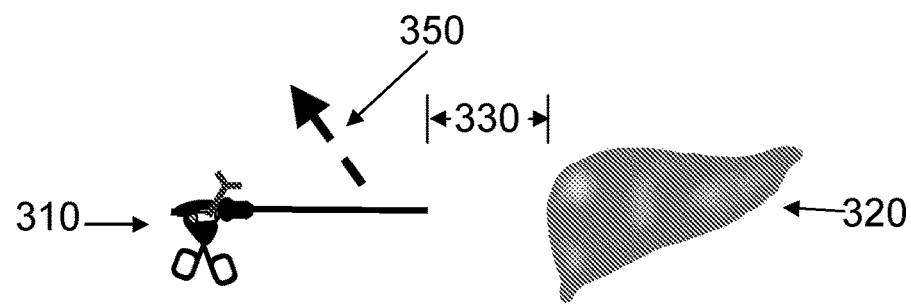
Figure 1D:
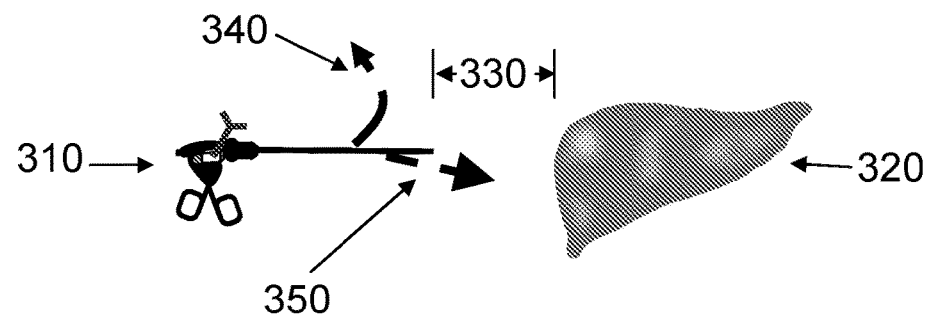

FIGS. 1c and 1d illustrate schematically the effect of the movement of tool 310 on the collision avoidance system. In FIGS. 1c and 1d, the tool 310 is close enough to the liver 320 that a collision between the two is possible. If the system tracked only the positions of the tool 310 and the liver 320, then motion of the tool 310 away from the liver 320 would be commanded. FIG. 1c illustrates the effect of a movement 350 that would increase the distance between tool 310 and liver 320. Since the movement 350 is away from liver 320, no collision is possible in this time step and no movement of the tool 310 is commanded.

In FIG. 1d, tool 310 is the same distance from liver 320 as in FIG. 1c. However, in FIG. 1d, the movement 350 of the tool 310 is toward the liver 320, making a collision between tool 310 and liver 320 possible. In some embodiments, a movement 340 is commanded to move the tool 310 away from the liver 320. In other embodiments, the system prevents movement 350, but does not command movement 340; in this embodiment the tool 310 will remain close to the liver 320. In yet other embodiments, the system warns the operator that move is restricted, but does not restrict movement 350 or command movement 340 away from the liver. Such a warning can be visual or aural, using any of the methods known in the art.

As a non-limiting example, in an operation on the liver, the collision detection function can warn the operator that a collision between a tool and the liver is likely but not prevent the collision. In an operation on the gall bladder, the collision detection function can prevent a collision between the tool and the liver, either by preventing the movement or by commanding a movement redirecting the tool away from the liver, Example 2—Tracking System with Soft Control—Fast Movement when Nothing is Nearby, Slow Movement when Something is Close One embodiment of such rule-based system comprises the following set of commands:
Detection (denoted by Gd):
Main Tool location detection function (denoted by GdM);
Gd-tool$_1$-K—Tool location detection function;
Gd-organ$_2$-L—Organ (e.g. Liver) detection function;
Gd$_3$ Main Tool Movement (vector) calculation and estimation function;
Gd$_4$ Proximity probability detection function;
Tool Instructions (denoted Gt):
Gt$_1$ Movement vector (direction and speed) according to manual command
The scenario—manual move command by the operator:
Locations GdM(t), Gd-tool$_1$-K(t) and Gd-organ$_2$-L(t) are calculated in real time at each time step (from image or location marker).
Main Tool Movement Vector Gd$_3$(t) is calculated per GdM (t) as the difference between the current location and at least one previous location (probably also taking into account previous movement vectors)
The proximity of the main tool to other tools—Gd$_4$(t)—is calculated, for example, as the smallest of the differences between the main tool location and the other tools' locations.
Tool Instructions Gt$_1$ Weight function $\alpha_1$(t) is proportional to tool proximity function Gd$_4$(t), the closer the tool the slower the movement so that, for example $$\alpha_2(t)=Gd_4/\text{maximum}(Gd_4)$$

or $$\alpha_2(t)=\log(Gd_4/\text{maximum}(Gd_4))$$

where maximum(Gd$_4$) is the maximum distance which is likely to result in a collision given the distances, the speed of the tool and the movement vector.

$$\text{Tool Instructions}=\alpha_1(t)*Gt_1.$$

Example 3—Tracking System with No-Fly Rule/Function

In reference to FIG. 2, which shows, in a non-limiting manner, an embodiment of a tracking system with no-fly rule. The system tracks a tool 310 with respect to a no-fly zone (460), in order to determine whether the tool will enter the no-fly zone (460) within the next time step. In this example, the no-fly zone 460 surrounds the liver.

Figure 2A:
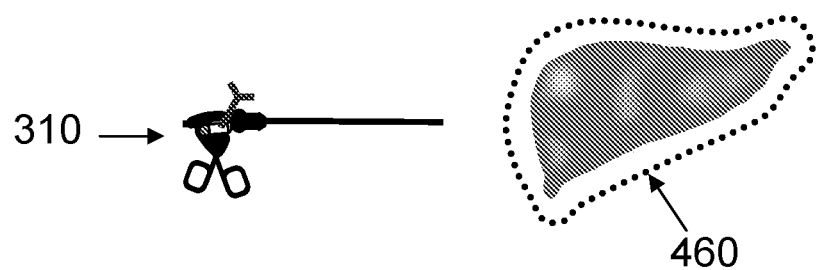
FIG. 2A-D illustrates an embodiment of a no-fly zone function.
Figure 2B:
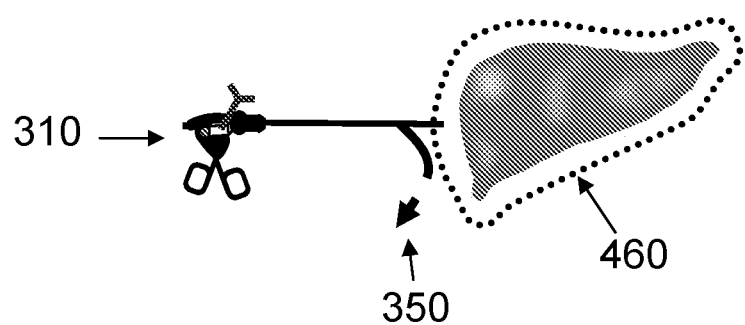
Figure 2C:
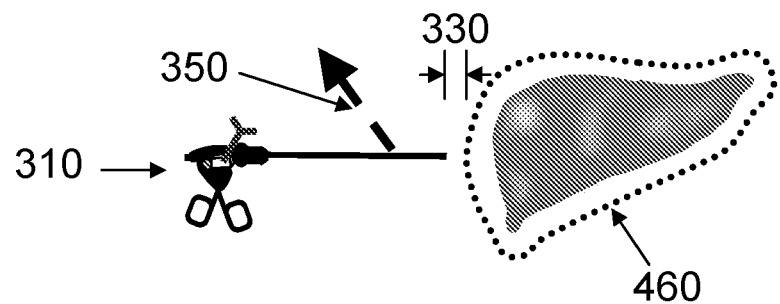
Figure 2D:
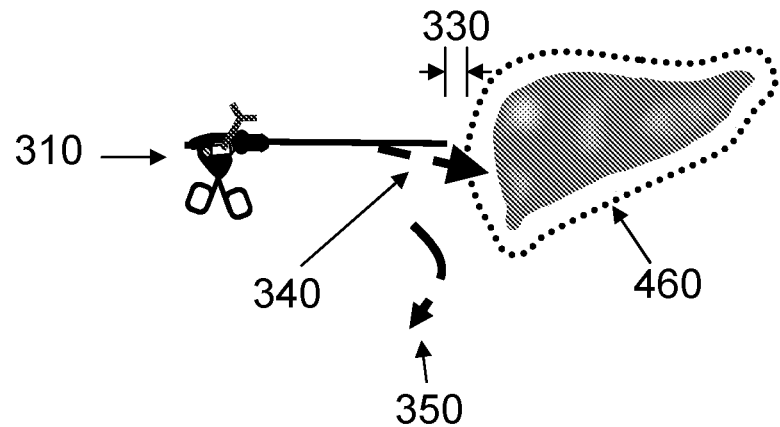

FIGS. 2a and 2b show how the behavior of the system depends on the location of the tool tip with respect to the no-fly zone, while FIGS. 2c and 2d show how movement of the tool affects the behavior.

In FIG. 2a, the tool 310 is outside the no-fly zone rule/function 460 and no movement of the tool is commanded. In FIG. 2b, the tool 310 is inside the no-fly zone 460.

The no-fly zone rule/function performs as follows:
In the embodiment illustrated, a movement 350 is commanded to move the tool 310 away from the no-fly zone 460. In other embodiments, the system prevents movement further into the no-fly zone (refers as movement 340, see FIG. 2c), but does not command movement 340; in such embodiments, the tool 310 will remain close to the no-fly zone 460.

In yet other embodiments, the system warns/signals the operator that the move is restricted, but does not restrict movement further into the no-fly zone or command movement 340 away from the no-fly zone 460. Such a warning/signaling can be visual or aural, using any of the methods known in the art.

FIGS. 2c and 2d illustrate schematically the effect of the tool's movement on operation of the no-fly zone rule/function. In FIGS. 2c and 2d, the tool 310 is close enough to the no-fly zone 460 (distance 330 is small enough) that it is possible for the tool to enter the no-fly zone during the next time step. FIG. 2c illustrates the effect of a movement 340 that would increase the distance between tool 310 and no-fly zone 460. Since the movement 340 is away from no-fly zone 460, no collision is possible in this time step and no movement of the tool 310 is commanded.

In FIG. 2d, tool 310 is the same distance from no-fly zone 460 as in FIG. 2c. However, in FIG. 2d, the movement 340 of the tool is toward no-fly zone 460, making it possible for tool 310 to enter no-fly zone 460. In the embodiment illustrated, a movement 350 is commanded to move the tool 310 away from the no-fly zone 460. In other embodiments, the system prevents movement 340, but does not command movement 350; in such embodiments, the tool 310 will remain close to the no-fly zone 460. In yet other embodiments, the system warns/signals the operator that the move is restricted, but does not restrict movement 340 or command movement 350 away from the no-fly zone rule/function 460. Such a warning/signaling can be visual or aural, using any of the methods known in the art.

Example 4—Tracking System with Preferred Volume Zone Rule/Function

In reference to FIG. 3, which shows, in a non-limiting manner, an embodiment of a tracking system with a preferred volume zone function/rule.
The system tracks a tool 310 with respect to a preferred volume zone (570), in order to determine whether the tool will leave the preferred volume (570) within the next time step.

Figure 3A:
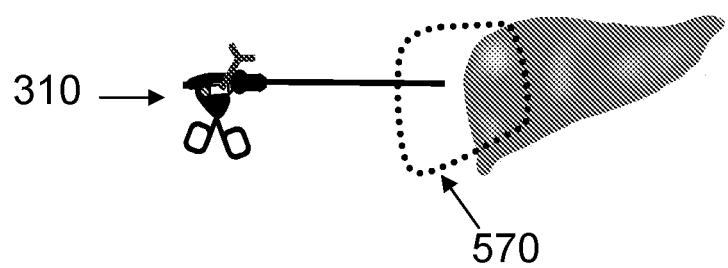
FIG. 3A-D illustrates an embodiment of a preferred volume zone function.
Figure 3B:
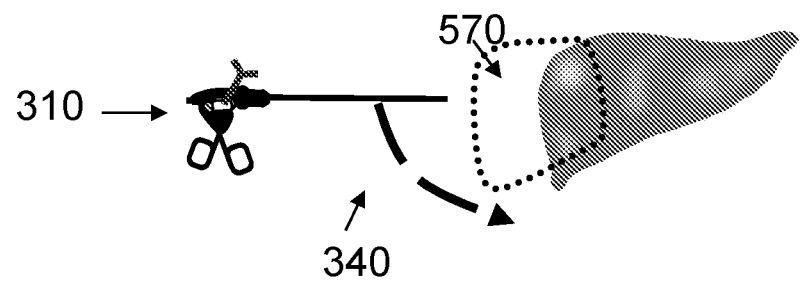

In this example, the preferred volume zone 570 extends over the right lobe of the liver. FIGS. 3a and 3b show how the behavior of the system depends on the location of the tool tip with respect to the preferred volume zone 570, while FIGS. 3c and 3d show how movement of the tool affects the behavior (i.e., the preferred volume zone rule/function).

In FIG. 3a, the tool 310 is inside the preferred volume zone 570 and no movement of the tool is commanded. In FIG. 3b, the tool 310 is outside the preferred volume zone 570.

In the embodiment illustrated, a movement 340 is commanded to move the tool 310 away from the preferred volume zone 570. In other embodiments, the system prevents movement 340; in such embodiments, the tool 310 will remain close to the preferred volume zone 570. In yet other embodiments, the system warns/signals the operator that the move 340 is restricted. Such a warning/signaling can be visual or aural, using any of the methods known in the art.

Figure 3C:
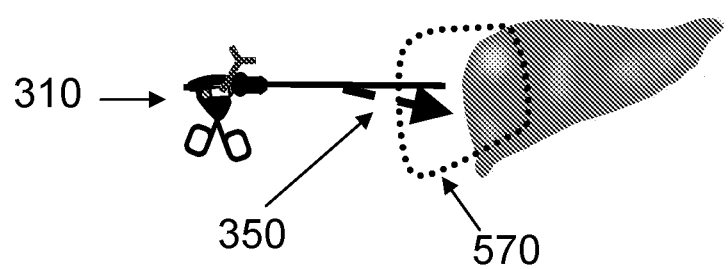
Figure 3D:
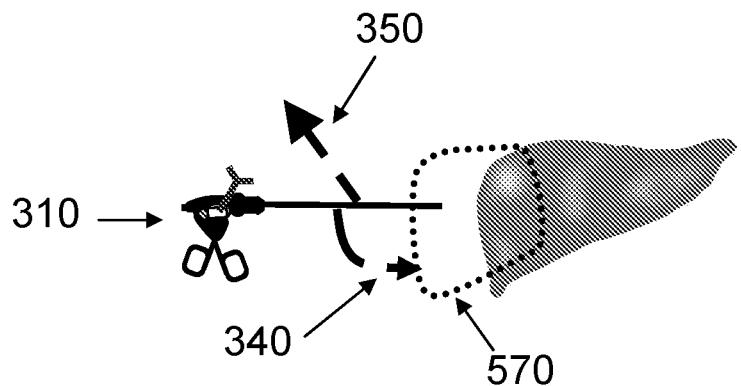

FIGS. 3c and 3d illustrate schematically the effect of the tool's movement on operation of the preferred volume rule/function. In FIGS. 3c and 3d, the tool 310 is close enough to the edge of preferred volume zone 570 that it is possible for the tool to leave the preferred volume zone during the next time step.

FIG. 3c illustrates the effect of a movement 350 that would take the tool 310 deeper into preferred volume zone 570. Since the movement 350 is into preferred volume 570, the movement is an allowed movement.

In FIG. 3d, the movement 350 of the tool is out of the preferred volume 570, making it possible for tool 310 to leave preferred volume 570.

According to one embodiment illustrated, a movement 340 is commanded to move the tool 310 into the preferred volume zone 570. In other embodiments, the system prevents movement 350, but does not command movement 340; in such embodiments, the tool 310 will remain close to the preferred volume zone 570. In yet other embodiments, the system warns/signals the operator that the move is restricted, but does not restrict movement 350 or command movement 340 away from the preferred volume zone 570. Such a warning/signaling can be visual or aural, using any of the methods known in the art.

Example 5—Organ/Tool Detection Function

Figure 4:
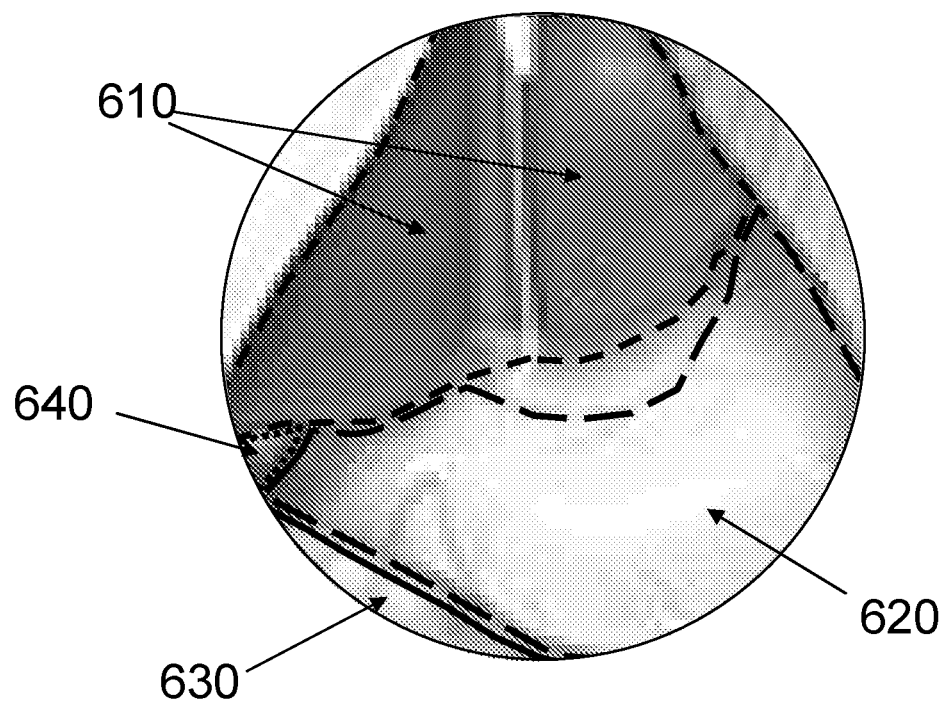
FIG. 4 illustrates an embodiment of an organ detection function.

In reference to FIG. 4, which shows, in a non-limiting manner, an embodiment of an organ detection system (however, it should be noted that the same is provided for detection of tools, instead of organs).

For each organ, the 3D spatial positions of the organs stored in a database. In FIG. 4, the perimeter of each organ is marked, to indicate the edge of the volume of 3D spatial locations stored in the database.

In FIG. 4, the liver 610 is labeled with a dashed line. The stomach 620 is labeled with a long-dashed line, the intestine 630 with a solid line and the gall bladder 640 is labeled with a dotted line.

In some embodiments, a label or tag visible to the operator is also presented. Any method of displaying identifying markers known in the art can be used. For non-limiting example, in an enhanced display, colored or patterned markers can indicate the locations of the organs, with the marker either indicating the perimeter of the organ or the area of the display in which it appears.

Example 6—Tool Detection Function

Figure 5:
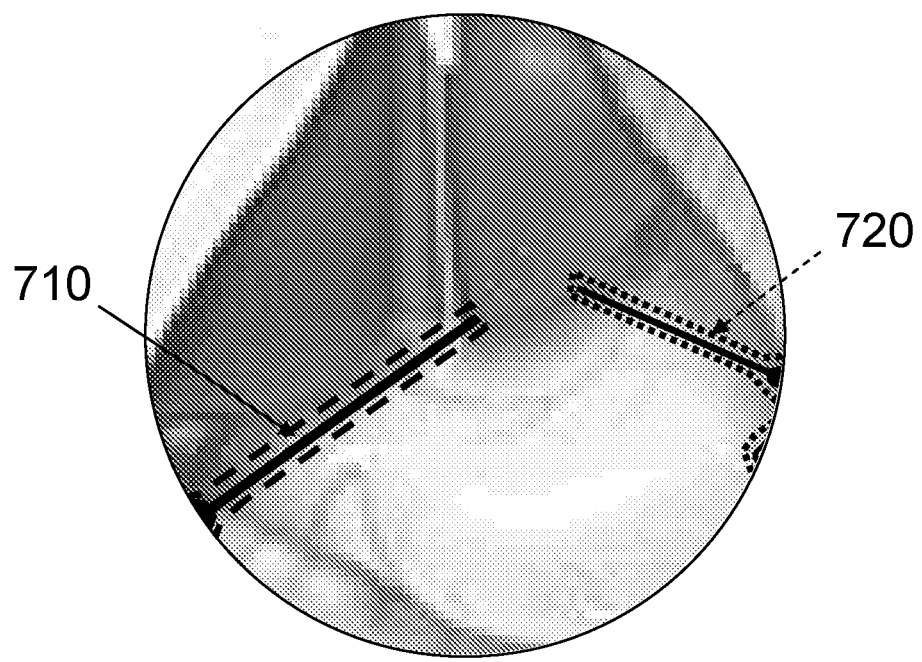
FIG. 5 illustrates an embodiment of a tool detection function.

In reference to FIG. 5, which shows, in a non-limiting manner, an embodiment of a tool detection function. For each tool, the 3D spatial positions of the tools stored in a database. In FIG. 5, the perimeter of each tool is marked, to indicate the edge of the volume of 3D spatial locations stored in the database. In FIG. 5, the left tool is labeled with a dashed line while the right tool is labeled with a dotted line.

In some embodiments, a label or tag visible to the operator is also presented. Any method of displaying identifying markers known in the art can be used. For non-limiting example, in an enhanced display, colored or patterned markers can indicate the locations of the tools, with the marker either indicating the perimeter of the tool or the area of the display in which it appears.

Example 7—Movement Detection Function/Rule

Figure 6A:
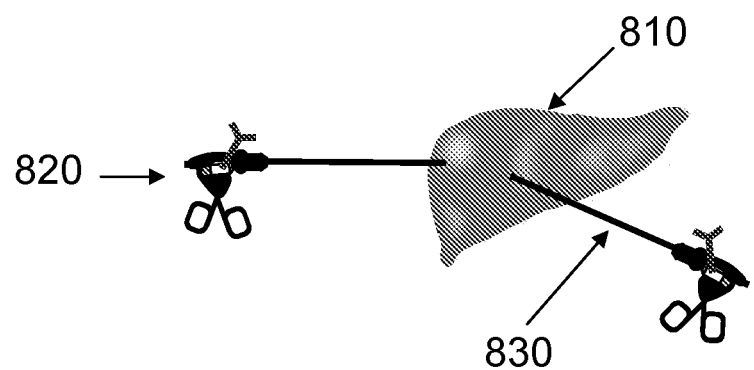
FIG. 6A-B illustrates an embodiment of a movement detection function.
Figure 6B:
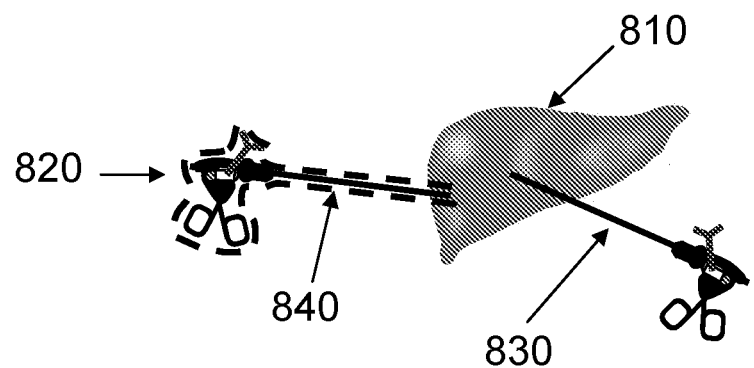

In reference to FIG. 6, which shows, in a non-limiting manner, an embodiment of a movement detection function/rule. FIG. 6a schematically illustrates a liver 810, a left tool 820 and a right tool 830 at a time t. FIG. 6b schematically illustrates the liver 810, left tool 820 and right tool 830 at a later time t+Δt, where Δt is a small time interval. In this example, the left tool 820 has moved downward (towards the direction of liver 810) in the time interval Δt.

The system has detected movement of left tool 820 and labels it. This is illustrated schematically in FIG. 6b by a dashed line around left tool 820.

Example 8—Prediction Function

In reference to FIG. 7, which shows, in a non-limiting manner, an embodiment of the above discussed prediction function.

Figure 7A:
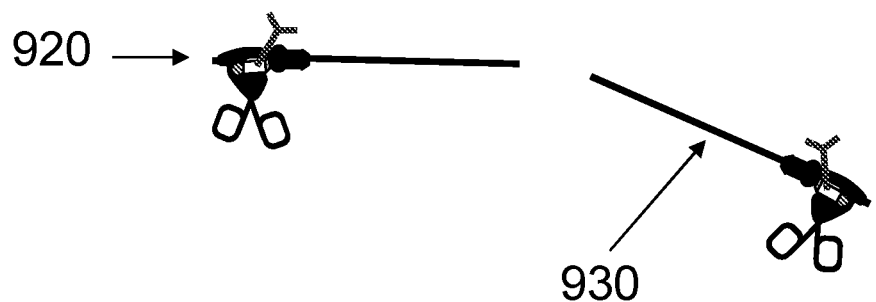
FIG. 7A-D illustrates an embodiment of a prediction function.

FIG. 7a shows a left tool 920 and a right tool 930 at a time t.

Figure 7B:
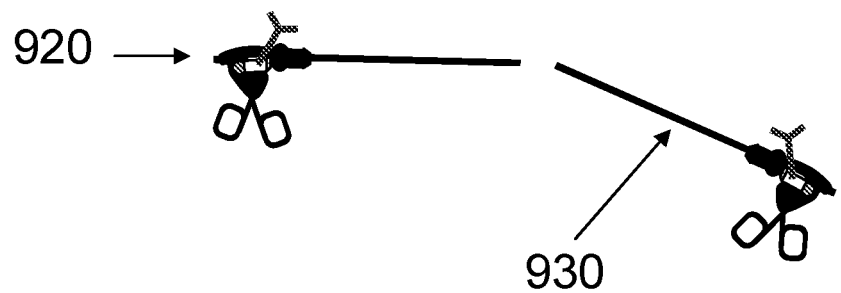
Figure 7C:
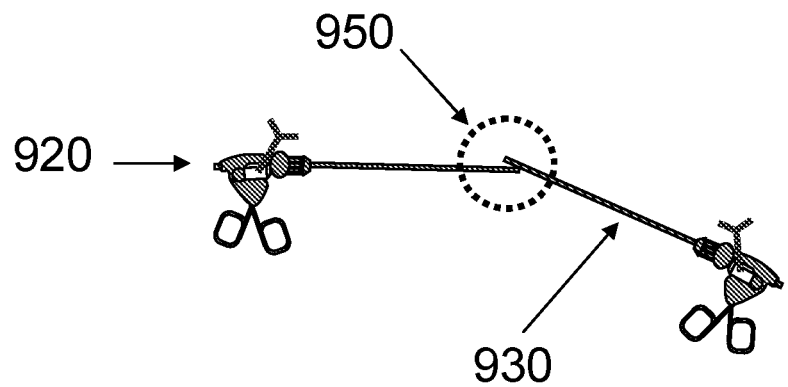
Figure 7D:
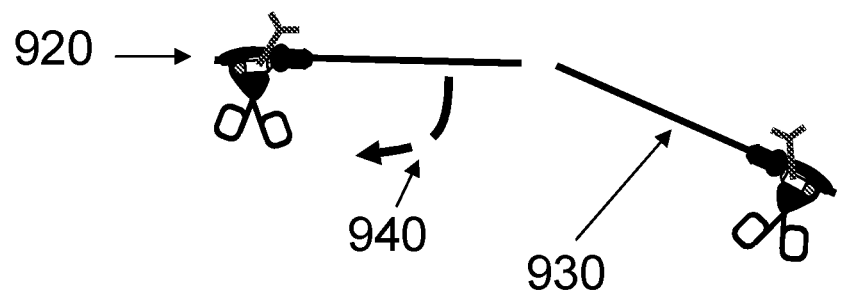

FIG. 7b shows the same tools at a later time t+Δt, where Δt is a small time interval. Left tool 920 is moving to the right and downward, while right tool 930 is moving to the left and upward. If the motion continues (shown by the dashed line in FIG. 7c), then by the end of the next time interval, in other words, at some time between time t+Δt and time t+2Δt, the tools will collide, as shown by tool tips within the dotted circle 950 in FIG. 7c.

In this embodiment, the system automatically prevents predicted collisions and, in this example, the system applies a motion 940 to redirect left tool 920 so as to prevent the collision.

In other embodiments, the system warns/signals the operator that a collision is likely to occur, but does not alter the movement of any tool. Such a warning/signaling can be visual or aural, using any of the methods known in the art.

In other embodiments, the prediction function can be enabled to, for non-limiting example, alter the field of view to follow the predicted movement of a tool or of an organ, to warn of (or prevent) predicted motion into a no-fly zone, to warn of (or prevent) predicted motion out of a preferred zone.

Example 9—Right Tool Function/Rule

Figure 8:
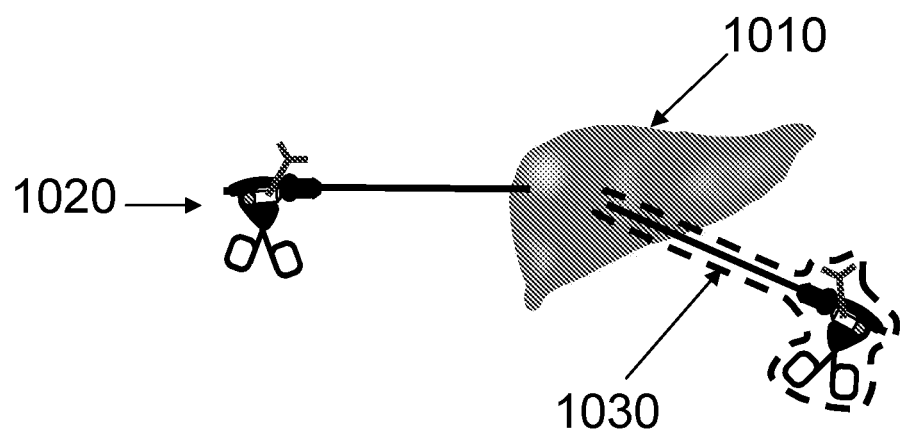
FIG. 8 illustrates an embodiment of a right tool function.

In reference to FIG. 8, which shows, in a non-limiting manner, an embodiment of a right tool function. FIG. 8 schematically illustrates a liver 1010, a left tool 1020 and a right tool 1030. The right tool, illustrated schematically by the dashed line 1040, is labeled and its 3D spatial location is constantly and real-time stored in a database. Now, according to the right tool function/rule the endoscope constantly tracks the right tool.

It should be pointed out that the same rule/function applies for the left tool (the left tool function/rule).

It should be further pointed out that paradigm of tracking a tool in a particular region of the field of view can be extended to any number of tools, for non-limiting example, upper tool function, lower tool function, second-from-right function, and second-from-left function. Other such rules/functions will be obvious to one skilled in the art.

Example 10—Field of View Function/Rule

In reference to FIG. 9, which shows, in a non-limiting manner, an embodiment of a field of view function/rule.

Figure 9A:
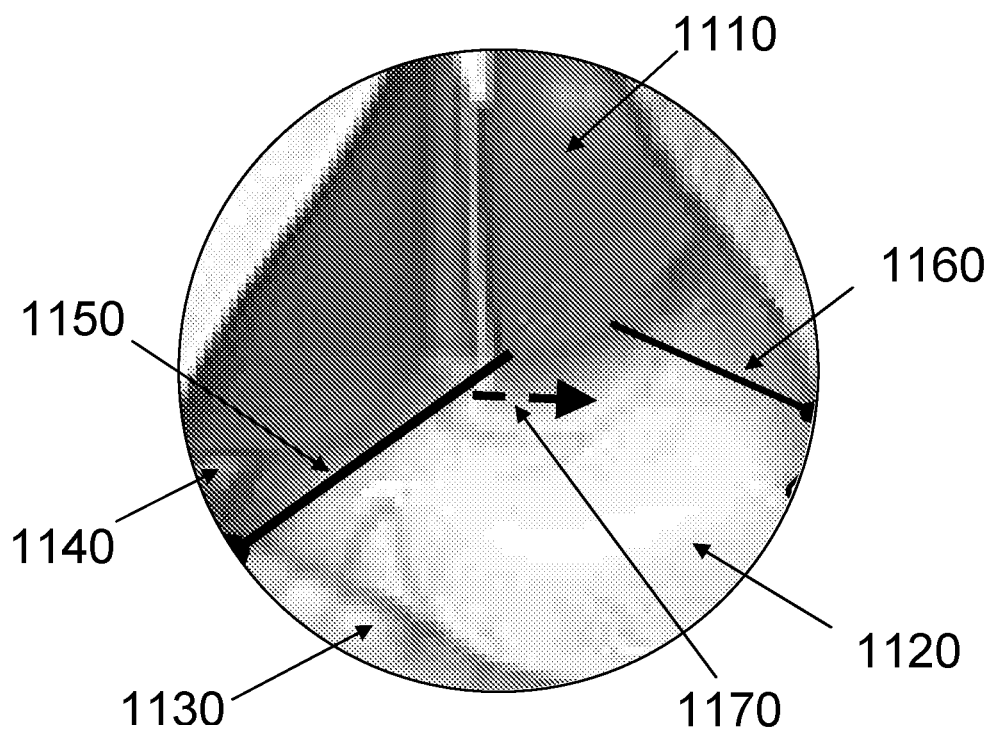
FIG. 9A-B illustrates an embodiment of a field of view function.

FIG. 9a schematically illustrates a field of view of the abdomen at a time t. In the field of view are the liver 1110, stomach 1120, intestines 1130 and gall bladder 1140.

The gall bladder is nearly completely visible at the left of the field of view. Two tools are also in the field of view, with their tips in proximity with the liver. These are left tool 1150 and right tool 1160. In this example, the field of view function/rule tracks left tool 1150. In this example, left tool 1150 is moving to the right, as indicated by arrow 1170.

Figure 9B:
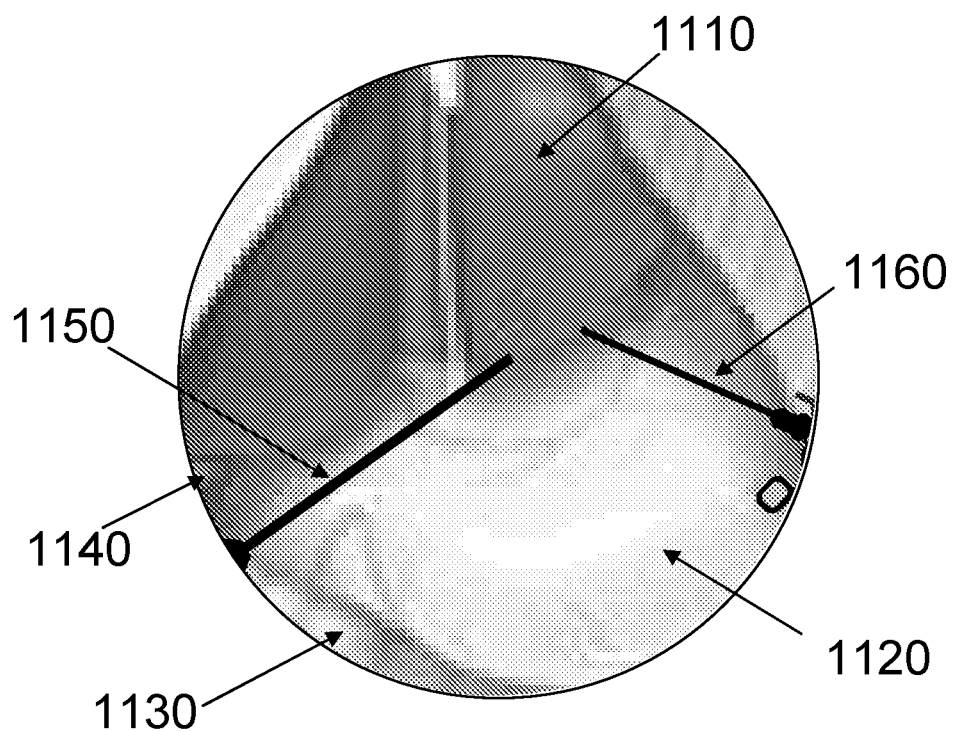

FIG. 9b shows the field of view at time t+Δt. The field of view has moved to the right so that the tip of left tool 1150 is still nearly at the center of the field of view. It can be seen that much less of gall bladder 1140 is visible, while more of right tool 1160 has entered the field of view.

The field of view function/rule can be set to follow a selected tool, as in this example, or to keep a selected organ in the center of the field of view. It can also be set to keep a particular set of tools in the field of view, zooming in or out as necessary to prevent any of the chosen tools from being outside the field of view.

Alternatively, the field of view function/rule defines n 3D spatial positions; n is an integer greater than or equal to 2; the combination of all of the n 3D spatial positions provides a predetermined field of view.

Each movement of the endoscope or the surgical tool within the n 3D spatial positions is an allowed movement and any movement of the endoscope or the surgical tool outside the n 3D spatial positions is a restricted movement.

Alternatively, the field of view function/rule defines n 3D spatial positions; n is an integer greater than or equal to 2; the combination of all of the n 3D spatial positions provides a predetermined field of view.

According to the field of view function/rule, the endoscope is relocated if movement has been detected by the detection means, such that the field of view is maintained.

Example 11—Tagged Tool Function/Rule (or Alternatively the Preferred Tool Rule)

Figure 10:
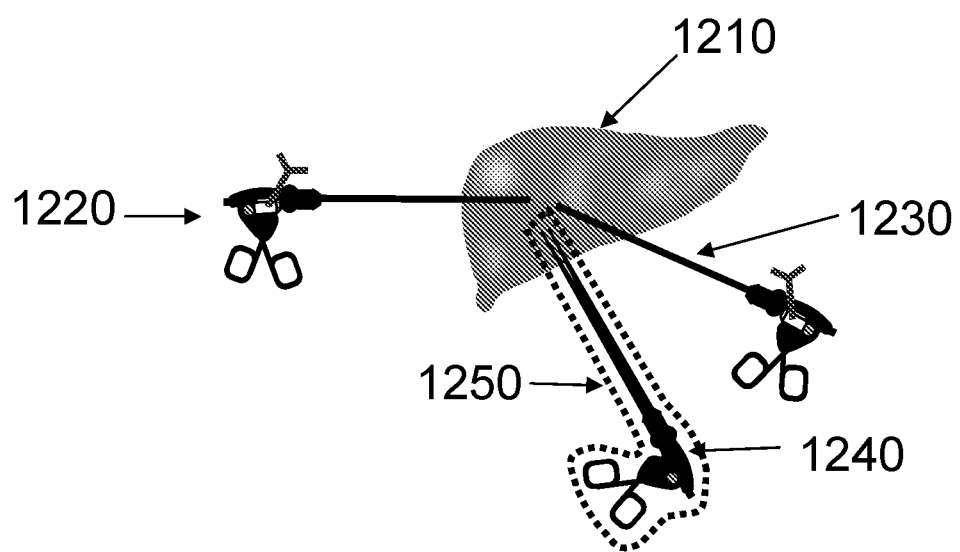
FIG. 10 illustrates an embodiment of a tagged tool function.

In reference to FIG. 10, which shows, in a non-limiting manner, an embodiment of a tagged tool function/rule.

FIG. 10 shows three tools (1220, 1230 and 1240) in proximity to the organ of interest, in this example, the liver 1210.

The tool most of interest to the operator, at this point during the operation, is tool 1240. Tool 1240 has been tagged (dotted line 1250); the 3D spatial location of tool 1240 is constantly stored in a database and this spatial location has been labeled as one of interest.

The system can use this tagging for many purposes, including, but not limited to, keeping tool 1240 in the center of the field of view, predicting its future motion, keeping it from colliding with other tools or keeping other tools from colliding with it, instructing the endoscope to constantly monitor and track the tagged tool 1250 and so on.

It should be noted that in the preferred tool rule, the system tags one of the tools and performs as in the tagged tool rule/function.

Example 12—Proximity Function/Rule

In reference to FIG. 11, which shows, in a non-limiting manner, an embodiment of a proximity function/rule.

Figure 11A:
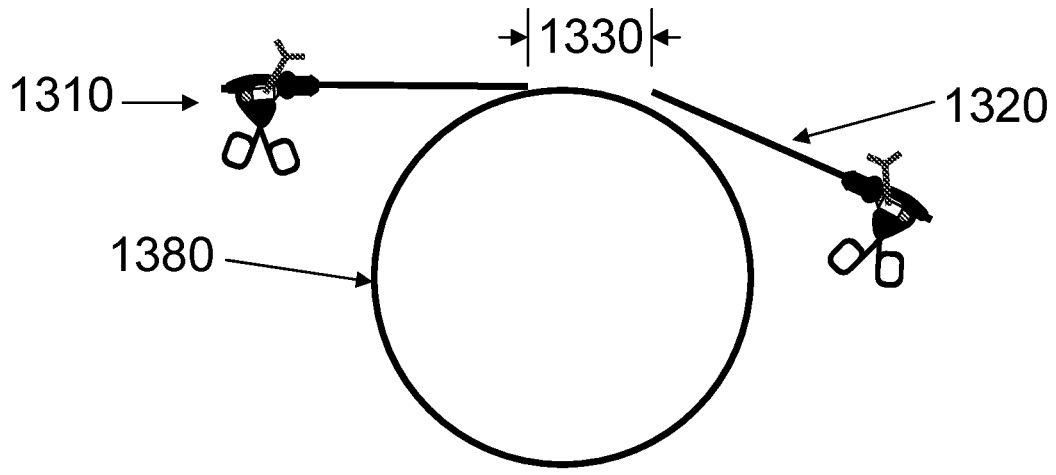
FIG. 11A-C illustrates an embodiment of a proximity function.

FIG. 11a schematically illustrates two tools (1310 and 1320) separated by a distance 1330 which is greater than a predefined proximity distance. Since tool 1310 is not within proximity of tool 1320, the field of view (1380) does not move.

Figure 11B:
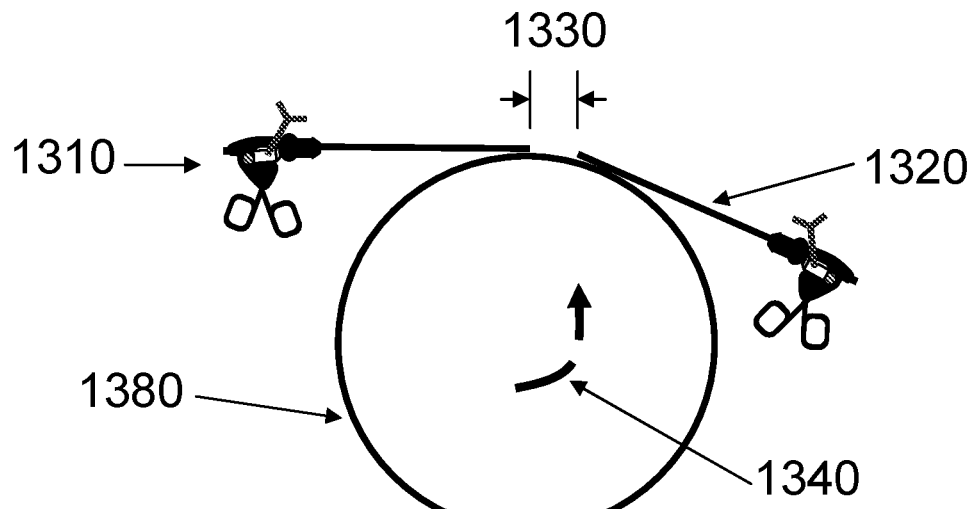

FIG. 11b schematically illustrates two tools (1310 and 1320) separated by a distance 1330 which is less than a predefined proximity distance.

Figure 11C:
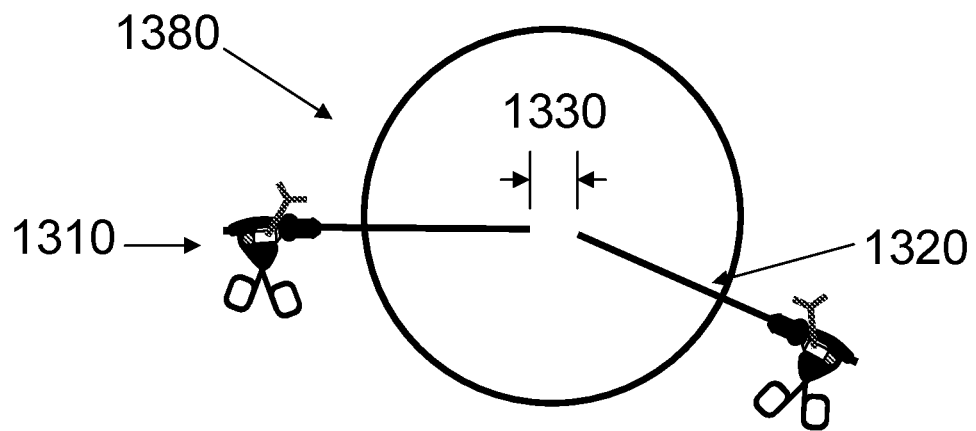

Since tool 1310 is within proximity of tool 1320, the field of view 1380 moves upward, illustrated schematically by arrow 1340, until the tips of tool 1310 and tool 1320 are in the center of field of view 1380 (FIG. 11c).

Alternatively the once the distance 1330 between the two tool 1320 and 1310 is smaller than a predetermined distance, the system alerts the user of the proximity (which might lead to a collision between the two tools). Alternatively, the system moves one of the tools away from the other one.

Example 13—Operator Input Function/Rule

In reference to FIG. 12, which shows, in a non-limiting manner, an embodiment of an operator input function/rule. According to this embodiment, input is received from the operator.

In the following example, the input received from the operator is which tool to track.

Figure 12A:
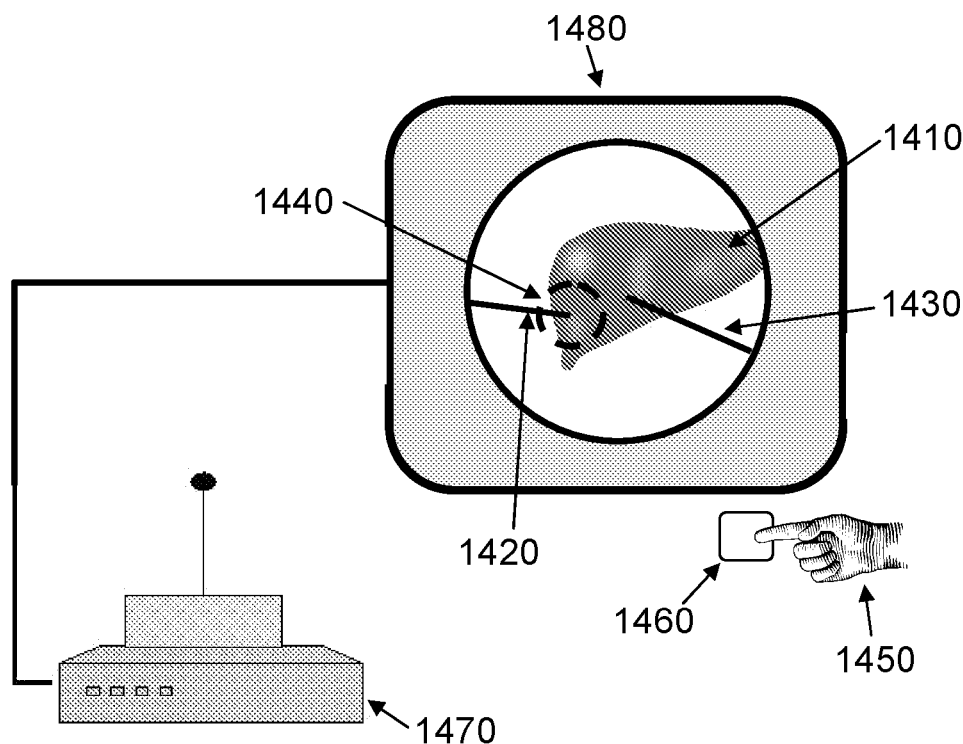
FIG. 12A-B illustrates an embodiment of an operator input function.

FIG. 12a schematically illustrates an endoscope with field of view 1480 showing a liver 1410 and two tools 1420 and 1430. A wireless transmitter 1460 is enabled to transmit coded instructions through receiver 1470. Operator 1450 first selects the tip of the left tool as the region of interest, causing the system to tag (1440) the tip of the left tool.

Figure 12B:
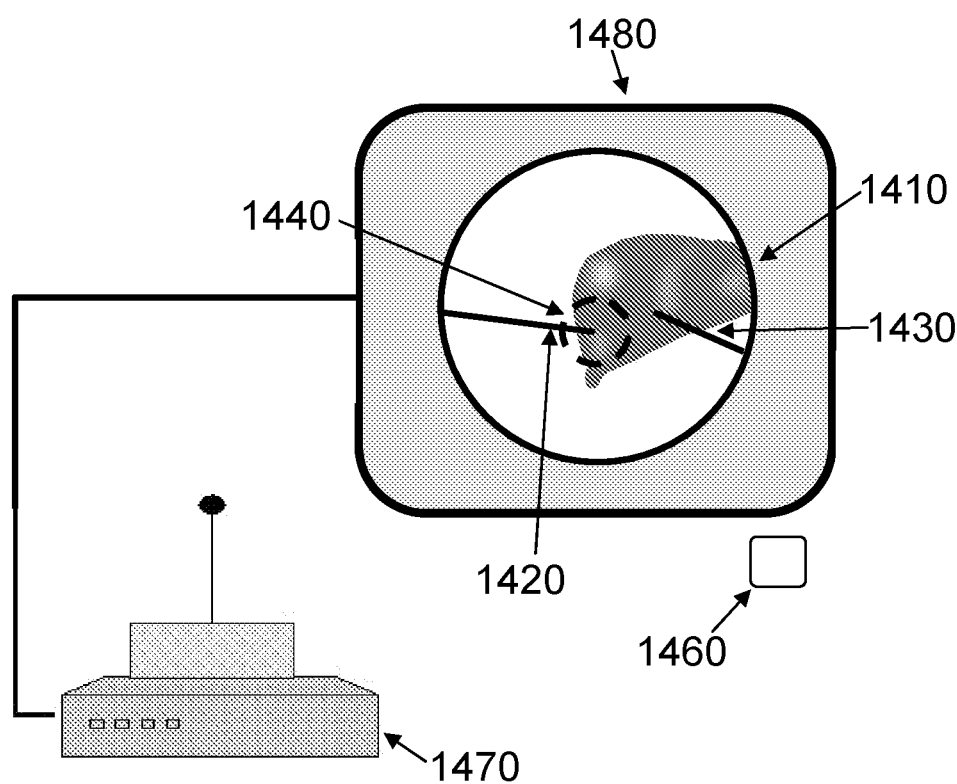

As illustrated in FIG. 12b, the system then directs and modifies the spatial position of the endoscope so that the tagged tool tip 1440 is in the center of the field of view 1480.

Another example of the operator input function/rule is the following:

If a tool has been moved close to an organ in the surgical environment, according to the proximity rule or the collision prevention rule, the system will, according to one embodiment, prevent the movement of the surgical tool.

According to one embodiment of the present invention, once the surgical tool has been stopped, any movement of the tool in a direction toward the organ is interpreted as input from the operator to continue the movement of the surgical tool in that direction.

Thus, according to this embodiment, the operator input function/rule receives input from the operator (i.e., physician) to continue to move of the surgical tool, even though it violates the collision prevention rule. The input is simply in the form of the continued movement of the surgical tool after the alert of the system or after movement prevention by the system.

Example 14—Constant Field of View Rule/Function

In reference to FIGS. 13A-D, which shows, in a non-limiting manner, an embodiment of a tracking system with a constant field of view rule/function.

In many endoscopic systems, the tip lens in the camera optics is not at a right angle to the sides of the endoscope. Conventionally, the tip lens angle is described relative to the right angle, so that a tip lens at right angles to the sides of the endoscope is described as having an angle of 0. Typically, angled endoscope tip lenses have an angle of 30° or 45°. This tip lens angle affects the image seen during zooming. FIG. 13A-D illustrates, in an out-of-scale manner, for a conventional system, the effect of zooming in the field of view in an endoscope with tip lens set straight in the end (FIGS. 13A and 13B) vs. the effect of zooming in the field of view in an endoscope with angled tip lens (FIGS. 13C and 13D).

Figure 13A:
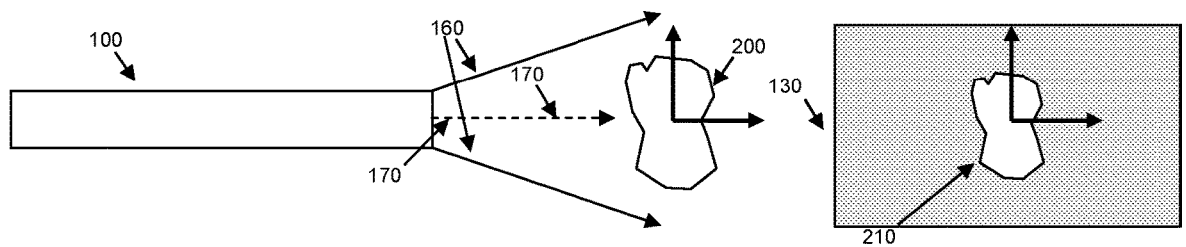
FIG. 13A-D illustrates an embodiment of a constant field of view rule.
Figure 13B:
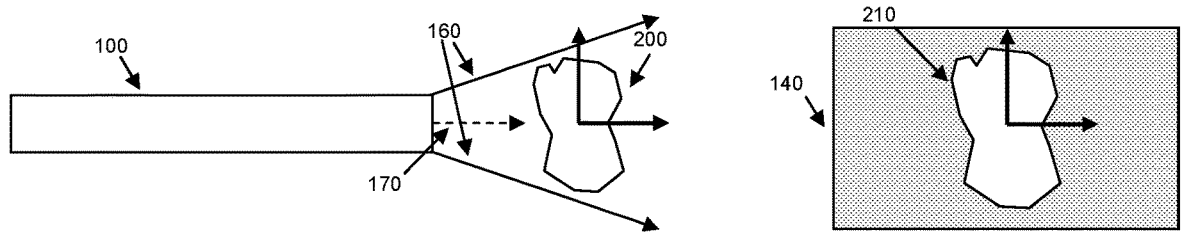
Figure 13C:
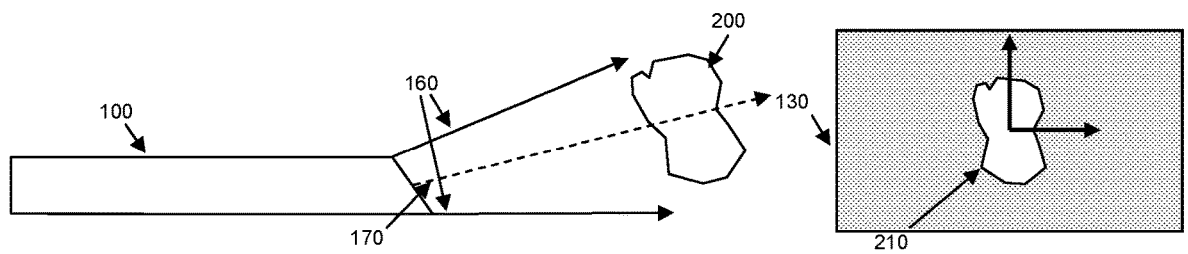
Figure 13D:
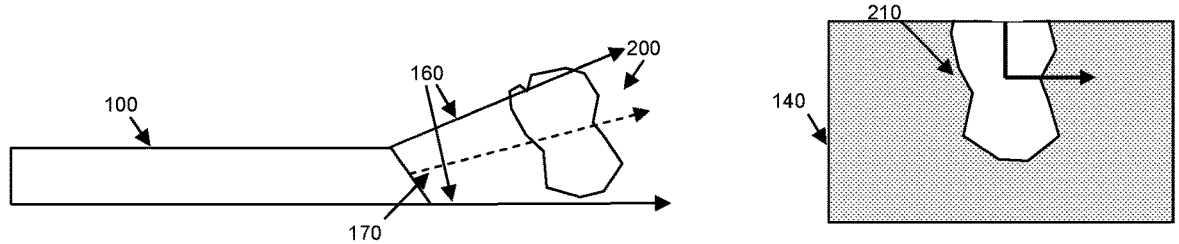

FIGS. 13A and 13C illustrate the endoscope (100), the object it is viewing (200) and the image seen by the endoscope camera (130) before the zoom. The solid arrows (160) show the limits of the FOV and the dashed arrow (170), the center of the field of view (FOV); since the object is in the center of the FOV, an image of the object (210) is in the center of the camera image (130). FIGS. 13B and 13D illustrate the endoscope (100), the object it is viewing (200) and the image seen by the endoscope camera (130) after the zoom. The solid arrows (160) show the limits of the FOV and the dashed arrow (170), the center of the field of view.

If the tip lens is set straight in the end of the endoscope (FIGS. 13A and 13B), an object (200) in the center of the field of view will be in the center of the field of view (FOV) (and the camera image) (130) both before (FIG. 13A) and after (FIG. 13B) the zoom. However, if the tip lens is set at an angle in the end of the endoscope (FIGS. 13C and 13D), then an object that is in the center of the FOV (and the camera image) before the zoom (FIG. 13C) will not be in the center of the FOV (or the camera image) after the zoom (FIG. 13D) since the direction of motion of the endoscope is not the direction in which the center of the field of view (170) points.

In an embodiment of the system of the present invention, unlike in conventional systems, the controlling means maintains the center of the field of view (FOV) during zoom independent of the tip lens angle. An advantage of controlling the zoom of the endoscope via a data processing system is that the tip lens angle does not need to be input to the data processing system, obviating a possible source of error.

According to one embodiment of the present invention, the endoscope's movement will be adjusted in order to maintain a constant field of view.

Example 15—Misalignment Rule/Function

According to another embodiment of the present invention, the system can inform the user of any misalignment of the same system.

Misalignment of the system may cause parasitic movement of the endoscope tip, where the endoscope tip does not move exactly in the expected direction. According to one embodiment of the system, the system comprises sensors (e.g., gyroscopes, accelerometers and any combination thereof) that calculate/estimates the position of the pivot point in real time in order to (a) inform the user of misalignment; or (b) calculate the misalignment so that the system can adjust its movement to prevent parasitic movement.

Example 16—Change of Speed Rule/Function

Figure 14:
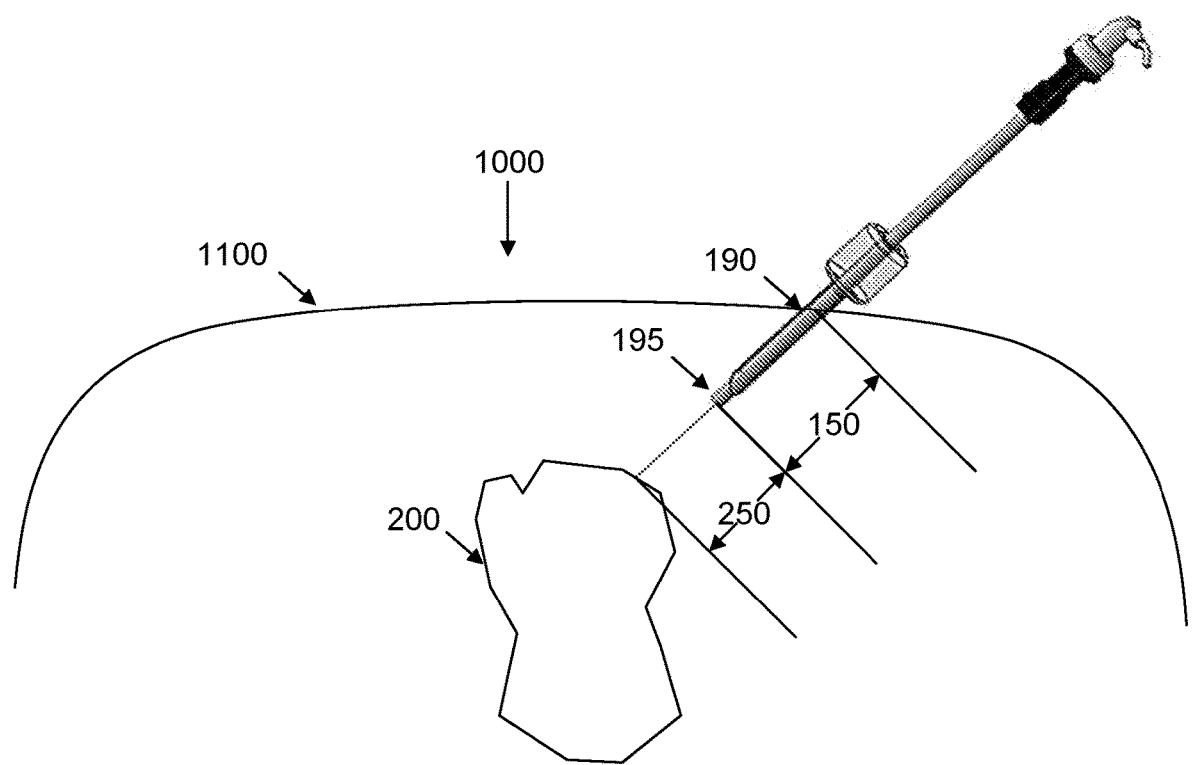
FIG. 14 illustrates an embodiment of a change of speed rule.

In reference to FIG. 14, which shows, in a non-limiting manner, an embodiment of a tracking system with a change of speed rule/function.

In conventional endoscopic control systems, motion of the endoscope occurs at a single speed. This speed is fairly fast so that the endoscope can be moved rapidly between locations that are well separated. However, this means that making fine adjustments so difficult that fine adjustments are normally not made. In an embodiment of the present invention, the speed of the tip of the endoscope is automatically varied such that, the closer the endoscope tip is to an object, be it a tool, an obstacle, or the object of interest, the more slowly it moves. In this embodiment, as shown in FIG. 14, measurements are made of the distance X (150) from the tip (195) of the endoscope (100) to the pivot point of the endoscope (190), where the pivot point is at or near the surface of the skin (1100) of a patient (1000). Measurements are also made of the distance Y (250) from the tip of the endoscope (195) to the object in the center of the scene of view (200). From a predetermined velocity $V_p$, the actual velocity of the tip of the endoscope at a given time, $V_{act}$, is calculated from $$V_{act} \propto \frac{Y}{X} V_p$$

Therefore, the closer to the object at the center of the scene of view, the more slowly the endoscope moves, making it possible to use automatic control of even fine adjustments, and reducing the probability that the endoscope will come in contact with tissue or instruments.

Example 17—Input Movement Protocol, Movement of a Tool

Non-limiting examples of input movement protocols involving movement of tools and associated output movement protocols will be given. For simplicity, the input commands comprise a single movement protocol. It is clear that a movement command can comprise any number of movement protocols, positions, repositions and actions, In reference to FIG. 15A-B, which shows, in a non-limiting manner, an embodiment of an input movement protocol comprising shaking a tool.

Figure 15A:
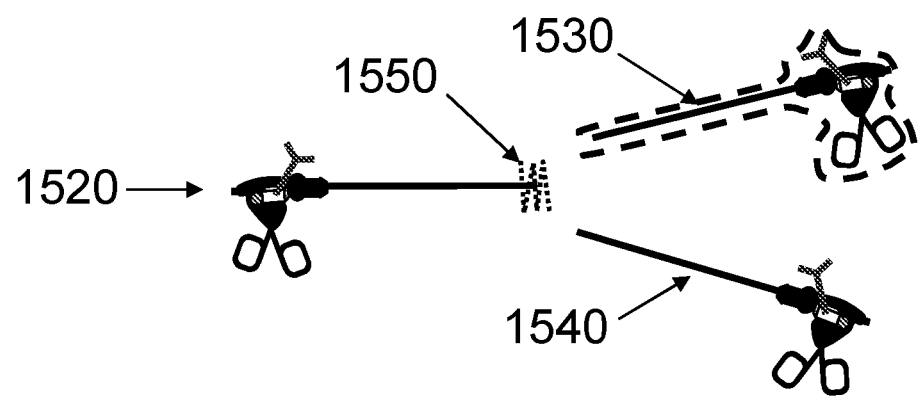
FIGS. 15A-B and 16A-B illustrate embodiments of tool gesture input movement protocols.

In FIG. 15A, a system comprising three tools (1520, 1530, 1540) is illustrated; the system is tracking (dashed line) the upper right tool (1530). In order to change tracking to the leftmost tool (1520), the leftmost tool (1520) is shaken (1550, dotted line)

Figure 15B:
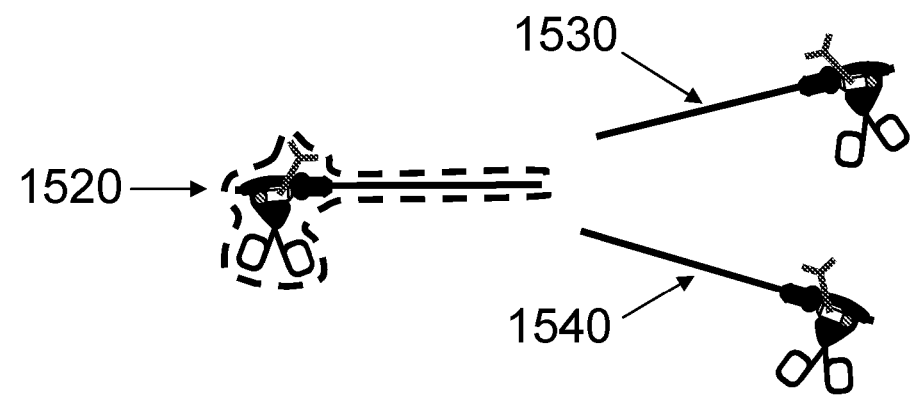

As shown in FIG. 15B, once the leftmost tool (1520) has been shaken. according to the output movement protocol, the system tracks (dashed line) the leftmost tool (1520).

In this example, for clarity, a single tool is tracked. It is clear that a plurality of tools can be simultaneously tracked.

Figure 16A:
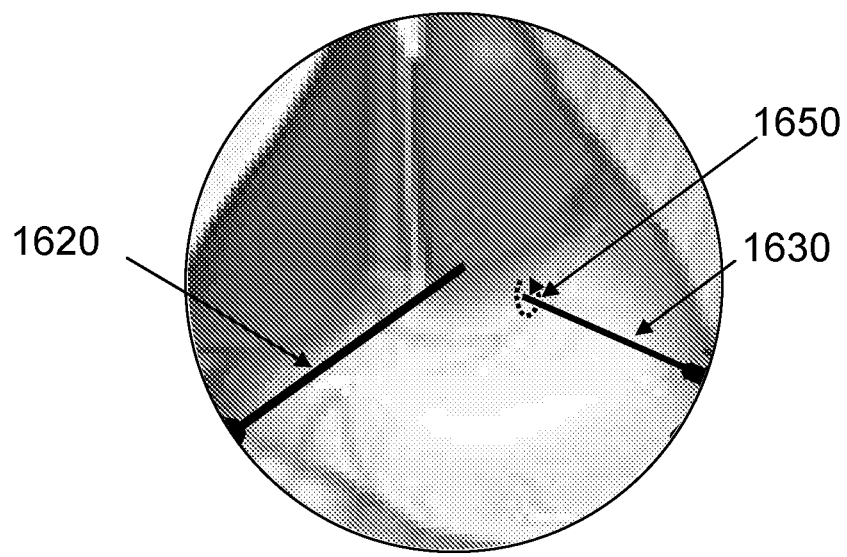
Figure 16B:
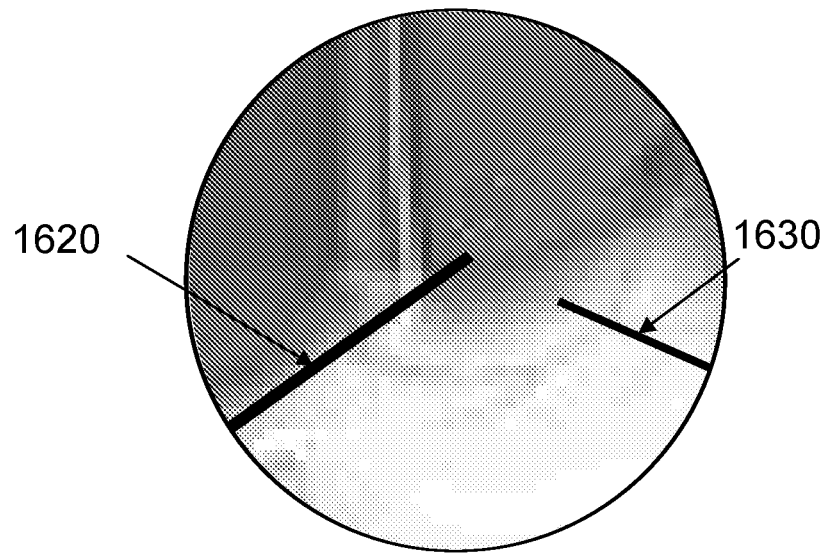

In reference to FIG. 16A-B, which shows, in a non-limiting manner, an embodiment of a zoom command.

In FIG. 16A, two tools (1620, 1630) are being used in an operation on the liver (1610). To command a zoom inward, the tip of a tool, in this case, the right tool (1630), is moved in a clockwise circle (1650, dotted line).

As shown in FIG. 16B, once the circle has been made, according to the output protocol, the field of view is zoomed inward, keeping the center of the field of view the same, so that the image is magnified by 50%.

In this embodiment, an input protocol of a counterclockwise circle (not shown) of either tool would result in an output movement protocol of a zoom outward, increasing the field of view and demagnifying the image by 50%.

The embodiments shown herein are merely exemplary—there are many input movement protocols and many output movement protocols which have not been shown.

It should be noted that the association of input and output movement protocols is arbitrary; any input movement protocol can be associated with any output protocol.

Example 18—Input Movement Protocol, Movement of an Operator

Non-limiting examples of input movement protocols involving movement of a part of an operator, in this case the hand, and associated output movement protocols will be given. For simplicity, each input movement command comprises a single movement protocol, a predetermined gesture. It is clear that a movement command can comprise any number of movement protocols, as well as positions, repositions and actions.

Figure 17A:
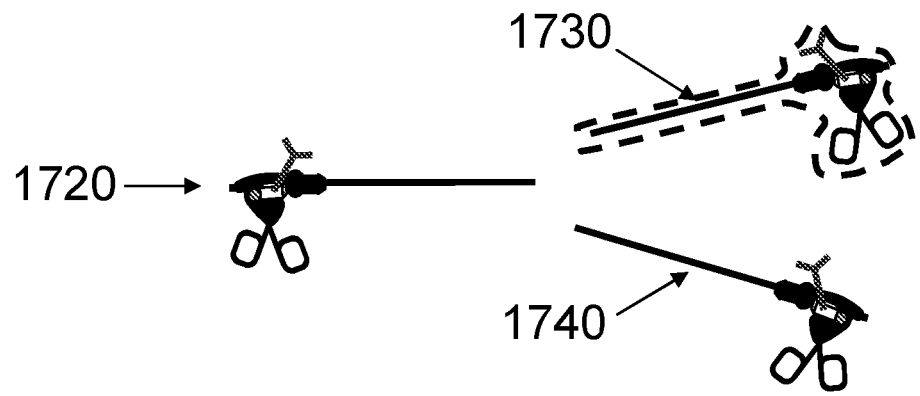
FIGS. 17A-C, 18A-C and 19A-C illustrate embodiments of hand gesture input movement protocols.
Figure 17B:
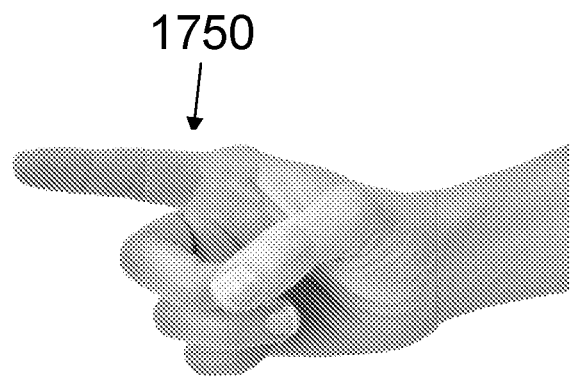
Figure 17C:
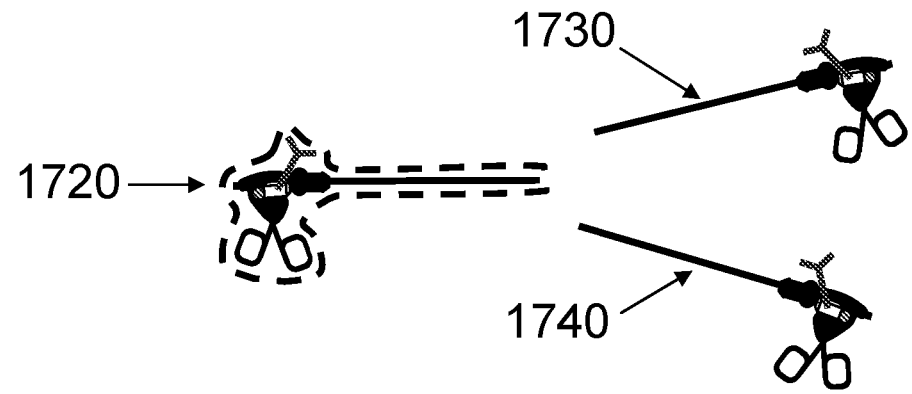

In reference to FIG. 17A-C, which shows, in a non-limiting manner, an embodiment of an input movement protocol comprising pointing a finger.

In FIG. 15A, a system comprising three tools (1520, 1530, 1540) is illustrated; the system is tracking (dashed line) the upper right tool (1530). As shown in FIG. 17B, in order to change tracking to the leftmost tool (1520), the operator points to the left (1750), in this case with the right hand.

As shown in FIG. 17C, once operator has pointed, according to the output movement protocol, the system tracks (dashed line) the leftmost tool (1520).

In this example, for clarity, a single tool is tracked. It is clear that a plurality of tools can be simultaneously tracked.

Figure 18A:
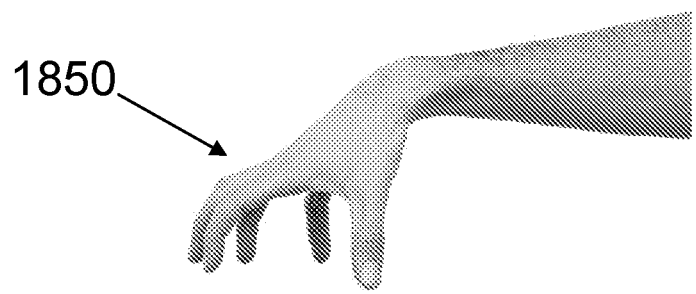
Figure 18B:
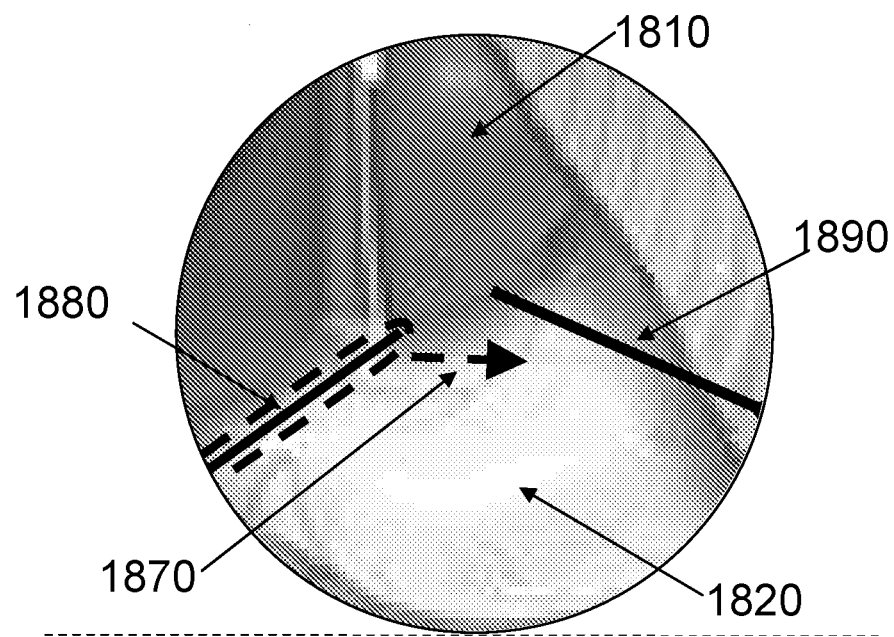
Figure 18C:
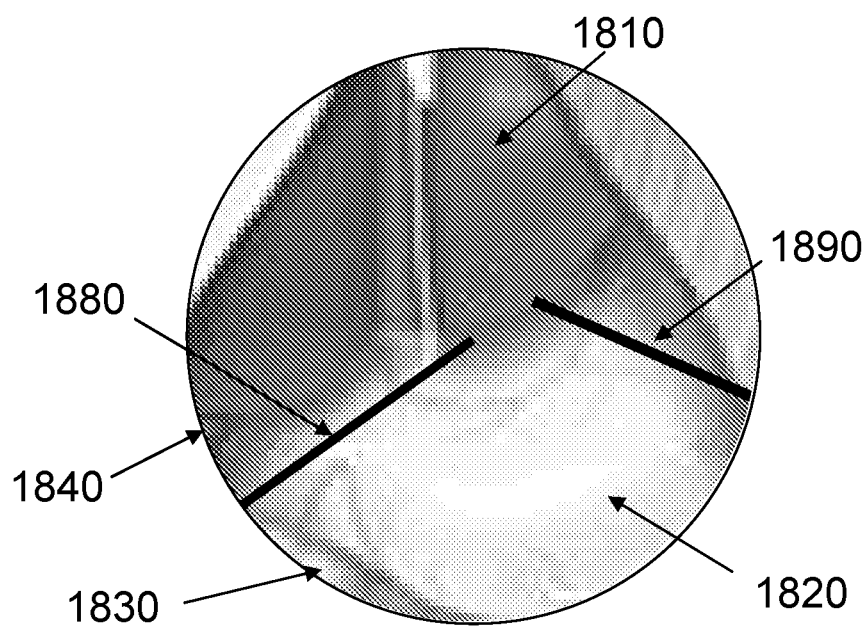

In reference to FIG. 18A-C, which shows, in a non-limiting manner, an embodiment of an input movement protocol for centering a field of view.

In this embodiment, the input movement protocol to place the center of the field of view at the tip of the tracked tool is holding the hand open downward with the finger spread as though picking up a bowl (FIG. 18A, 1850).

As shown in FIG. 18B, the tip of the tracked tool (1880, dashed line) is to the left of the center of the field of view, which shows two tools (1880, 1890), the liver (1810) and the stomach (1820).

The gesture (FIG. 18A, 1850) commands the output movement protocol, that the center of the field of view be moved to the right (dashed arrow, 1870). After the output movement protocol has been completed, the tip of the tracked, left, tool (1880, dashed line) is at the center of the field of view, which shows the two tools (1880, 1890), liver (1810), the stomach (1820), the intestines (1830) and gall bladder (1840).

In this example, for clarity, the center of the field of view follows a single tool. It is clear that the center of the field of view can depend on the locations of a plurality of tools.

Figure 19A:
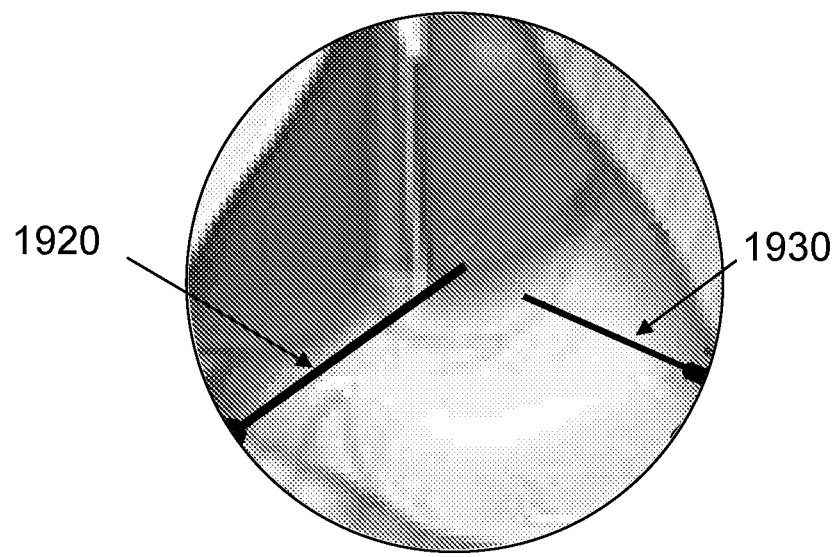
Figure 19B:
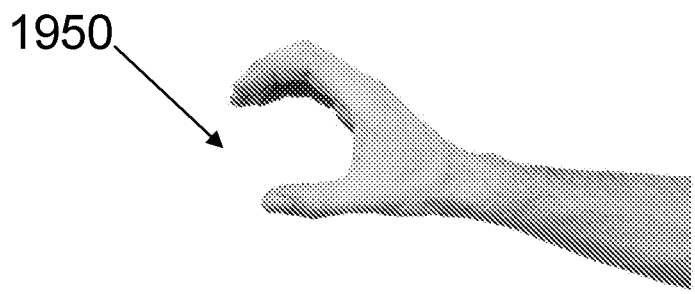
Figure 19C:
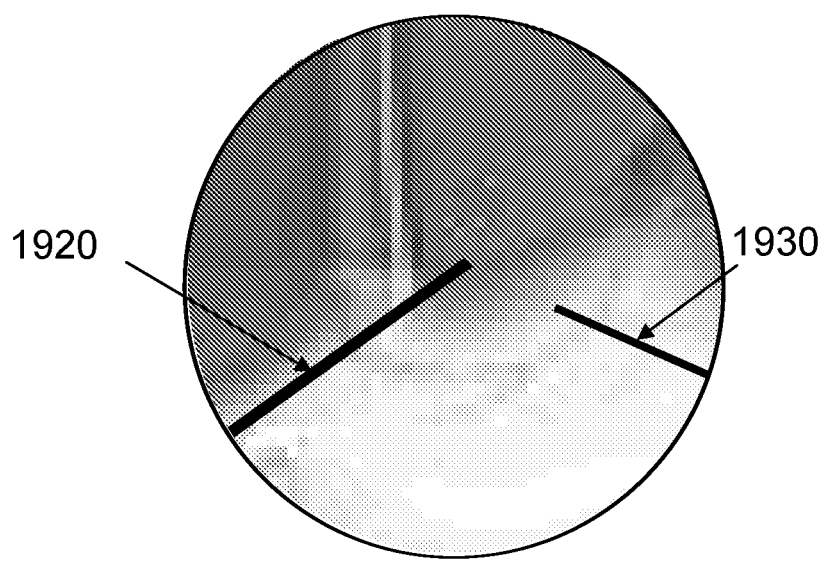

In reference to FIG. 19A-C, which shows, in a non-limiting manner, an embodiment of an input movement protocol to zoom an endoscope.

In this embodiment, the input movement protocol to zoom the endoscope inward is holding an open hand sideways with the fingers together, although picking up a book (FIG. 19A, 1950).

In FIG. 19B, two tools (1920, 1930) are being used in an operation on the liver (1910).

As shown in FIG. 19C, once the input protocol (holding the hand as though picking up a book) is made, according to the output protocol, the field of view is zoomed inward, keeping the center of the field of view the same, so that the image is magnified by 50%.

In this embodiment, an input movement protocol of a book-holding gesture pointing toward the right would result in an output movement protocol of a zoom outward, increasing the field of view and demagnifying the image by 50%.

The embodiments shown herein are merely exemplary—there are many input movement protocols and many output movement protocols which have not been shown.

It should be noted that the association of input and output movement protocols is arbitrary; any input movement protocol can be associated with any output protocol.

Example 19—Input Movement Protocol, Movement of an Operator

A non-limiting example of an input movement protocol comprising movement of a part of an operator, in this case the eye, and an associated output movement protocol will be given. For simplicity, the input movement protocol comprises a single fixed predetermined gesture. It is clear that a movement command can comprise any number of movement protocols, as well as positions, repositions and actions.

Figure 20A:
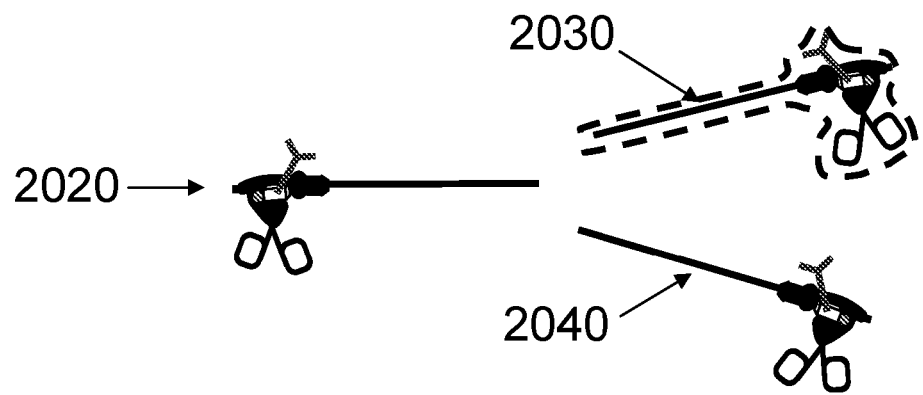
FIG. 20A-C illustrates an embodiment of an eye gesture input movement protocol.
Figure 20B:
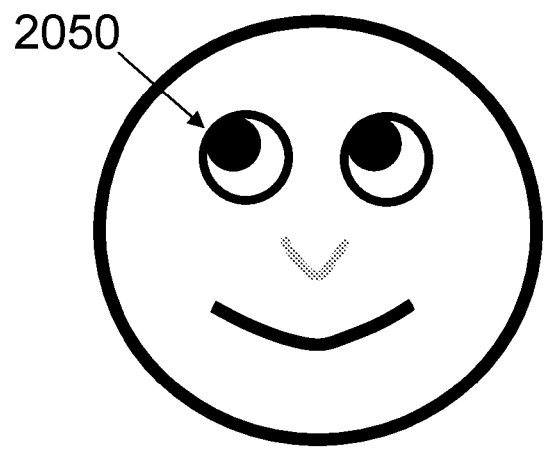
Figure 20C:
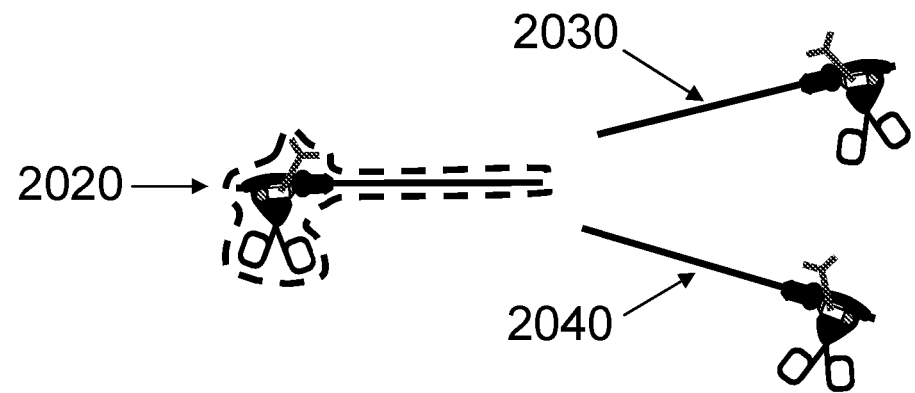

In reference to FIG. 20A-C, which shows, in a non-limiting manner, an embodiment of an input movement protocol comprising moving at least one eye.

In FIG. 20A, a system comprising three tools (2020, 2030, 2040) is illustrated; the system is tracking (dashed line) the upper right tool (2030). In order to change tracking to the leftmost tool (2020), at least one eye is moved to look upward to the left, preferably so that the operator is no longer looking at the display screen, as shown in FIG. 20B (2030). In preferred embodiments, the eye gesture need only be a quick glance, a momentary removal of the eyes from the display.

As shown in FIG. 20C, once the eye gesture (2060) is complete, according to the output movement protocol, the system tracks (dashed line) the leftmost tool (2020).

Figure 21A:
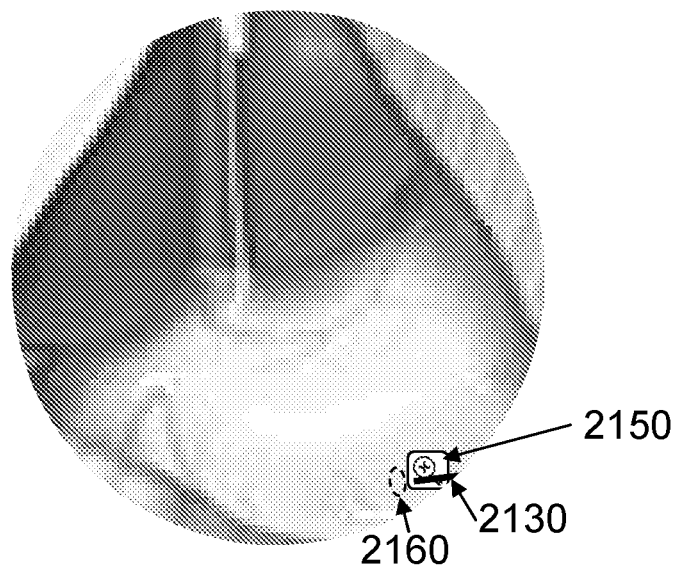
FIG. 21A-B illustrates an embodiment of a location-based input protocol.
Figure 21B:
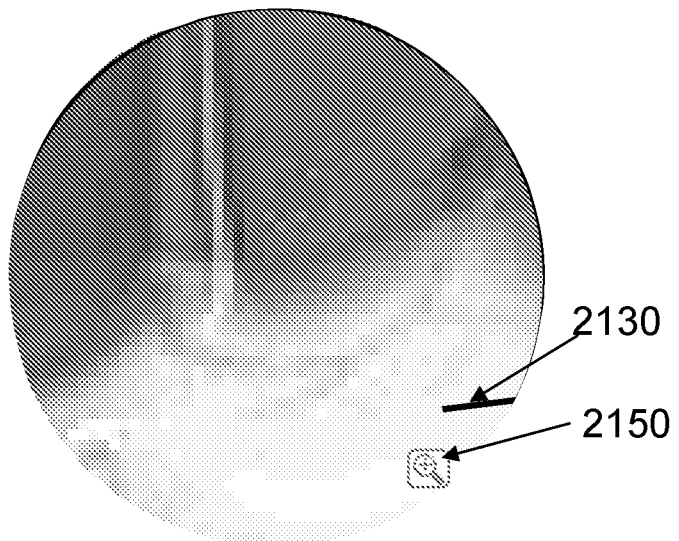

In this example, for clarity, a single tool is tracked. It is clear that a plurality of tools can be simultaneously tracked Example 20—Input Protocol, Position of a Tool A non-limiting example of an input movement command comprising a position of a tool is shown in FIG. 21A-B. The input movement command comprises an input position. In other embodiments, the input movement command can comprise a plurality of positions, repositions, actions and movement protocols.

In FIG. 21A, an embodiment of a display image is shown. The display comprises at least one icon (2150), with each icon being associated with an output command. In this embodiment, icons are invisible until a tool "enters" an icon, in other words, until the image of the tool is in the region of the display which can show the icon. In other embodiments, at least some icons are visible at all times.

In this embodiment, once a tool (2130) has entered an icon (2150), the output command is activated by moving the tool in a gesture which encircles the icon (2160, dotted arrow). In other embodiments, entering the icon region activates the output protocol; in yet other embodiments, other gestures are used.

In this exemplary embodiment, the icon (2150) shows a zoom-inward (+) symbol. After the circling motion (2160, dotted arrow) is completed, the system zooms the endoscope inward until the tool is removed from the icon, whereupon zooming stops and a magnified image is shown (FIG. 21B). The location of the icon is shown greyed-out in FIG. 21B for illustrative purposes. In preferred variants of this embodiment, an icon would only be showed greyed-out if the function with which it is associated is unavailable. In preferred variants, icons are preferably outside the image of the field of view or invisible when not in use, in order to ensure that the image of the field of view is as visible as possible.

In this example, for clarity, a single tool is shown. It is clear that any of a plurality of tools can be positioned over the icon.

Example 21—Input Protocol, Tagging of an Object

Figure 22A:
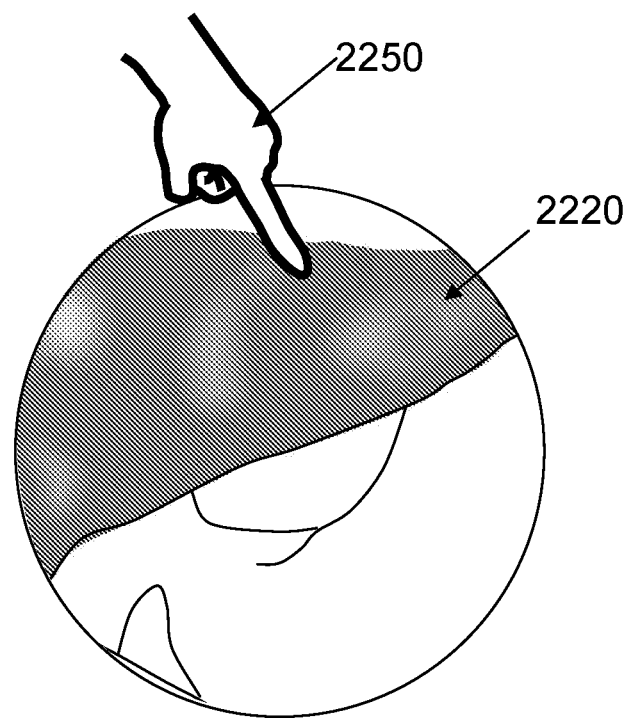
FIG. 22A-B illustrates an embodiment of tagging.
Figure 22B:
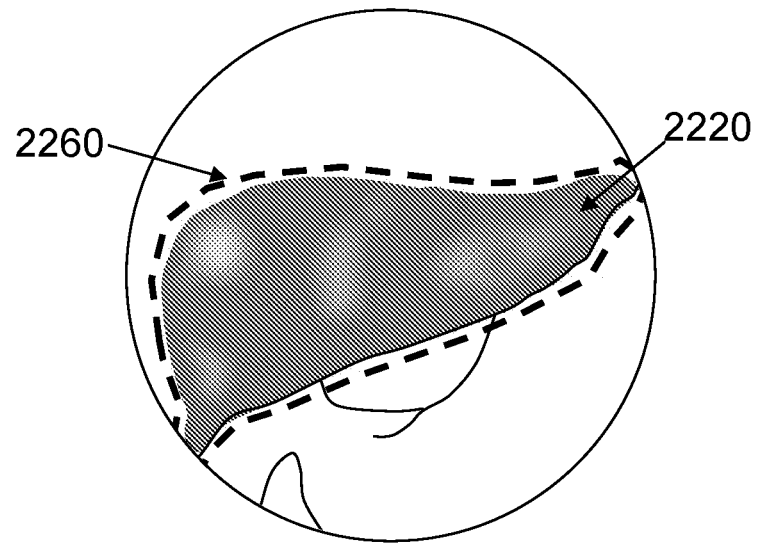

A non-limiting example of an input command comprising an action by a moving element is shown in FIG. 22A-B. For simplicity, the input command comprises a single action. In other embodiments, the input command can comprise a plurality of positions, repositions, actions and movement protocols.

In this embodiment, as shown in FIG. 22A, the command is pointing by a finger of an operator (2250) at the object (2260) to be tagged.

As shown in FIG. 22B, the output protocol tags (2260, dashed line) the object, centers it in the field of view, and zooms the object until it is entirely within the field of view and fills the field of view in at least one direction.

In this example, for clarity, a single tagged object is used. It is clear that any of a plurality of tagged objects can be kept within the field of view.

Example 22—Input Protocol, Activation of a Tool

Figure 23A:
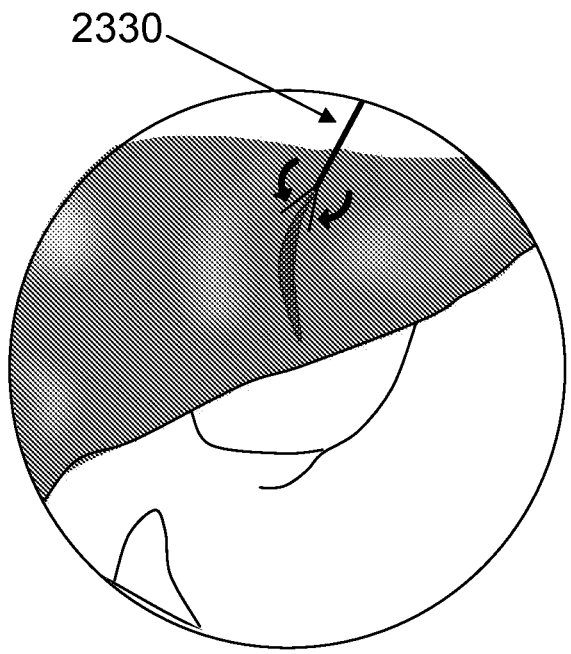
FIG. 23A-B illustrates an embodiment of an action.
Figure 23B:
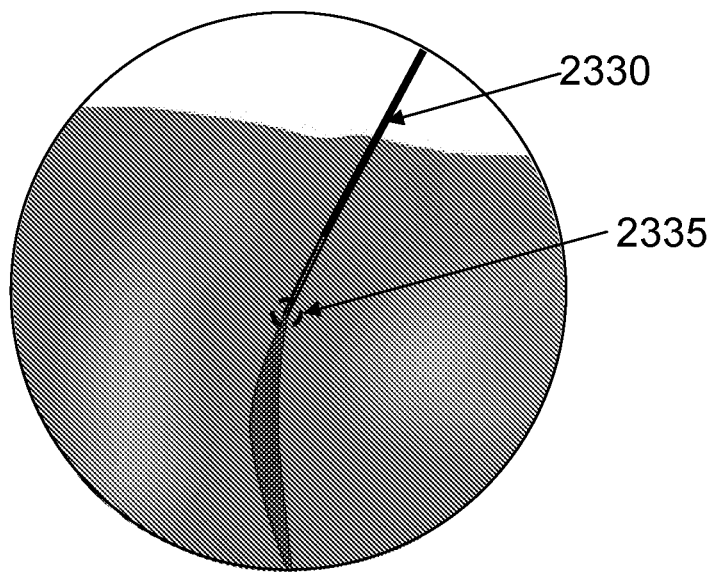

A non-limiting example of an input command comprising an action of activating a tool is shown in FIG. 23A-B. For simplicity, the input command comprises a single action; in other embodiments, the input command can comprise a plurality of positions, repositions, actions and movement protocols.

In this embodiment, as shown in FIG. 23A, the tool (2330) is a grasper and activation comprises closing the grasper (2350, curved arrows).

Closing (2350, curved arrows) of the grasper (2330) results in an output protocol in which (FIG. 23B) the tip (2335, dashed circle) of the grasper (2330) is placed in the center of the field of view and the view zoomed to give a good view of the tip of the grasper.

In this example, for clarity, a single tool is activated. It is clear that any of a plurality of tools can be activated, and that the activated tools need not be of the same type (e.g., a cautery and a graspers).

Example 23—Input Protocol, Tool Reaches Edge of Field of View

Figure 24A:
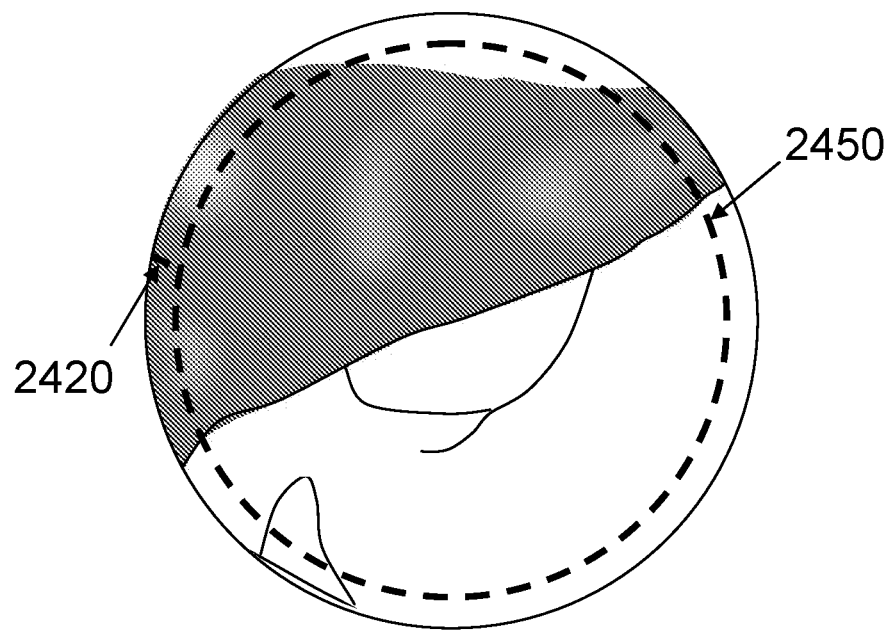
FIG. 24A-B illustrates an embodiment of keeping a tool in the field of view.
Figure 24B:
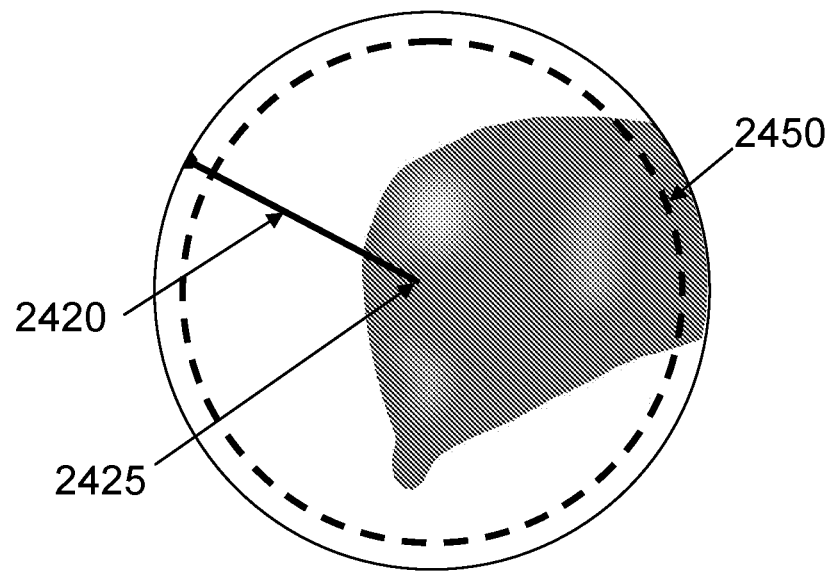

A non-limiting example of an input command to keep a tagged object from reaching an edge of the field of view is shown in FIG. 24A-B.

In this embodiment, as shown in FIG. 24A, the tagged object is a tool (2420). Location of the tip of the tool anywhere in the area between a predetermined distance (2450, dotted line) and the edge of the field of view determines activation of the input command that the tool tip is to be kept within the field of view. This, in turn, activates an output command to maneuver the endoscope so as to place the tip (2425) of the tool (2420) in the center of the field of view, as is shown in FIG. 24B.

In other embodiments, more than one article can be kept from the edge of the field of view. In such embodiments, a plurality of articles can be tagged. If a tagged article reaches an edge of the field of view, the endoscope will maneuver to move the article away from the edge. In some variants of these embodiments, in addition to, or in place of, maneuvering the endoscope, the endoscope's zoom will be altered until all the tagged articles are more than the predetermined distance from the edge.

Example 24—Relationship Between Articles

Figure 25:
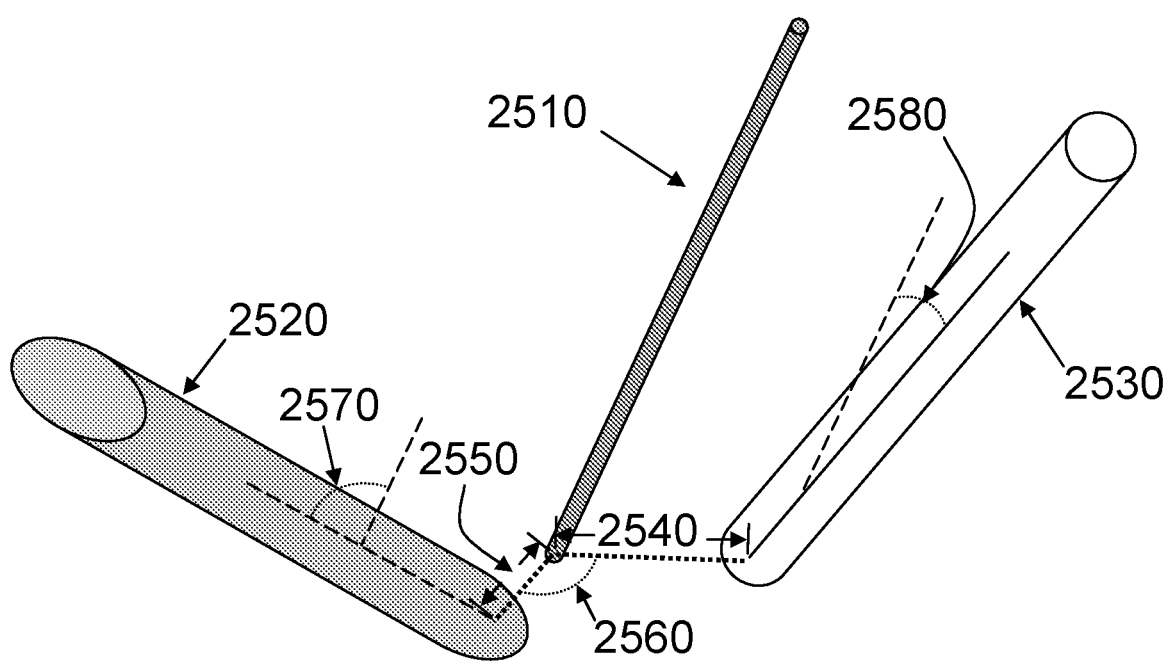
FIG. 25 illustrates an embodiment of a relationship between tools.

A non-limiting example of a relationship between articles is shown in FIG. 25.

In this example, a fluid delivery tube (2520) and a suction tube (2530) are kept at fixed distances (2540, 2550), which are not the same, from a cautery (2510). A predetermined angle (2560) is maintained between the tip of the fluid delivery tube (2520), the tip of the cautery (2510) and the tip of the suction tube (2530). In addition, the longitudinal axes of the tubes are at fixed angles (2570, 2580), not the same, relative to the longitudinal axis of the cautery.

The embodiments shown hereinabove are merely exemplary—there are many input movement protocols, many output movement protocols and many associations between input command and output command which are possible and have not been shown.

It should be noted that the association of input and output commands are typically arbitrary; any input command can be associated with any output command.

It should further be noted that an input command can comprise any of a tool movement, an operator movement and an operator brain signal, and that these can be combined in any way.

In preferred embodiments, the input commands will be chosen so as to make the system operate as intuitively as is practicable.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A maneuvering system, comprising:
   at least one endoscope adapted to real-time provide at least one image of a field of view;
   a first surgical tool moveable within the field of view, and a second surgical tool, each of the endoscope and the first and second surgical tools being separate surgical tools;
   at least one maneuvering mechanism in active communication with at least one of the endoscope, first surgical tool and second surgical tool and configured to maneuver said at least one of the endoscope, first surgical tool and second surgical tool in at least two dimensions;
   a processor and memory in communication with said processor, said memory storing a plurality of predetermined protocols of input movement and a plurality of output commands, each of the plurality of output commands corresponding to one of the protocols of input movement, and a computer program which, when executed by the processor, is configured to real-time image process said at least one image captured by said endoscope to detect movement of at least a portion of said first surgical tool and determine if said detected movement is within one of the plurality of predetermined protocols of input movement, and, if said detected movement of at least a portion of said first surgical tool is within a predetermined protocol of input movement, said processor activates a corresponding one of the predetermined output commands such that at least one of the following is held true:
   the second surgical tool is maneuvered by means of said maneuvering mechanism according to at least one output movement protocol; and
   the second surgical tool is activated according to said at least one output movement protocol.

2. The system of claim 1, wherein said protocol of input movement is selected from a group consisting of: moving said first surgical tool parallel to the X axis; moving said first surgical tool parallel to the Y axis; moving said first surgical tool parallel to the Z-axis; rotational movement of said first surgical tool around an axis parallel to the X axis; rotational movement of said first surgical tool around an axis parallel to the Y axis; rotational movement of said first surgical tool around an axis parallel to the Z axis; shaking said first surgical tool, moving said first surgical tool in at least a portion of a circle, moving said first least one surgical tool in at least a portion of an oval, moving said first surgical tool in at least a portion of an ellipse, moving said first surgical tool in a straight line, moving said first surgical tool in a zigzag, moving said first endoscope parallel to the X axis; moving said first one endoscope parallel to the Y axis; moving said first endoscope parallel to the Z-axis; rotational movement of said first endoscope around an axis parallel to the X axis; rotational movement of said first endoscope around an axis parallel to the Y axis; rotational movement of said first endoscope around an axis parallel to the Z axis; or shaking said first surgical tool moving, and any combination thereof.

3. The system of claim 1, wherein said protocol of input movement is selected from the group consisting of: at least a portion of said first surgical tool is positioned in a predetermined region of said field of view; at least a portion of said first surgical tool is positioned less than a predetermined distance from an edge of said field of view; at least a portion of said first surgical tool is oriented at a predetermined angle in said field of view; there exists a predetermined relationship between at least two articles in said field of view and any combination thereof.

4. The system of claim 1, wherein said activation is selected from a group consisting of: opening the second surgical tool, closing the second surgical tool, causing the second surgical tool to function, stopping the second surgical tool from functioning, introducing the second surgical tool to the surgical environment, energizing the second surgical tool, and removing the second surgical tool from the surgical environment.

5. The system of claim 1, wherein said maneuvering mechanism can maneuver said at least one of the endoscope, first surgical tool and second surgical tool in at least three dimensions.

6. The system of claim 5, including an output movement protocol group consisting of an allowed output movement protocol, a restricted output movement protocol and any combination thereof of a member of a maneuverable object group consisting of said at least one endoscope, said first surgical tool, said second surgical tool and any combination thereof, wherein each member of said output movement protocol group is determinable from input movement protocols comprising historical movements of said member of said maneuverable object group according with historical movement patterns of said member of said maneuverable object group in at least one previous surgery.

7. The system of claim 6, wherein each member of a group consisting of an allowed input movement protocol, a restricted input movement protocol and any combination thereof comprises, stored in said communicable database, each 3D spatial position of said member of said maneuverable object group according with at least two 3D spatial positions of said member of said maneuverable object group, such that each movement pattern of said member of said maneuverable object group and each 3D position of said member of said maneuverable object group according with the same is stored; in said associated allowed output protocol, said allowed movements of said member of said maneuverable object group are movements in which the same is located substantially in at least one of the endoscope 3D spatial positions according with at least one said 3D movement pattern, and said restricted movements are movements in which the location of said member of said maneuverable object group is substantially different from the n 3D spatial positions of the same according with the n movement patterns.

8. The system of claim 6, wherein each member of a group consisting of an allowed output movement protocol, a restricted output movement protocol and any combination thereof comprises at least one rule according to which allowed and restricted movements of said second surgical tool are determined, such that each detected movement of said at least one surgical tool is determined as either an allowed movement or as a restricted movement according to said predetermined set of rules.

9. The system of claim 8, wherein said allowed movement is permitted by said controller and said restricted movement is denied by said controller.

10. The system of claim 8, wherein said predetermined set of rules comprises at least one rule selected from a group consisting of: most used tool rule, right tool rule, left tool rule, field of view rule, no fly zone rule, a route rule, environmental rule, operator input rule, proximity rule; collision prevention rule, history-based rule, tool-dependent allowed and restricted movements rule, preferred volume zone rule, preferred tool rule, movement detection rule, tagged tool rule, change of speed rule and any combination thereof.

11. The system of claim 10, wherein at least one of the following is being held true (a) said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movements are movements in which said at least one surgical tool is located substantially in at least one of said n 3D spatial positions of said predefined route, and said restricted movements are movements in which said location of said at least one surgical tool is substantially different from said n 3D spatial positions of said predefined route; (b) said environmental rule comprises a communicable database; said communicable database configured to receive at least one real-time image of said surgical environment and is configured to perform real-time image processing of the same and to determine the 3D spatial position of hazards or obstacles in said surgical environment; said environmental rule is configured to determine said allowed and restricted movements according to said hazards or obstacles in said surgical environment, such that said restricted movements are movements in which said at least one surgical tool is located substantially in at least one of said 3D spatial positions, and said allowed movements are movements in which the location of said at least one surgical tool is substantially different from said 3D spatial positions; said hazards or obstacles in said surgical environment are selected from a group consisting of tissue, a surgical tool, an organ, an endoscope and any combination thereof; (c) said operator input rule comprises a communicable database; said communicable database is configured to receive an input from the operator of said system regarding said allowed and restricted movements of said at least one surgical tool; (d) said proximity rule is configured to define a predetermined distance between at least two surgical tools; said allowed movements are movements which are within the range or out of the range of said predetermined distance, and said restricted movements which are out of the range or within the range of said predetermined distance; (e) said proximity rule is configured to define a predetermined angle between at least three surgical tools; said allowed movements are movements which are within the range or out of the range of said predetermined angle, and said restricted movements which are out of the range or within the range of said predetermined angle; (f) said collision prevention rule is configured to define a predetermined distance between said at least one surgical tool and an anatomical element within said surgical environment; said allowed movements are movements which are in a range that is larger than said predetermined distance, and said restricted movements are movements which is in a range that is smaller than said predetermined distance; (g) said right tool rule is configured to determine said allowed movement of said endoscope according to the movement of the surgical tool positioned to right of said endoscope; further wherein said left tool rule is configured to determine said allowed movement of said endoscope according to the movement of the surgical tool positioned to left of said endoscope; (h) said tagged tool rule comprises means configured to tag at least one surgical tool within said surgical environment and to determine said allowed movement of said endoscope to constantly track the movement of said tagged surgical tool; (i) said field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view, such that said allowed movements are movements in which said endoscope is located substantially in at least one of said n 3D spatial positions, and said restricted movements are movements in which the location of said endoscope is substantially different from said n 3D spatial positions; (j) said preferred volume zone rule comprises a communicable database comprising n 3D spatial positions; n is an integer greater than or equal to 2; said n 3D spatial positions provides said preferred volume zone; said preferred volume zone rule is configured to determine said allowed movement of said endoscope within said n 3D spatial positions and restricted movement of said endoscope outside said n 3D spatial positions, such that said allowed movements are movements in which said endoscope is located substantially in at least one of said n 3D spatial positions, and said restricted movements are movements in which the location of said endoscope is substantially different from said n 3D spatial positions; (k) preferred tool rule comprises a communicable database, said database stores a preferred tool; said preferred tool rule is configured to determine said allowed movement of said endoscope to constantly track the movement of said preferred tool; (l) said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and allowed movement if said movement is outside said no fly zone, such that said restricted movements are movements in which said at least one of said surgical tool is located substantially in at least one of said n 3D spatial positions, and said allowed movements are movements in which the location of said at least one surgical tool is substantially different from said n 3D spatial positions; (m) said most used tool rule comprises a communicable database counting the amount of movement of each of said surgical tools; said most used tool rule is configured to constantly position said endoscope to track the movement of the most moved surgical tool; (n) said history-based rule comprises a communicable database storing each 3D spatial position of each of said surgical tool, such that each movement of each surgical tool is stored; said history-based rule is configured to determine said allowed and restricted movements according to historical movements of said at least one surgical tool, such that said allowed movements are movements in which said at least one surgical tool is located substantially in at least one of said 3D spatial positions, and said restricted movements are movements in which the location of said at least one surgical tool is substantially different from said n 3D spatial positions; (o) said tool-dependent allowed and restricted movements rule comprises a communicable database; said communicable database is configured to store predetermined characteristics of at least one of said surgical tool; said tool-dependent allowed and restricted movements rule is configured to determine said allowed and restricted movements according to said predetermined characteristics of said surgical tool; such that allowed movements as movements of said endoscope which tracks said surgical tool having said predetermined characteristics; (p) said movement detection rule comprises a communicable database comprising the real-time 3D spatial positions of each of said surgical tool; said movement detection rule is configured to detect movement of said at least one surgical tool when a change in said 3D spatial positions is received, such that said allowed movements are movements in which said endoscope is re-directed to focus on the moving surgical tool; and any combination thereof.

12. The system of claim 11, wherein said system is configured to provide an alert for said restricted movement of said at least one surgical tool; wherein said alert is selected from a group consisting of audio signaling, voice signaling, light signaling, flashing signaling and any combination thereof.

13. The system of claim 1, wherein a relationship between magnitude of an output movement and magnitude of said detected movement is selected from a group consisting of: the magnitude of said output movement is proportional to the magnitude of said detected movement; the magnitude of said output movement is substantially identical to the magnitude of said detected movement; the magnitude of said output movement is independent of the magnitude of said detected movement and any combination thereof.

14. The system of claim 1, additionally comprising either a wired or wireless communicable database for storing at least one selected from a group consisting of said predetermined protocol of input movement; said predetermined protocol of output movement; and any combination thereof.

15. The system of claim 1, additionally comprising a second imaging modality, configured to generate at least one second modality image.

16. The system of claim 15, wherein said computer program, when executed by said data processor, is configured to generate an augmented reality image comprising a rendered superposition of at least a portion of said image and at least a portion of said at least one second modality image.

17. The system of claim 16, wherein said second imaging modality is selected from a group consisting of: MM, CT, PET, ultrasound, IR imaging, heat imaging, a still camera, a videocamera, image-generation software, image-manipulation software, display of stored images and any combination thereof.

18. The system of claim 15, wherein said at least one second modality image is provided in a manner selected from a group consisting of: said second modality image is real-time generated, said second modality image is a stored image and any combination thereof.

19. The system of claim 15, wherein said second modality image is selected from a group consisting of: a 2D image, a 3D image and any combination thereof.

20. The system of claim 15, wherein said stored second modality image is storable in a database in communication with said computer program.

21. The system of claim 1, wherein said computer program, when executed by said data processor, is configured to real time generate a display image by at least one of a group consisting of: (a) generating at least one virtual marker at at least one predetermined position within at least a portion of said image; (b) rendered superimposing of at least a portion of said image and at least a portion of a second imaging modality.

22. The system of claim 21, wherein said virtual marker provides information selected from a group consisting of: a distance between predetermined points, an orientation relative to a predetermined direction, an identifier, and any combination thereof.

23. The system of claim 22, wherein said identifier identifies a member of a group consisting of: at least one portion of tissue of a predetermined type, a predetermined location, a tool, and any combination thereof.

24. The system of claim 22, wherein said identifier comprises a mark of predetermined shape.

25. The system of claim 24, wherein said predetermined shape is selected from a group consisting of: a word, a geometric shape, an outline of a predetermined area, a patch covering said predetermined area, an outline of predetermined shape, a patch of said predetermined shape, and any combination thereof.

26. The system of claim 21, wherein said tissue of a predetermined type is selected from a group consisting of: an organ, a blood vessel, a bone, a nerve, a ligament, abnormal tissue and any combination thereof.

27. The system of claim 1, wherein said endoscope further comprises a wide-angle lens at the distal end of the same; wherein said wide-angle lens is selected from a group consisting of: a fish-eye lens, an omnidirectional lens, and any combination thereof.

28. The system of claim 27, additionally comprising a light source configured to illuminate at least a portion of said field of view and software which, when executed by said data processor, is configured to control said light source; further wherein said controlled light source emits a pattern comprising a structured light pattern.

29. The system of claim 28, additionally comprising software which, when executed by said data processor, is configured to generate, real time, a 3D image from at least a portion of at least one camera image generated by said structured light pattern.

30. The system of claim 1, wherein said computer program additionally comprises software which, when executed by said data processor, removes fog from at least a portion of at least one said image.

31. The system of claim 1, wherein said computer program additionally comprises software which, when executed by said data processor, visually enhances at least one of: at least a portion of a limb, at least a portion of a blood vessel, at least a portion of an organ, at least a portion of a bone, at least a portion of a nerve, at least a portion of a ligament, at least a portion of abnormal tissue and any combination thereof.

32. A maneuvering system, comprising:
a. at least one endoscope adapted to real-time provide at least one image of a field of view;
b. a first surgical tool;
c. at least one maneuvering mechanism in active communication with at least one selected from a group consisting of said at least one endoscope, said first surgical tool and any combination thereof;
said maneuvering mechanism is configured to maneuver at least one of the endoscope and the first surgical tool in at least two dimensions;
d. a processor and a memory in communication with said processor, said memory storing a plurality of predetermined input protocols and a plurality of predetermined output commands, each of the plurality of output commands corresponding to one of the input protocols, and a computer program which, when executed by the processor, is in communication with at least the endoscope or the first surgical tool;
said program, when executed by a data processor is configured to determine, from said image of said field of view, an input protocol and to, if said input protocol is within one of the predetermined input protocols activate at least one of the output commands, wherein the input command is selected from the group consisting of:
- a. at least a portion of the first surgical tool is positioned in a predetermined region of said field of view;
- b. at least a portion of the first surgical tool is positioned less than a predetermined distance from an edge of said field of view;
- c. at least a portion of the first surgical tool is oriented at a predetermined angle in said field of view;
- d. the first surgical tool is activated;
- e. the first surgical tool is deactivated;

and wherein said output command is selected from a group consisting of:
- a. at least a portion of the first surgical tool is repositioned to a predetermined region of said field of view;
- b. at least a portion of the first surgical tool is oriented at a predetermined angle in said field of view;
- d. the first surgical tool is activated;
- e. the first surgical tool is deactivated;
- f. in the first surgical tool, at least one of a group consisting of an articulation angle, an articulation length and any combination thereof is altered;
- g. the first surgical tool is tagged.

33. The system of claim 32, wherein said activation is selected from a group consisting of: opening said first surgical tool, closing said first surgical tool, causing said first surgical tool to function, stopping said first surgical tool from functioning, introducing said first surgical tool to the surgical environment, and removing said first surgical tool from the surgical environment, and any combination thereof.

* * * * *